US011900274B2

(12) United States Patent
Aravamudan et al.

(10) Patent No.: US 11,900,274 B2
(45) Date of Patent: Feb. 13, 2024

(54) SYSTEMS, METHODS, AND COMPUTER READABLE MEDIA FOR VISUALIZATION OF SEMANTIC INFORMATION AND INFERENCE OF TEMPORAL SIGNALS INDICATING SALIENT ASSOCIATIONS BETWEEN LIFE SCIENCE ENTITIES

(71) Applicant: nference, inc., Cambridge, MA (US)

(72) Inventors: Murali Aravamudan, Andover, MA (US); Venkataramanan Soundararajan, Andover, MA (US); Ajit Rajasekharan, West Windsor, NJ (US)

(73) Assignee: nference, Inc., Cambridge, MA (US)

( * ) Notice: Subject to any disclaimer, the term of this patent is extended or adjusted under 35 U.S.C. 154(b) by 239 days.

(21) Appl. No.: 17/369,757

(22) Filed: Jul. 7, 2021

(65) Prior Publication Data

US 2022/0138599 A1 May 5, 2022

Related U.S. Application Data

(63) Continuation of application No. 16/431,635, filed on Jun. 4, 2019, now Pat. No. 11,062,218, which is a (Continued)

(51) Int. Cl.
*G06N 5/04* (2023.01)
*G16B 50/00* (2019.01)
(Continued)

(52) U.S. Cl.
CPC ............. *G06N 5/04* (2013.01); *G06F 40/30* (2020.01); *G06N 5/022* (2013.01); *G16B 50/00* (2019.02);
(Continued)

(58) Field of Classification Search
None
See application file for complete search history.

(56) References Cited

U.S. PATENT DOCUMENTS

| 7,542,969 B1 | 6/2009 | Rappaport et al. |
| 9,514,405 B2 | 12/2016 | Chen et al. |

(Continued)

FOREIGN PATENT DOCUMENTS

| CN | 105938495 A | 9/2016 |
| JP | 2019-536178 A | 12/2019 |

(Continued)

OTHER PUBLICATIONS

Korger, Clustering of Distributed Word Representations and its Applicability for Enterprise Search, Doctoral Thesis, Dresden University of Technology, 2016, pp. 1-116 (Year: 2016).*

(Continued)

*Primary Examiner* — Wilbert L Starks
(74) *Attorney, Agent, or Firm* — Caldwell Intellectual Property Law

(57) ABSTRACT

Disclosed systems, methods, and computer readable media can detect an association between semantic entities and generate semantic information between entities. For example, semantic entities and associated semantic collections present in knowledge bases can be identified. A time period can be determined and divided into time slices. For each time slice, word embeddings for the identified semantic entities can be generated; a first semantic association strength between a first semantic entity input and a second semantic entity input can be determined; and a second semantic association strength between the first semantic entity input and semantic entities associated with a semantic collection that is associated with the second semantic entity (Continued)

can be determined. An output can be provided based on the first and second semantic association strengths.

22 Claims, 65 Drawing Sheets

Related U.S. Application Data continuation of application No. 15/713,426, filed on Sep. 22, 2017, now Pat. No. 10,360,507.

(60) Provisional application No. 62/514,697, filed on Jun. 2, 2017, provisional application No. 62/398,386, filed on Sep. 22, 2016.

(51) Int. Cl.
*G06N 5/022* (2023.01)
*G06F 40/30* (2020.01)
*G16B 50/10* (2019.01)
*G16B 50/30* (2019.01)
*G06N 3/044* (2023.01)

(52) U.S. Cl.
CPC .............. *G16B 50/10* (2019.02); *G16B 50/30* (2019.02); *G06N 3/044* (2023.01)

(56) References Cited

U.S. PATENT DOCUMENTS

| | | | |
|---|---|---|---|
| 9,953,095 | B1 | 4/2018 | Scott et al. |
| 10,360,507 | B2 | 7/2019 | Aravamudan et al. |
| 11,062,218 | B2 * | 7/2021 | Aravamudan ......... G16B 50/30 |
| 11,487,902 | B2 | 11/2022 | Ardhanari et al. |
| 11,545,242 | B2 | 1/2023 | Aravamudan |
| 2004/0013302 | A1 | 1/2004 | Ma et al. |
| 2007/0039046 | A1 | 2/2007 | Van Dijk et al. |
| 2008/0118150 | A1 | 5/2008 | Balakrishnan et al. |
| 2008/0243825 | A1 | 10/2008 | Staddon et al. |
| 2009/0116736 | A1 | 5/2009 | Neogi et al. |
| 2011/0255788 | A1 | 10/2011 | Duggan et al. |
| 2011/0307460 | A1 | 12/2011 | Vadlamani et al. |
| 2013/0132331 | A1 | 5/2013 | Kowalczyk et al. |
| 2015/0161413 | A1 | 6/2015 | Calem et al. |
| 2015/0254555 | A1 | 9/2015 | Williams, Jr. et al. |
| 2016/0105402 | A1 | 4/2016 | Soon-Shiong et al. |
| 2016/0247307 | A1 | 8/2016 | Stoop et al. |
| 2017/0032243 | A1 | 2/2017 | Corrado et al. |
| 2017/0061326 | A1 | 3/2017 | Talathi et al. |
| 2017/0091391 | A1 | 3/2017 | LePendu |
| 2018/0060282 | A1 | 3/2018 | Kaljurand |
| 2019/0319982 | A1 | 10/2019 | Durand et al. |
| 2019/0354883 | A1 | 11/2019 | Aravamudan et al. |
| 2020/0402625 | A1 | 12/2020 | Aravamudan et al. |
| 2021/0019287 | A1 | 1/2021 | Prasad et al. |
| 2021/0224264 | A1 | 7/2021 | Barve et al. |
| 2021/0248268 | A1 | 8/2021 | Ardhanari et al. |
| 2022/0050921 | A1 | 2/2022 | LaFever et al. |
| 2023/0051067 | A1 | 2/2023 | Ardhanari |

FOREIGN PATENT DOCUMENTS

| | | |
|---|---|---|
| WO | WO-2015084759 A1 | 6/2015 |
| WO | WO-2015149114 | 10/2015 |
| WO | WO-2018057945 | 3/2018 |
| WO | WO-2020257783 | 12/2020 |
| WO | WO-2021011776 | 1/2021 |
| WO | WO-2021146694 A1 | 7/2021 |
| WO | WO-2021178689 | 9/2021 |

OTHER PUBLICATIONS

Zuccon, et al., Integrating and Evaluating Neural Word Embeddings in Information Retrieval, ADCS, 2015, pp. 1-8 (Year: 2015).*
Freitas, Schema-Agnostic Queries for Large-Schema Databases: A Distributional Semantics Approach, Doctoral Thesis, National University of Ireland, Galway, 2015, pp. 1-396 (Year: 2015).*
Ananiadou, et al., Event Extraction for Systems Biology by Text Mining the Literature, Trends in Biotechnology vol. 28 No. 7, 2010, pp. 381-390 (Year: 2010).*
Köpcke, et al., Frameworks for Entity Matching: A Comparison, Data & Knowledge Engineering, 2009, pp. 1-14 (Year: 2009).*
AMD Secure Encrypted Virtualization (SEV), https://developer.amd.com/sev/, accessed Sep. 23, 2020 (5 pages).
Arora, S. et al., "A Simple But Tough-To-Beat Baseline for Sentence Embeddings", ICLR, 2017 (16 pages).
AWS Key Management Service (KMS), https://aws.amazon.com/kms, accessed Jan. 20, 2021 (3 pages).
AWS Key Management Service (KMS), https://aws.amazon.com/kms, accessed Sep. 23, 2020 (6 pages).
Bartunov, S. et al., "Breaking Sticks And Ambiguities With Adaptive Skip-Gram", retrieved online from URL:< https://arxiv.org/pdf/1502.07257.pdf>, [cs.CL], Nov. 15, 2015 (15 pages).
Bojanowski, P. et al., "Enriching Word Vectors with Subword Information", retrieved online from URL:<https://arxiv.org/pdf/1607.04606.pdf>, [cs.CL], Jun. 19, 2017 (12 pages).
Confidential Computing Consortium, "What is the Confidential Computing Consortium?", https://confidentialcomputing.io, accessed Sep. 24, 2020 (2 pages).
De Guzman, C.G. et al., "Hematopoietic Stem Cell Expansion and Distinct Myeloid Developmental Abnormalities in a Murine Model of the AML1-ETO Translocation", Molecular and Cellular Biology, 22(15):5506-5517, Aug. 2002 (12 pages).
Desaguiler, G., "A lesson from associative learning: asymmetry and productivity in multiple-slot constructions", Corpus Linguisitic and Linguistic Theory, 12(2):173-219, 2016, submitted Aug. 13, 2015, <http://www.degruyter.com/view/j/cllt.2016.12.issue-2/cllt-2015-0012/cllt-2015-0012.XML?format=INT>. <10.1515/cllt-2015-0012>. <halshs-01184230>, (32 pages).
Devlin, J. et al., "BERT: Pre-training of Deep Bidirectional Transformers for Language Understanding", arXiv:1810.04805v2 [cs.CL], May 24, 2019 (16 pages).
Divatia, A., "The Fact and Fiction of Homomorphic Encryption", Dark Reading, www.darkreading.com/attacks-breaches/the-fact-and-fiction-of-homomorphic-encryption/a/d-id/1333691, Jan. 22, 2019 (3 pages).
Dwork, C., "Differential Privacy: A Survey of Results", Lecture Notes in Computer Science, vol. 4978, pp. 1-19, 2008 (19 pages).
Ferraiuolo, A. et al., "Komodo: Using verification to disentangle secure-enclave hardware from software", SOSP '17, Shanghai, China, pp. 287-305, Oct. 28, 2017 (19 pages).
Garten, Y. et al., "Pharmspresso: a text mining tool for extraction of pharmacogenomic concepts and relationships from full text", BMC Bioinformatics, 10(Suppl. 2):S6, Feb. 5, 2009 (9 pages).
Genkin, D. et al., "Privacy in Decentralized Cryptocurrencies", Communications of the ACM, 61(6):78-88, Jun. 2018 (11 pages).
Hageman, G.S. et al., "A common haplotype in the complement regulatory gene factor H (HF1 / CFH) predisposes individuals to age-related macular degeneration", PNAS, 102(20):7227-7232, May 17, 2005 (6 pages).
Ikeda, T. et al., "Anticorresponding mutations of the KRAS and PTEN genes in human endometrial cancer", Oncology Reports, 7: 567-570, published online May 1, 2000 (4 pages).
Intel, "What is Intel® SGX?", http://www.intel.com/content/www/US/en/architecture-and-technology/software-guard-extensions.html, accessed Sep. 23, 2020 (8 pages).
International Search Report and Written Opinion issued by the European Patent Office as International Searching Authority in International Application PCT/US2017/053039, dated Dec. 20, 2017 (15 pages).
International Search Report and Written Opinion issued by the U.S. Patent and Trademark Office as International Searching Authority issued in International Application No. PCT/US21/20906, dated May 19, 2021 (10 pages).

(56) References Cited

OTHER PUBLICATIONS

International Search Report and Written Opinion issued by U.S. Patent and Trademark Office as International Searching Authority in International Application No. PCT/US20/42336, dated Sep. 30, 2020 (10 pages).
International Search Report and Written Opinion issued by U.S. Patent and Trademark Office as International Searching Authority, for International Application No. PCT/US20/38987, dated Nov. 9, 2020 (26 pages).
Joulin, A. et al., "Bag of Tricks for Efficient Text Classification", retrieved online from URL:<https://arXiv.org/pdf/1607.01759v3.pdf>, [cs.CL], Aug. 9, 2016 (5 pages).
Kiros, R. et al., "Skip-Thought Vectors", retrieved online from URL:<https://arXiv.org/abs/1506.06726v.1>, [cs.CL], Jun. 22, 2015 (11 pages).
Kolte, P. "Why Is Homomorphic Encryption Not Ready For Primetime?", Baffle, https://baffle.io/blog/why-is-homomorphic-encryption-not-ready-for-primetime/, Mar. 17, 2017 (4 pages).
Korger, C., "Clustering of Distributed Word Representations and its Applicability for Enterprise Search", Doctoral Thesis, Dresden University of Technology, Faculty of Computer Science, Institute of Software and Multimedia Technology, Matriculation Nr. 3703541, submitted Jul. 28, 2016 (116 pages).
Kutuzov, A et al., "Cross-lingual Trends Detection for Named Entities in News Texts with Dynamic Neural Embedding Models", Proceedings of the NewsIR'16 Workshop at ECIR, Padua, Italy, Mar. 20, 2016 (6 pages).
Le, Q. et al., "Distributed Representations of Sentences and Documents", Proceedings of the 31st International Conference of Machine Learning, Beijing, China, vol. 32, 2014 (9 pages).
Li, H. et al., "Cheaper and Better: Selecting Good Workers for Crowdsourcing," retrieved online from URL: https://arXiv.org/abs/1502.00725v.1, pp. 1-16, Feb. 3, 2015 (16 pages).
Ling, W. et al., "Two/Too Simple Adaptations of Word2Vec for Syntax Problems", retrieved online from URL:<https://cs.cmu.edu/~lingwang/papers/naacl2015.pdf>, 2015 (6 pages).
Maxwell, K.N. et al., "Adenoviral-mediated expression of Pcsk9 in mice results in a low-density lipoprotein receptor knockout phenotype", PNAS, 101(18):7100-7105, May 4, 2004 (6 pages).
Mikolov, T. et al., "Distributed Representations for Words and Phrases and their Compositionality", retrieved online from URL:https://arXiv.org/abs/1310.4546.v1 [cs.CL], Oct. 16, 2013 (9 pages).
Mikolov, T. et al., "Efficient Estimation of Word Representations in Vector Space", retrieved online from URL: https://arXiv.org/abs/1301.3781v3 [cs.CL] Sep. 7, 2013 (12 pages).
Murray, K., "A Semantic Scan Statistic for Novel Disease Outbreak Detection", Master's Thesis, Carnegie Mellon University, Aug. 16, 2013 (68 pages).
Neelakantan, A., et al., "Efficient Non-parametric Estimation of Multiple Embeddings per Word in Vector Space," Department of Computer Science, University of Massachusetts, (2015) (11 pages).
Pennington, J. et al., "GloVe: Global Vectors for Word Representation", retrieved online from URL:<https://nlp.stanford.edu/projects/glove.pdf>, 2014 (12 pages).
Rajagopalan, H., et al., "Tumorigenesis: RAF/RAS oncogenes and mismatch-repair status", Nature, 418:934, Aug. 29, 2002 (1 page).
Rajasekharan, "Unsupervised NER using BERT", [accessed Jun. 10, 2021], Toward Data Science, <URL: https://towardsdatascience.com/unsupervised-ner-using-bert-2d7af5f90b8a>, Feb. 28, 2020 (27 pages).
Shamir, A. "How to Share a Secret", Communications of the ACM, 22(11):612-613, Nov. 1979 (2 pages).
Shweta, Fnu et al., "Augmented Curation of Unstructured Clinical Notes from a Massive EHR System Reveals Specific Phenotypic Signature of Impending COVID-19 Diagnosis", https://www.medrxiv.org/content/10.1101/2020.04.19.20067660v3.full, accessed Sep. 24, 2020 (24 pages).
Van Mulligen, E.M. et al., "The EU-ADR corpus: Annotated drugs, diseases, targets, and their relationships", Journal of Biomedical Informatics, 45:879-884, published online Apr. 25, 2012 (6 pages).
Wieting, J. et al., "Revisiting Recurrent Networks for Paraphrastic Sentence Embeddings", retrieved online from URL:<https://arXiv.org/pdf/1705.00364v1.pdf>, [cs.CL], Apr. 30, 2017 (12 pages).
Yao, Z. et al., "Dynamic Word Embeddings for Evolving Semantic Discovery", WSDM 2018, Marina Del Rey, CA, USA, Feb. 5-9, 2018 (9 pages).
Zuccon, G., et al., "Integrating and Evaluating Neural Word Embeddings in Information Retrieval", ADCS, Parramatta, NSW, Australia, Dec. 8-9, 2015 (8 pages).
International Preliminary Report on Patentability issued in International Application No. PCT/US2021/020906, dated Sep. 15, 2022 (9 pages).

* cited by examiner

Google | aml | 🔍

All  News  Images  Books  Videos  More▽  Search tools

About 27,700,000 results (0.42 seconds)

Acute Myeloid Leukemia: Overview & Treatment Options | CTCA
www.cancercenter.com › ... › Learning ▽ Cancer Treatment Centers of America ▽
Acute myeloid leukemia (AML), also known as acute myelogenous leukemia, acute myeloblastic leukemia, acute granulocytic leukemia or acute nonlymphocytic leukemia, is a fast-growing form of cancer of the blood and bone marrow. ... In AML, the bone marrow may also make abnormal red ...

Adult Acute Myeloid Leukemia Treatment (PDQ®)-Patient Version ...
https://www.cancer.gov/types/.../adult-aml-treatment-pdq ▽ National Cancer Institute ▽
Jul 28, 2016 - Adult acute myeloid leukemia (AML) is a type of cancer in which the bone marrow makes abnormal myeloblasts (a type of white blood cell), red ...

Acute Myeloid Leukemia (AML) | Learn About Cancer | American ...
www.cancer.org/cancer/leukemia-acutemyeloid/aml/ ▽ American Cancer Society ▽
Acute myeloid leukemia is also called acute myelocytic leukemia, acute myelogenous leukemia, acute granulocytic leukemia, acute non-lymphocytic leukemia, ...

Acute Myeloid Leukemia | Leukemia and Lymphoma Society
www.lls.org/leukemia/acute-myeloid-leukemia ▽ Leukemia & Lymphoma Society ▽
Information about acute myeloid leukemia (AML), including what you should know and what you should do if you have AML.

AML Subtypes | Leukemia and Lymphoma Society
https://www.lls.org/leukemia/acute.../aml-subtypes ▽ Leukemia & Lymphoma Society ▽
It's important to know your acute myeloid leukemia (AML) subtype because it plays a large part in determining the type of treatment you'll receive.

| People also ask | |
|---|---|
| What is acute myeloid leukemia? | ⌄ |
| What is AML compliance? | ⌄ |
| What does myelogenous mean? | ⌄ |
| What does AML stand for in medical terms? | ⌄ |

Acute myeloid leukemia - Wikipedia, the free encyclopedia
https://en.wikipedia.org/wiki/Acute_myeloid_leukemia ▽ Wikipedia ▽
Acute myeloid leukemia (AML), also known as acute myelogenous leukemia or acute nonlymphocytic leukemia (ANLL), is a cancer of the myeloid line of blood ...
Acute promyelocytic leukemia - Acute myelomonocytic leukemia - Auer rod

---

Acute myeloid leukemia
Also called: AML, AML leukemia

| ABOUT | SYMPTOMS | TREATMENTS |
|---|---|---|

A type of cancer of the blood and bone marrow with excess immature white blood cells.

Rare
Fewer than 200,000 US cases per year

- Treatable by a medical professional
- Requires a medical diagnosis
- Lab tests or imaging always required AML progresses rapidly, with myeloid cells interfering with the production of normal white blood cells, red blood cells, and platelets.

Symptoms include fatigue, recurrent infections, and bruising easily.

Treatments include chemotherapy, other drug therapy, and stem-cell transplants.

Ages affected
0-2
3-5
6-13
14-18
19-40
41-60
60+

Critical: consult a doctor for medical advice
Sources: Mayo Clinic and others. Learn more ⬇ Download PDF                           Feedback

FIG. 2A

Google | aml | 🎤 | 🔍

All  News  Images  Books  Videos  More▽  Search tools

About 27,700,000 results (0.42 seconds)

Acute Myeloid Leukemia: Overview & Treatment Options | CTCA
www.cancercenter.com > ... > Learning ▽ Cancer Treatment Centers of America ▽
Acute myeloid leukemia (AML), also known as acute myelogenous leukemia, acute myeloblastic leukemia, acute granulocytic leukemia or acute nonlymphocytic leukemia, is a fast-growing form of cancer of the blood and bone marrow. ... In AML, the bone marrow may also make abnormal red ...

Adult Acute Myeloid Leukemia Treatment (PDQ®)-Patient Version ...
https://www.cancer.gov/types/.../adult-aml-treatment-pdq ▽ National Cancer Institute ▽
Jul 28, 2016 - Adult acute myeloid leukemia (AML) is a type of cancer in which the bone marrow makes abnormal myeloblasts (a type of white blood cell), red ...

Acute Myeloid Leukemia (AML) | Learn About Cancer | American ...
www.cancer.org/cancer/leukemia-acutemyeloid/aml/ ▽ American Cancer Society ▽
Acute myeloid leukemia is also called acute myelocytic leukemia, acute myelogenous leukemia, acute granulocytic leukemia, acute non-lymphocytic leukemia, ...

Acute Myeloid Leukemia | Leukemia and Lymphoma Society
www.lls.org/leukemia/acute-myeloid-leukemia ▽ Leukemia & Lymphoma Society ▽
Information about acute myeloid leukemia (AML), including what you should know and what you should do if you have AML.

AML Subtypes | Leukemia and Lymphoma Society
https://www.lls.org/leukemia/acute.../aml-subtypes ▽ Leukemia & Lymphoma Society ▽
It's important to know your acute myeloid leukemia (AML) subtype because it plays a large part in determining the type of treatment you'll receive.

| People also ask | |
|---|---|
| What is acute myeloid leukemia? | ˅ |
| What is AML compliance? | ˅ |
| What does myelogenous mean? | ˅ |
| What does AML stand for in medical terms? | ˅ |

Acute myeloid leukemia - Wikipedia, the free encyclopedia
https://en.wikipedia.org/wiki/Acute_myeloid_leukemia ▽ Wikipedia ▽
Acute myeloid leukemia (AML), also known as acute myelogenous leukemia or acute nonlymphocytic leukemia (ANLL), is a cancer of the myeloid line of blood ...
Acute promyelocytic leukemia - Acute myelomonocytic leukemia - Auer rod

---

301

Acute myeloid leukemia
Also called: AML, AML leukemia

| ABOUT | SYMPTOMS | TREATMENTS |
|---|---|---|

A type of cancer of the blood and bone marrow with excess immature white blood cells.

Rare
Fewer than 200,000 US cases per year

⊕ Treatable by a medical professional
▦ Requires a medical diagnosis
⊙ Lab tests or imaging always required AML progresses rapidly, with myeloid cells interfering with the production of normal white blood cells, red blood cells, and platelets.

Symptoms include fatigue, recurrent infections, and bruising easily.

Treatments include chemotherapy, other drug therapy, and stem-cell transplants.

Ages affected
0-2
3-5
6-13
14-18
19-40
41-60
60+

Critical: consult a doctor for medical advice
Sources: Mayo Clinic and others. Learn more ⬇ Download PDF                                    Feedback

| Word | Dist | Class | Occurrences | Bionco |
|---|---|---|---|---|
| Rufinamide | 0.871 | 43 | 579 | Rufinamide |
| Levetiracetam | 0.827 | 43 | 3776 | Levetiracetam |
| Zonisamide | 0.816 | 43 | 1711 | Zonisamide |
| Oxcarbazepine | 0.81 | 43 | 1271 | Oxcarbazepine |
| Lamotrigine | 0.804 | 43 | 5574 | Lamotrigine |
| Clobazam | 0.802 | 43 | 1010 | Clobazam |
| Partial-onset seizures | 0.802 | 52 | 268 | |
| Perampanel | 0.8 | 43 | 723 | Perampanel |
| Topiramate | 0.798 | 43 | 7403 | Topiramate |
| Load More | | | | |

Search: lacosamide

FIG. 5A

```
Analogy: Example (Target:Drug)
analogy&tokens=anti-egfr.erlotinib.infliximab
{
  - result: {
    - nearest: [
      - {
          dist: 0.773298978805542,
          cooccurrences: -1,
          has backlink: 0,
          occurrences: 19090,
          word: "infliximab",
          class: 52
        },
      - {
          dist: 0.7472701072692871,
          cooccurrences: -1,
          has backlink: 0,
          occurrences: 10043,
          word: "anti-tnf",
          class: 164
        },
      - {
          dist: 0.7337853908538818,
          cooccurrences: -1,
          has backlink: 0,
          occurrences: 850,
          word: "anti-tumor_necrosis_factor",
          class: 164
        },
```

FIG. 6A

```
Analogy: Example (Genotype:Drug)
analogy&tokens=t315i,ponatinib,co-1686
{
  - result: {
      - nearest: [
          - {
              dist: 0.8511573672294617,
              cooccurrences: -1,
              has_backlink: 0,
              occurrences: 63,
              word: "co-1686",
              class: 408
          },
          - {
              dist: 0.7182760834693909,
              cooccurrences: -1,
              has_backlink: 0,
              occurrences: 270,
              word: "egfr_t790m",
              class: 408
          },
          - {
              dist: 0.7079435586929321,
              cooccurrences: -1,
              has_backlink: 0,
              occurrences: 203,
              word: "gatekeeper_mutation",
              class: 336
          },
```

FIG. 6B

Examples 3-4 (Disease:Drug)
analogy&tokens=arthritis,certolizumab,rotigotine

```
result: [
 - nearest: [
   -
     dist: 0.6249468868896484,
     cooccurrences: -1,
     has_backlink: 0,
     occurrences: 1153,
     word: "rotigotine",
     class: 52
   },
   {
     dist: 0.5885915756225586,
     cooccurrences: -1,
     has_backlink: 0,
     occurrences: 188,
     word: "parkinsonian_signs",
     class: 413
   },
   {
     dist: 0.5783960223197937,
     cooccurrences: -1,
     has_backlink: 0,
     occurrences: 8550,
     word: "parkinsonism",
     class: 242
   },
```

FIG. 6C

Examples 3-4 (Disease:Drug)
analogy&tokens=zyrtec,allergy,hypercholesterolemia

```
result: {
 - nearest: [
   -
     dist: 0.6767646670341492,
     cooccurrences: -1,
     has_backlink: 0,
     occurrences: 28,
     word: "zetia",
     class: 164
   },
   {
     dist: 0.6666287183761597,
     cooccurrences: -1,
     has_backlink: 0,
     occurrences: 38,
     word: "rosuvastatin_monotherapy",
     class: 52
   },
   {
     dist: 0.6615378856658936,
     cooccurrences: -1,
     has_backlink: 0,
     occurrences: 18148,
     word: "hypercholesterolemia",
     class: 200
   },
```

FIG. 6D

| Drug | Distance | Count | Disease | Distance | Count | Gene | Distance | Count |
|---|---|---|---|---|---|---|---|---|
| Myelin | 0.824434 | 52509 | Wallerian Degeneration | 0.759667 | 4637 | OLIG1 | 0.624988 | 2378 |
| Oligodendrocyte Progenitor Cells | 0.762599 | 1365 | Demyelinating Diseases | 0.717109 | 1648 | CNTF | 0.61491 | 8812 |
| RHIGM22 | 0.643451 | 425 | Nerve Degeneration | 0.661832 | 638 | GALC | 0.580232 | 1997 |
| HUCNS-SC | 0.552686 | 148 | Gliosis | 0.657956 | 11022 | GPR17 | 0.576954 | 1411 |
| Ciliary Neurotrophic Factor | 0.542494 | 1710 | Retrograde Degeneration | 0.645036 | 575 | MOG | 0.566979 | 8911 |
| Glatiramer Acetate | 0.537379 | 4111 | Multiple Sclerosis | 0.573518 | 124479 | MBP | 0.556722 | 60685 |
| Callosum | 0.535874 | 1035 | Peripheral Nerve Injuries | 0.571362 | 1087 | OLIG2 | 0.55453 | 9971 |
| Laquinimod | 0.53244 | 2162 | Neuritis | 0.526887 | 2478 | GFAP | 0.547296 | 48882 |
| Fingolimod | 0.529272 | 7957 | Pelizaeus-Merzbacher Disease (PMD) | 0.524782 | 466 | GAP43 | 0.545755 | 3563 |
| Regrowth | 0.526994 | 11599 | Optic Neuritis | 0.514166 | 8193 | MAG | 0.538796 | 20480 |
| GGF2 | 0.523249 | 356 | Spinal Cord Injuries | 0.496657 | 4656 | LGI4 | 0.536368 | 374 |
| NT-020 | 0.516719 | 199 | Diffuse Axonal Injury | 0.490703 | 1963 | PMP22 | 0.536337 | 4075 |
| CNL8 | 0.50754 | 2 | Neuromyelitis Optica | 0.486983 | 3707 | AMIGO3 | 0.523258 | 168 |
| PXT3003 | 0.504906 | 142 | Brain Ischemia | 0.477542 | 5885 | PLP1 | 0.510911 | 1692 |
| ISX-9 | 0.503646 | 76 | Encephalomyelitis | 0.471446 | 3278 | NT3 | 0.506822 | 3390 |
| Ciliary Neurotrophic | 0.500478 | 94 | Leukoencephalopathies | 0.469409 | 158 | GDNF | 0.50478 | 26845 |
| ATI355 | 0.496962 | 14 | Brain Edema | 0.468198 | 7799 | OPALIN | 0.501913 | 55 |
| Neuroregen | 0.493741 | 17 | Fasciculation | 0.44941 | 2415 | MPZ | 0.497835 | 1272 |
| GRNOPC1 | 0.487186 | 102 | Myelitis | 0.438885 | 2665 | CMT1A | 0.49551 | 1766 |
| CTX0E03 | 0.486768 | 69 | Amyotrophic Lateral Sclerosis | 0.430531 | 26729 | LINGO1 | 0.495043 | 423 |
| UCBMC | 0.484196 | 76 | Canavan Disease | 0.426048 | 775 | KLK6 | 0.494409 | 2544 |
| Nestorone | 0.478969 | 134 | Leukodystrophy Globoid Cell | 0.420882 | 33 | MOBP | 0.491253 | 514 |
| ACTHAR | 0.477643 | 507 | Polyneuropathies | 0.410213 | 575 | NFASC | 0.48233 | 555 |
| BIIB033 | 0.477325 | 161 | Facial Nerve Injuries | 0.41012 | 47 | NGF | 0.477446 | 62487 |
| Sulfatide | 0.472923 | 4376 | Inflammation | 0.408374 | 868937 | DCX | 0.47687 | 11657 |
| Gongjin-dan | 0.470789 | 61 | Motor Neuron Disease | 0.405551 | 4743 | ASPA | 0.473914 | 2188 |
| 2B3-201 | 0.470224 | 78 | Astrocytoma | 0.403522 | 9473 | RGMA | 0.473587 | 1338 |
| Olesoxime | 0.4684 | 451 | Spinal Cord Ischemia | 0.403241 | 1147 | NRCAM | 0.47215 | 2682 |
| Intrathecal | 0.464686 | 9914 | Infarction | 0.401296 | 39683 | AQP4 | 0.46901 | 14164 |

Fig 11. Synthesized matrix of temporal progression

Fig 12. Synthesized matrix of temporal progression of concepts across entity classes Fig 13. Knowledge Graph Generation Fig 14. Temporal progression capture in KG

| Rank | Word | Semantic Association Strength | Occurrences | Documents |
|---|---|---|---|---|
| 0 | pearson[1] | 0.81 | 247,473 | 6,949 |
| 1 | spearman[2] | 0.77 | 96,393 | 7,553 |
| 2 | coefficient[2] | 0.74 | 622,864 | 13,063 |
| 3 | rank-correlation[1] | 0.72 | 411 | 3,146 |
| 4 | spearman[3] | 0.72 | 96,393 | 7,553 |
| 5 | scatterplots[1] | 0.72 | 5,796 | 327 |

FIG. 52

| Rank | Word | Semantic Association Strength | Occurrences | Documents |
|---|---|---|---|---|
| 0 | sigma² | 0.97 | 398,440 | 33,599 |
| 1 | m¹ | 0.97 | 178,302 | 5,759 |
| 2 | p² | 0.97 | 175,068 | 15,307 |
| 3 | psi | 0.98 | 94,109 | 2,598 |
| 4 | z | 0.98 | 1,164,804 | 101,269 |
| 5 | nu² | 0.98 | 40,180 | 1,080 |

FIG. 53

| Rank | Word | Semantic Association Strength | Occurrences | Documents |
|---|---|---|---|---|
| 0 | actin-related[4] | 0.61 | 2,057 | 14 |
| 1 | Rho[5] | 0.6 | 132 | 23 |
| 2 | guanosine[3] | 0.58 | 103,166 | 4,561 |
| 3 | ACTSC[3] | 0.58 | 549 | 49 |
| 4 | RHOA[6] | 0.58 | 81,080 | 19,097 |
| 5 | nucleotide[3] | 0.58 | 855,942 | 30,834 |

FIG. 54

| Rank | Word | Semantic Association Strength | Occurrences | Documents |
|---|---|---|---|---|
| 0 | lassify² | 0.91 | 2,704 | 331 |
| 1 | kampaz | 0.89 | 713 | 192 |
| 2 | rush² | 0.87 | 5,422 | 388 |
| 3 | ventures¹ | 0.84 | 218,738 | 1,247 |
| 4 | fifth⁴ | 0.82 | 1,772 | 168 |
| 5 | disclaims¹ | 0.82 | 101,543 | 546 |

FIG. 55

SYSTEMS, METHODS, AND COMPUTER READABLE MEDIA FOR VISUALIZATION OF SEMANTIC INFORMATION AND INFERENCE OF TEMPORAL SIGNALS INDICATING SALIENT ASSOCIATIONS BETWEEN LIFE SCIENCE ENTITIES

RELATED APPLICATIONS

This application is a continuation of U.S. patent application Ser. No. 16/431,635 filed on Jul. 4, 2019, titled "SYSTEMS, METHODS, AND COMPUTER READABLE MEDIA FOR VISUALIZATION OF SEMANTIC INFORMATION AND INFERENCE OF TEMPORAL SIGNALS INDICATING SALIENT ASSOCIATIONS BETWEEN LIFE SCIENCE ENTITIES," which is a continuation of U.S. patent application Ser. No. 15/713,426, filed on Sep. 22, 2017, titled "SYSTEMS, METHODS, AND COMPUTER READABLE MEDIA FOR VISUALIZATION OF SEMANTIC INFORMATION AND INFERENCE OF TEMPORAL SIGNALS INDICATING SALIENT ASSOCIATIONS BETWEEN LIFE SCIENCE ENTITIES," now U.S. Pat. No. 10,360,507, which claims benefit under 35 U.S.C. § 119(e) to U.S. Provisional Patent Applications No. 62/398,386, filed on Sep. 22, 2016, titled "METHODS OF AND SYSTEMS FOR VISUALIZATION OF SEMANTIC INFORMATION," and U.S. Provisional Patent Applications No. 62/514,697, filed on Jun. 2, 2017, titled "METHODS AND SYSTEMS FOR INFERENCE OF TEMPORAL SIGNALS INDICATING SALIENT ASSOCIATIONS BETWEEN LIFE SCIENCE ENTITIES," which are explicitly incorporated by reference herein in their entirety.

BACKGROUND OF THE INVENTION

Technical Field

Embodiments of the present disclosure relate to systems, methods, and computer readable media for analyzing underlying relationships in data.

Description of the Related Art

The sophistication in visualization of data—particularly exploiting two dimensional and three dimensional layouts in contrast to linear—has rapidly advanced, facilitating the comprehension of data and underlying relationships, regardless of the data being multi-dimensional or real time. However, these visualization methods are less effective for rendering data sources, where information is unstructured, and where semantic reasoning is required to extract structured information.

Certain data sources are rich in unstructured and semi-structured information, and generally accessed in distinct siloes across different constituents of the pharmaceutical industry. For instance, the clinicaltrials.gov website is typically accessed by translational medicine and clinical development teams; whereas the Federal adverse event reporting system (FAERS) is usually accessed by pharmacovigilance Research and Development (R&D) scientists and commercial data scientists conducting market research, etc.

Currently, many challenges exist in generating synopsis/summary responses to user queries, particularly when the responses require semantic synthesis using structured and unstructured information from disparate sources. For example, in current systems, "synopsis-style responses," that attempt to graduate beyond just spewing matching results to user query, are simple in nature (e.g., single source, trivial summaries lacking semantic depth in generated responses) allowing automation (e.g., real time scores or election status tables for queries such as "nfl playoffs" or "2012 elections").

There is hence a need for a superior visualization system for presenting semantic information.

Some methods in the prior art rely on identifying seminal associations between entity pairs by studying the growth over time of documents citing both entities (i.e., documents with co-occurrences of the entity pairs). Such methods often harbor minimal predictive power, especially when the number of documents with co-occurrences is still very small (i.e., the knowledge of the association is in the incipient stages). By definition, these methods can only capture seminal associations at their moment of disclosure and cannot do so before they are published. Methods such as Citation Index also suffer from the need for long monitoring time-periods before any significant inference can be made. By looking at the citations for a given publication, a positive signal will emerge significantly after the seminal association was disclosed, but such a signal cannot be used for predictions.

Other methods in the prior art (e.g. Google's word2vec) do not provide insights on temporal analytics of entity associations. Furthermore, generic methods in the prior art for Natural Language Processing (NLP) suffer from multiple drawbacks in their application to any specific industry (such as Life Sciences) due to the inherent difficulties in entity recognition (e.g., drugs, genes, diseases) from unstructured sources caused by industry specific usage of language.

There is hence a need for a superior system that flags nascent and potentially seminal associations and tracks their salience over time.

SUMMARY

In accordance with the disclosed subject matter, systems, methods, and computer readable media are provided for the visualization of semantic information and inference of temporal signals indicating salient associations between life science entities.

Before explaining example embodiments consistent with the present disclosure in detail, it is to be understood that the disclosure is not limited in its application to the details of constructions and to the arrangements set forth in the following description or illustrated in the drawings. The disclosure is capable of embodiments in addition to those described and is capable of being practiced and carried out in various ways. Also, it is to be understood that the phraseology and terminology employed herein, as well as in the abstract, are for the purpose of description and should not be regarded as limiting. Furthermore, while the discussion in this disclosure focuses on the field of life science, applications of disclosed systems and methods are not limited to this field.

A method of detecting an association between semantic entities according to one embodiment of the present disclosure can include identifying semantic entities and associated semantic collections present in one or more knowledge bases, wherein the semantic entities include one or more of single words or multi-word phrases, and the semantic entities of a semantic collection share an entity type; determining a time period for analysis; dividing the time period into one or more time slices; generating, for each time slice, a set of word embeddings for the identified semantic entities based on one or more corpora; determining, for each time slice, a first semantic association strength between a first semantic entity input and a second semantic entity input; determining, for each time slice, a second semantic association strength between the first semantic entity input and a plurality of semantic entities in a semantic collection that is associated with the second semantic entity; and providing an output based on the first and second semantic association strengths for the one or more time slices.

According to some embodiments, the one or more corpora can include structured data and unstructured data.

According to some embodiments, the identifying semantic entities can include one or more of: (1) automatic methods of identifying one or more single words or multi-word phrases as semantic entities belonging to semantic collections and (2) selecting one or more single words or multi-word phrases forcibly from the one or more knowledge bases.

According to some embodiments, the one or more single words or multi-word phrases can be selected forcibly from information compiled from a structured database.

According to some embodiments, the identifying semantic entities can be performed on all text in the one or more knowledge bases for the time period.

According to some embodiments, the word embeddings can be generated using one or more of Word2vec, AdaGram, fastText, and Doc2vec.

According to some embodiments, the word embeddings can be generated for each time slice independently of word embeddings generated for other time slices.

According to some embodiments, the word embeddings for a time slice can be generated by leveraging word embeddings from a previous time slice.

According to some embodiments, the plurality of semantic entities associated with the semantic collection that is associated with the second semantic entity may not include the second semantic entity.

According to some embodiments, the second semantic association strength can be a mean, a median, or a percentile of a set of semantic association strengths between the first semantic entity input and the plurality of semantic entities associated with a semantic collection that is associated with the second semantic entity.

According to some embodiments, the method can further include detecting an increase in the first semantic association strength of a first time slice relative to the first semantic association strength of a second, subsequent time slice; and determining whether the increase in the first semantic association strength is statistically significant relative to the corresponding second semantic association.

According to some embodiments, the statistical significance of the increase can be determined based on a p-value as a measure of statistical significance of the first semantic association strength relative to the corresponding second semantic association.

According to some embodiments, the method can further include selecting the first entity input and the second entity input based on a level of co-occurrence between the first entity and the second entity in the one or more knowledge bases.

According to some embodiments, the level of co-occurrence between the first entity and the second entity is zero.

According to some embodiments, the method can further include receiving the first entity input and the second entity input from a user.

According to some embodiments, the method can further include determining, for each time slice, a count of documents present in the one or more corpora containing the first entity and the second entity; and determining a time difference between (1) a first date associated with an increase in the first semantic association strength for a first time slice relative to the first semantic association strength for a second, subsequent time slice and (2) a second date associated with an increase in a count of documents containing the first entity and the second entity for a third time slice relative to a count of documents containing the first entity and the second entity for a fourth time slice.

According to some embodiments, the method can further include detecting the increase in the count of documents containing the first entity and the second entity based on a slope of a curve in a fixed axis, wherein the curve is based on the time period on an x-axis of the curve and the count of documents on a y-axis of the curve.

According to some embodiments, the method can further include detecting the second increase in the count of documents containing the first entity and the second entity based on a document count threshold.

According to some embodiments, each of the first entity and the second entity can be at least one of the following entity types: bio-molecules, bio-entities, diseases, adverse events, phenotypes, companies, institutions, universities, hospitals, people, drugs, medical instruments, and medical procedures.

According to some embodiments, the output can enable a user device to display a graph line that is created by plotting each of the first semantic association strengths for each of the time slices over the time period.

According to some embodiments, the output can enable a user device to display a graph line that is created by plotting each of mean second semantic association strengths for each of the time slices over the time period.

According to some embodiments, the output can enable a user device to display a graph line that is created by plotting a count of documents present in the one or more corpora containing the first entity and the second entity for each of the time slices over the time period.

A method of generating semantic information between entities according to one embodiment of the present disclosure can include identifying a plurality of semantic entities in one or more corpora, wherein the semantic entities include one or more of single words or multi-word phrases; identifying a plurality of semantic entity types in the one or more corpora; associating one or more semantic entity types with the semantic entities of the plurality of semantic entities; generating word embeddings for the plurality of semantic entities; determining one or more semantic association scores between semantic entities from the plurality of semantic entities based on the word embeddings; receiving a query term; generating a first list of resulting semantic entities associated with the query term based on the one or more semantic association scores; generating a second list of semantic entity collections based on the semantic entity types associated with the semantic entities of the first list of resulting semantic entities, wherein each semantic entity collection from the second list is associated with a semantic entity type; and providing an output based on the second list of semantic entity collections.

According to some embodiments, the one or more corpora can include structured data and unstructured data.

According to some embodiments, the plurality of semantic entity types can be identified based on one or more of: a structured database, a custom list of entity types, an output from a neural network, an output from supervised machine learning, or an output from unsupervised machine learning.

According to some embodiments, the neural network architecture can be one or more of: a recurrent neural network (RNN) or a Long Short Term Memory (LSTM).

According to some embodiments, the word embeddings can be generated using one or more of Word2vec, AdaGram, fastText, and Doc2vec.

According to some embodiments, the generating the second list of semantic entity collections based on the semantic entity types associated with the semantic entities of the first list of resulting semantic entities can include basing the generation on only those resulting semantic entities that satisfy one or more of the following conditions: a maximum number of resulting semantic entities being associated with a potential semantic entity type; a minimum semantic association score for a resulting semantic entity; a minimum number of occurrences of the resulting semantic entity in the one or more corpora; the resulting semantic entity occurring in a minimum number of documents of the one or more corpora; a minimum number of co-occurrences of the query term and the resulting semantic entity; a maximum number of co-occurrences of the query term and the resulting semantic entity; a minimum number of documents of the one or more corpora where the query term and the resulting semantic entity co-occur; and a maximum number of documents of the one or more corpora where the query term and the resulting semantic entity co-occur.

According to some embodiments, the generating the second list of semantic entity collections can include limiting a number of semantic entity collections in the second list to a maximum number.

According to some embodiments, the generating the second list of semantic entity collections can include requiring a minimum number of semantic entities in each of the semantic entity collections of the second list.

According to some embodiments, the generating the second list of semantic entity collections can include requiring a minimum semantic association score for each of the semantic entities in each of the semantic entity collections of the second list.

According to some embodiments, the generating the second list of semantic entity collections can be further based on the one or more resulting semantic entities being associated with selected semantic entity collections.

According to some embodiments, the output can enable a user device to list one or more of the resulting semantic entities from the first list, and one or more of the semantic entity collections from the second list.

A method of generating semantic information between entities according to one embodiment of the present disclosure can include identifying a plurality of semantic entities in one or more corpora, wherein the semantic entities include one or more of single words or multi-word phrases; generating word embeddings for the plurality of semantic entities, wherein at least one of the semantic entities is a multi-meaning semantic entity having a plurality of meanings and a corresponding plurality of word embeddings, wherein each meaning is associated with a corresponding word embeddings; determining one or more semantic association scores between semantic entities from the plurality of semantic entities based on the word embeddings; receiving a query term; determining if the query term corresponds to a semantic entity that is associated with a plurality of embeddings; when the query term corresponds to a semantic entity that is associated with a plurality of embeddings, generating a set of lists, each list containing semantic entities for each embedding of the plurality of embeddings, wherein a semantic entity is included in one or more of the lists based on a comparison of the one or more semantic association scores; and when the query term corresponds to a semantic entity that is associated with a plurality of embeddings, providing an output based on the set of lists.

According to some embodiments, the one or more corpora can include structured data and unstructured data.

According to some embodiments, the method can further include determining a set of measures that measure the occurrences of each meaning of the plurality of meanings of the multi-meaning semantic entity in the one or more corpora.

According to some embodiments, the measure can be a count of the number of co-occurrences, in one or more documents of the one or more corpora, of the particular meaning of the multi-meaning semantic entity with one or more of the semantic entities of the plurality of semantic entities.

According to some embodiments, the measure can be a count of documents of the one or more corpora in which the particular meaning of the multi-meaning semantic entity co-occurs with one or more of the semantic entities of the plurality of semantic entities.

According to some embodiments, the word embeddings can be generated using Adaptive Skip-gram (AdaGram).

According to some embodiments, the method further includes generating a percentage for each list in the set of lists, wherein the percentage for each list is calculated by dividing a number of semantic entities in the corresponding list by a total number of entities in all of the lists in the set.

According to some embodiments, the method can further include associating a semantic entity type with one or more lists in the set of lists by analyzing one or more semantic entity types associated with the semantic entities in the corresponding list.

According to some embodiments, the analyzing the one or more semantic entity types associated with the semantic entities in the corresponding list can include determining a semantic entity type that is most often associated with semantic entities in the corresponding list.

According to some embodiments, the output can enable a user device to display the set of lists and the resulting semantic entities in each list in the set of lists.

A method of generating semantic information between entities according to one embodiment of the present disclosure can include identifying a plurality of semantic entities in one or more corpora, wherein the semantic entities include one or more of single words or multi-word phrases; identifying a plurality of semantic entity types in the one or more corpora; associating at least one semantic entity type with the semantic entities of the plurality of semantic entities; generating word embeddings for the plurality of semantic entities; determining one or more semantic association scores between semantic entities from the plurality of semantic entities; receiving a query term and an entity type input; determining a query term entity type associated with the query term; generating a first list of resulting semantic entities associated with the query term based on the one or more semantic association scores, wherein the resulting semantic entities from the first list are associated with the same semantic entity type as the query term entity type; generating a second list of resulting semantic entities associated with the query term based on the one or more semantic association scores, wherein the resulting semantic entities from the second list are associated with the entity type input; generating a third list of semantic association scores, wherein the third list includes semantic association scores between each of the resulting semantic entities from the first list and each of the resulting semantic entities from the second list; and providing an output based on the first list, the second list, and the third list.

According to some embodiments, the one or more corpora can include structured data and unstructured data.

According to some embodiments, the plurality of semantic entity types can be identified based on one or more of: a structured database, a custom list of entity types, an output from a neural network, an output from supervised machine learning, or an output from unsupervised machine learning.

According to some embodiments, the neural network architecture can be one or more of: a recurrent neural network (RNN) or a Long Short Term Memory (LSTM).

According to some embodiments, the word embeddings can be generated using one or more of Word2vec, AdaGram, fastText, and Doc2vec.

According to some embodiments, the generating the first list can include limiting a number of the resulting semantic entities to a maximum count.

According to some embodiments, the generating the first list can be further based on requiring a semantic association score of each of the resulting semantic entities to be greater than a minimum semantic association score.

According to some embodiments, the generating the second list can include limiting a number of the resulting semantic entities to a maximum count.

According to some embodiments, the generating the second list can be further based on requiring a semantic association score of each of the resulting semantic entities to be greater than a minimum semantic association score.

According to some embodiments, the output can enable a user device to generate a heatmap with the resulting semantic entities from the first list on a y-axis, the resulting semantic entities from the second list on an x-axis, and each of the semantic association scores from the third list being represented as a color or a shade of a color, wherein the color or the shade of a color maps to a semantic association score.

A method according to one embodiment of the present disclosure can include identifying semantic entities and associated semantic collections present in one or more knowledge bases, wherein the semantic entities include one or more of single words or multi-word phrases, and the semantic entities of a semantic collection share an entity type; determining a time period for analysis; dividing the time period into one or more time slices; generating, for each time slice, a set of word embeddings for the identified semantic entities based on one or more corpora; characterizing a temporal semantic association between a first semantic entity input and a second semantic entity input by performing the steps of: determining, for each time slice, a first semantic association strength between the first semantic entity input and the second semantic entity input; determining, for each time slice, a second semantic association strength between the first semantic entity input and a plurality of semantic entities associated with a semantic collection that is associated with the second semantic entity; determining, for each time slice, a probability measure relating the first semantic association strength with the second semantic association strength; assigning a time value to each time slice; determining a sequence of two-dimensional points by associating, for each time slice, the assigned time value for the time slice with the probability measure for the time slice, wherein the sequence is ordered by increasing time values; fitting a curve to the ordered sequence; extracting characteristics of the curve fit, wherein the characteristics include one or more of: a time of increase value representing the time value at which a statistically significant magnitude change of the probability measure occurs, a probability saturation value representing the maximum value of the probability measure, or an area under the curve value; providing the characteristics of the curve fit from the characterizing the temporal semantic association between the first semantic entity input and the second semantic entity input.

According to some embodiments, the method can further include: receiving the first semantic entity input from a user; receiving the second semantic entity input from a user as a set of at least two second semantic entities; performing the steps of the characterizing the temporal semantic association between the first semantic entity input and the second semantic entity input for each of the second semantic entities of the set; and displaying the characteristics of the curve fits for the first semantic entity input and at least two of the second semantic entity inputs of the set.

According to some embodiments, the displaying the characteristics of the curve fits can include displaying the time of increase value, the probability saturation value, and the area under the curve value for each of the first semantic entity input and the second semantic entity input temporal semantic associations as a bubble plot, wherein a bubble placement along an x-axis of the bubble plot corresponds to the time of increase value, a bubble placement along a y-axis of the bubble plot corresponding to the probability of saturation value, and a size of a bubble corresponds to the area under the curve value.

According to some embodiments, the method can further include: displaying an identity of the first semantic entity input and an identity of the second semantic entity input associated with a bubble in proximity to the bubble.

According to some embodiments, the displaying the characteristics of the curve fits can include displaying only the characteristics of the curve fits for which the probability saturation value satisfies a probability threshold value.

According to some embodiments, the displaying the characteristics of the curve fits can include displaying only the characteristics of the curve fits for temporal semantic associations between first semantic entity inputs and second semantic entity inputs having a count of co-occurrence in documents of the one or more corpora that satisfy a co-occurrence threshold value.

According to some embodiments, the method can further include: determining a count of co-occurrence in documents of the one or more corpora of the first semantic entity input and at least two of the second semantic entity inputs of the set.

According to some embodiments, the displaying the characteristics of the curve fits can include displaying the time of increase value, the probability saturation value, and the count of co-occurrence for each of the first semantic entity input and the second semantic entity input temporal semantic associations as a bubble plot, wherein a bubble placement along an x-axis of the bubble plot corresponds to the time of increase value, a bubble placement along a y-axis of the bubble plot corresponding to the probability of saturation value, and a size of a bubble corresponds to the count of co-occurrence.

According to some embodiments, the probability measure relating the first semantic association strength with the second semantic association strength can be a negative logarithm of a p-value, wherein a relatively higher probability measure indicates the first semantic association strength is more statistically significant versus the second semantic association strength as compared to a relatively lower probability measure that indicates the first semantic association strength is not more statistically significant versus the second semantic association strength.

According to some embodiments, the fitting the curve to the ordered sequence can include fitting a sigmoid curve to the ordered sequence according to the equation:

$$y = \frac{K}{1+e^{-k(x-x_o)}} + c$$

where:
y values are the probability measures of the sequence; and
x values are the time values of the sequence.

According to some embodiments, any of the steps or actions disclosed herein can be performed by a server. In some embodiments, the server can include a memory that stores a module. In some embodiments, the server includes a processor configured to run the module stored in the memory that is configured to cause the processor to perform any of the steps or actions disclosed herein. According to some embodiments, a non-transitory computer readable medium can have executable instructions operable to cause a server to perform any of the steps or actions disclosed herein.

Any of the above embodiments or aspects can be combined with other embodiments and/or aspects set forth herein and remain within the scope of the invention.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

FIG. 2A illustrates one method of providing semantic responses to queries.

FIG. 3A illustrates one method of providing semantic responses to queries.

FIGS. 5A-B illustrate knowledge graphs that relate to diverse entities, as highlighted for the "neighborhoods" of the user-supplied exemplary queries in accordance with some embodiments of the present disclosure.

FIGS. 6A-6D illustrate examples showing how knowledge graphs relate diverse entities, as highlighted for the "analogies" in accordance with some embodiments of the present disclosure.

FIG. 9 illustrates output from a Bio-Knowledge graph queried for the exemplary phrase "Remyelination" followed by application of Entity Recognition techniques in accordance with some embodiments of the present disclosure.

FIGS. 52-56 illustrate neighborhood sense diagrams for the entity "Rho" that is associated with five different entity types in accordance with some embodiments of the present disclosure.

DETAILED DESCRIPTION

Figure 1:
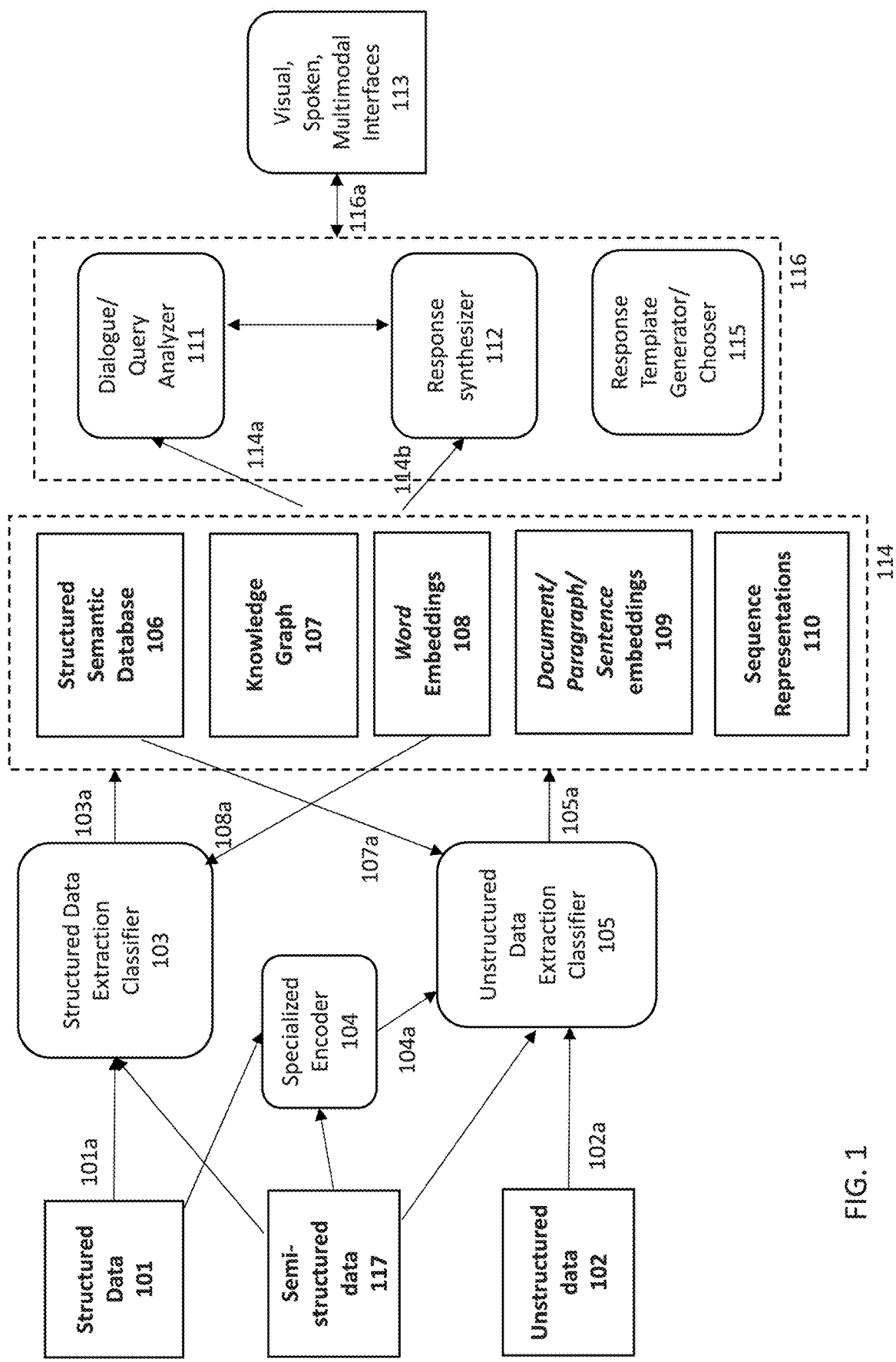
FIG. 1 illustrates a system architecture in accordance with some embodiments of the present disclosure.

Various other modifications and additions can be made to the exemplary embodiments discussed without departing from the scope of the present disclosure. For example, while the embodiments described above refer to particular features or particular steps, the scope of this disclosure also includes embodiments having different combinations of features or steps, and embodiments that do not include all of the above described features or steps.

The present disclosure describes systems, methods, and computer readable media to overcome many current challenges in generating synopsis/summary responses to user queries, particularly when the responses require semantic synthesis using structured and unstructured information from disparate sources. In some embodiments, neural networks and/or language models can be used to solve the following task, which at present, is virtually impossible to scale: visualization of semantic information that is inferred from structured and/or unstructured data, where, optionally, some or all of the data can be aggregated in real time from disparate sources.

Embodiments of the present disclosure can be applied to various industries and domains. However, for illustrative purposes, the present disclosure focuses on the healthcare/medical space. In some embodiments, the following terms can be used interchangeably: "entity" and "token." In some embodiments, the following terms can also be used interchangeably: "entity class" and "entity type." Moreover, in some embodiments, the following terms can be used interchangeably: "embeddings" and "vectors." Also, the phrase "word embeddings" is used to collectively refer to character, word, paragraph, sentence, and/or document embeddings, unless explicitly specified. In some embodiments, the following terms can be used interchangeably: "semantic association strength," "semantic association score," and "cosine distance."

Disclosed systems and methods can identify semantically related entities using word/document/paragraph/sentence embeddings generated from a corpus when the semantically related entities do not co-occur, where the embeddings can be generated using known techniques, but where terms/phrases are mapped to entities and entity classes. The similarity (e.g., distance between) in the mappings between each of the non-co-occurring entities and the entities and classes to which they are mapped enable the discovery of semantically related entities that are not present as co-occurring concepts in the original corpus. In other words, the similarity of a first mapping to a second mapping enables the discovery of the related entities in which the first entity mapping relates the first entity to a first set of entities and classes, and the second mapping relates the second entity to a second set of entities and classes.

Neural networks can be used to extract semantic information from unstructured data sources towards creating structured aggregates. In some embodiments, sequence models with state maintenance can be used within the neural networks for this purpose. In some embodiments, candidate data sets that can power spatial visualizations of data can be created with minimum human validation.

Disclosed systems and methods of synthesizing multidimensional summaries for search queries can include labeled entities and unlabeled terms/phrases. The search input can be one or more unlabeled entities. The search query can be terms/phrases or a natural language query that can include terms/phrases. The terms can be harvested from a sequence of queries as in a dialog exchange for disambiguation.

The labeled entities in the neighborhood of the search input can be used to create the orthogonal dimensions (e.g., rows and columns) of the synthesized summaries. The synthesizing can be performed by examining the entity distribution in the word/document/paragraph/sentence embedding neighborhood of the input terms/phrases and using that distribution to pick the candidate entities for the summary generation. The entity distribution, which captures entity/neighborhood relationships, can be a general distribution obtained from a universal corpus or a context specific distribution where context is inferred either implicitly or explicitly.

Language models using word vectors/embeddings (or character vectors composing word embedding) can be used—instead of traditional n-gram models, where words are atomic entities—to establish word embeddings as the de facto representation of words for machine learning models. Similar to the representation of words as vectors generalizing well beyond capturing mere co-occurrences, the representation of concepts and relationships between concepts as vectors can generalize beyond the explicit relationships encoded in the space from which they are extracted, facilitating the construction of a semantic knowledge graph with concept/relationship embeddings for broader and deeper understanding of data.

One or more disparate data sources can be aggregated by some embodiments into an exemplary "Core Corpus." For example, one or more data sources from the following table can be used:

| Resource |
| --- |
| Drugs@FDA |
| FDA Adverse Event Reporting System (FAERS) |
| Clinicaltrials.gov |
| Wikipedia & DBpedia |
| Pubmed |
| Compounds (NCI, Clinical trials, Drugbank, FDA, Pubchem) |
| Companies (Crunchbase, Linkedin, SBIR, Bloomberg) |
| Structured ontologies (Hugo, KEGG, MeSH, OMIM) |

According to some embodiments, the aggregation can be performed at various frequencies that can range from real time or substantially real time (e.g., through feeds) to any time period that is not real time or substantially real time (e.g., seconds, minutes, hours, days, weeks, months, years). In some embodiments, such a frequency can be based on each resource site's crawl frequency policy, where embodiments of the present disclosure can honor such a policy. In some embodiments, the frequency can be set differently for one or more of disparate data sources. In some embodiments, the frequency can be set either statically or dynamically.

In the healthcare/drug industry, each drug company can have a synopsis of its drugs in various stages of development. In some embodiments, an aggregated and/or synthesized semantic summary that can automatically cluster information, such as drug classes and disease categories, across different companies requires not only semantic understanding of entities pertaining to this space, but also gleaned and/or synthesized information from disparate structured and unstructured sources (e.g., structured company sites, quasi structured sites such as clinical trials, unstructured sources like Pubmed). In some embodiments, an aggregated and/or synthesized semantic summary can be created to improve the scalability and capability to address a broad class of semantic queries that can benefit users to make decisions quickly and eliminate the need to spend a long time (e.g., several hours spanning days if not weeks) to create such a synthesis from disparate structured and unstructured sources.

Embodiments of the present disclosure can also solve other challenges in extracting semantic information from disparate structured and unstructured sources. Examples of these challenges are described below.

First, there can be "entity class" inadequacy in human curated ontologies/information repositories to generate semantic responses to the wide range of user searches. While curated ontologies abound in healthcare industry, entities or entity classes can be missed, causing degenerate response of lexically matched results of user input to documents. For example, a search term, such as "remyelination," can degenerate to a lexical search response, unless a curated semantic result is constructed for the input. This is because remyelination is unlikely to be an entity that falls under typical entity types such as indications, diseases, drugs, etc. Even if the response of a word embedding neighborhood is used, this can still be inadequate because the neighborhood of an entity can be a mixed grab-bag of entity types. Although using the response of a word embedding neighborhood can be marginally better than the result generated from lexical responses, it would still not even be close to a result produced by embodiments of the present disclosure using a semantic synthesis that best matches user intent.

Second, disambiguation of entities can be required for certain terms. For example, a lexical search can produce a misleading result for the term "EGFR," which can stand for the gene "Epidermal Growth Factor Receptor" or the laboratory test "Estimated Glomerular Filtration Rate." This common user query can result in erroneous hits in purely lexical systems. In some embodiments, this problem can be solved by using a semantic bio-knowledge graph to implicitly disambiguate when context is present, or explicitly disambiguate the entity when no context is present.

Third, there can be a need to maximize the unambiguous recognition and classification of single word and multiword (phrase) entities in an unstructured source. The performance of named entity recognition from unstructured data using sequence learning neural net models (e.g., Recurrent Neural Net (RNN) variants in isolation or in combination with Conditional Random Fields (CRF)) can be lacking. In some embodiments, the performance leveraging off semantic similarities latent in word embedding, particularly from semantically related information sources, can be improved.

Fourth, there can be a need to extract specific semantic information of interest latent in a structured source. The organization of data in a structured repository may not lend itself to extracting semantic information across fields and keys in the structured repository. For example, FAERS (FDA Adverse Event Reporting System) includes structured information on adverse events and medication error reports. Popular measures that are computed from this repository do not capture some of the insightful latent information due to the organization of data.

Examples of data sources that are commonly used by various siloes of the pharmaceutical ecosystem and that can be used by embodiments of the present disclosure are described below.

Drugs@FDA (www.accessdata.fda.gov/scripts/cder/drugsatfda/): Drugs@FDA includes over 100,000 current FDA approved labels, older labels, approval letters, reviews (scientific analyses), and information for patients (1998-present). This largely unstructured knowledgebase includes all prescription and over-the-counter human drugs and therapeutic biologicals currently approved for sale in the United States, in addition to all discontinued drugs and Chemical Type 6 approvals. The following therapeutic biological products are included: monoclonal antibodies, cytokines, growth factors, enzymes, immunomodulators, thrombolytics, proteins intended for therapeutic use that are extracted from animals or microorganisms including recombinant versions of these products (except clotting factors), and non-vaccine therapeutic immunotherapies. The information in Drugs@FDA comes from both the FDA Orange Book (Approved Drug Products with Therapeutic Equivalence Evaluations) and the Center-wide Oracle-based Management Information System (COMIS) that maintains investigational new drug applications (INDs), new drug applications (NDAs), and abbreviated NDAs (ANDAs). Some embodiments of the present disclosure can also utilize the FDA's Structured Product Labeling (SPL) resource that includes information on approved products (www.fda.gov/ForIndustry/DataStandards/StructuredProductLabeling), such as dosage forms and drug classes (https://dailymed.nlm.nih.gov/dailymed).

Federal Adverse Event Reporting System (https://open.fda.gov/data/faers/): FDA Adverse Event Reporting System (FAERS) is a database of over 6.1 million reports that includes information on adverse events and medication errors submitted to the FDA. The database is designed to support the FDA's post-marketing safety surveillance program for drug and therapeutic biologic products. The largely semi-structured and structured FAERS database adheres to the international safety reporting guidance issued by the International Conference on Harmonisation (ICH E2B), with Adverse events and medication errors coded to terms in the Medical Dictionary for Regulatory Activities (MedDRA) terminology. The FAERS includes adverse event reports from healthcare professionals (such as physicians, pharmacists, nurses and others), consumers (such as patients, family members, lawyers and others), and product manufacturers as specified by FDA regulations.

Clinicaltrials.gov (https://clinicaltrials.gov/): ClinicalTrials.gov is a web-based resource that provides landing pages for 220,000+ clinical trials being conducted, completed, or terminated across all 50 states of the United States and 192 countries. These largely unstructured and semi-structured resource includes information on publicly and privately supported clinical studies on a wide range of diseases and conditions. The resource is maintained by the National Library of Medicine (NLM) at the National Institutes of Health (NIH). The Information is provided and updated by the sponsor of the clinical trial, or the principal investigator (PI) of the clinical study. Studies are generally submitted when they begin (register), and the information on the site is updated throughout the study. In some cases, results of the study are also included after the study ends, also in the form of unstructured text and semi-structured tables. Each ClinicalTrials.gov record presents summary information about a study protocol and includes the following: Disease or condition; Intervention (for example, the medical product, behavior, or procedure being studied); Title, description, and design of the study; Requirements for participation (eligibility criteria); Locations where the study is being conducted; Contact information for the study locations; Links to relevant information on other health Web sites, such as NLM's MedlinePlus for patient health information and PubMed for citations and abstracts of scholarly articles in the field of medicine. Some records also include information on the results of the study, such as the following: description of study participants (the number of participants starting and completing the study and their demographic data); outcomes of the study; and summary of adverse events experienced by study participants. The full history of the changes made to any clinical trial record are available via the ClinicalTrials.gov archive.

EDGAR—SEC Filings (www.sec.gov/edgar/searchedgar/companysearch.html): The Electronic Data Gathering, Analysis, and Retrieval (EDGAR) system provides 21 million filings required by the U.S. Securities and Exchange Commission (SEC). The EDGAR performs automated collection, validation, indexing, acceptance, and forwarding of all submissions by companies and other entities. Actual annual reports to shareholders (except in the case of mutual fund companies) need not be submitted on EDGAR, although some companies do so voluntarily. However, the annual report on Form 10-K or Form 10-KSB, which contains much of the same information, is required to be filed on EDGAR. There are over 3000 filings every day on the EDGAR database available in a largely unstructured and semi-structured form.

Wikipedia & DBpedia (www.wikipedia/org/ and http://wiki.dbpedia.org/): Wikipedia is a web-based, free-content, openly-editable Encyclopedia with about 5M+ English articles contributed by about 70,000+ active contributors. DBpedia is a crowd-sourced community effort to extract structured information from Wikipedia. The DBpedia knowledgebase describes about 4.58 million things, out of which about 4.22 million are classified in a consistent ontology, including about 1,445,000 persons, about 735,000 places, about 411,000 creative works, about 241,000 organizations (including about 58,000 companies and about 49,000 educational institutions), about 251,000 species, and about 6,000 diseases.

Pubmed abstracts (www.ncbi.nlm.nih.gov/pubmed/): PubMed includes more than 26 million citations for biomedical literature from MEDLINE, life science journals, and online books. Citations may include links to full-text content from PubMed Central and publisher web sites. This includes structured abstracts (www.nlm.nih.gov/bsd/policy/structured_abstracts.html) that use the IMRAD format (Introduction, Methods, Results, and Discussion) for scientific studies and the CONSORT (Consolidated Standards of Reporting Trials) format for randomized controlled trials (RCTs).

Compounds and drug entities: NCI—http://www.cancer.gov/; Clinicaltrials.gov—https://clinicaltrials.gov/; Drugbank—http://www.drugbank.ca/; FDA—http://www.fda.gov/; Pubchem —https://pubchem.ncbi.nlm.nih.gov/.

Companies: Crunchbase—www.crunchbase.com/; Linkedin—https://www.linkedin.com/; SBIR—https://www/sbir.gov/; Bloomberg—https://www.bloomberg.com/.

Human-curated ontologies: Hugo—http://www.genenames.orgs/; KEGG—http://www.genome.jp/kegg/kegg1.html; MeSH—http://www.ncbi.nlm.nih.gov/mesh; OMIM—http://www.omim.org/.

Figure 8:
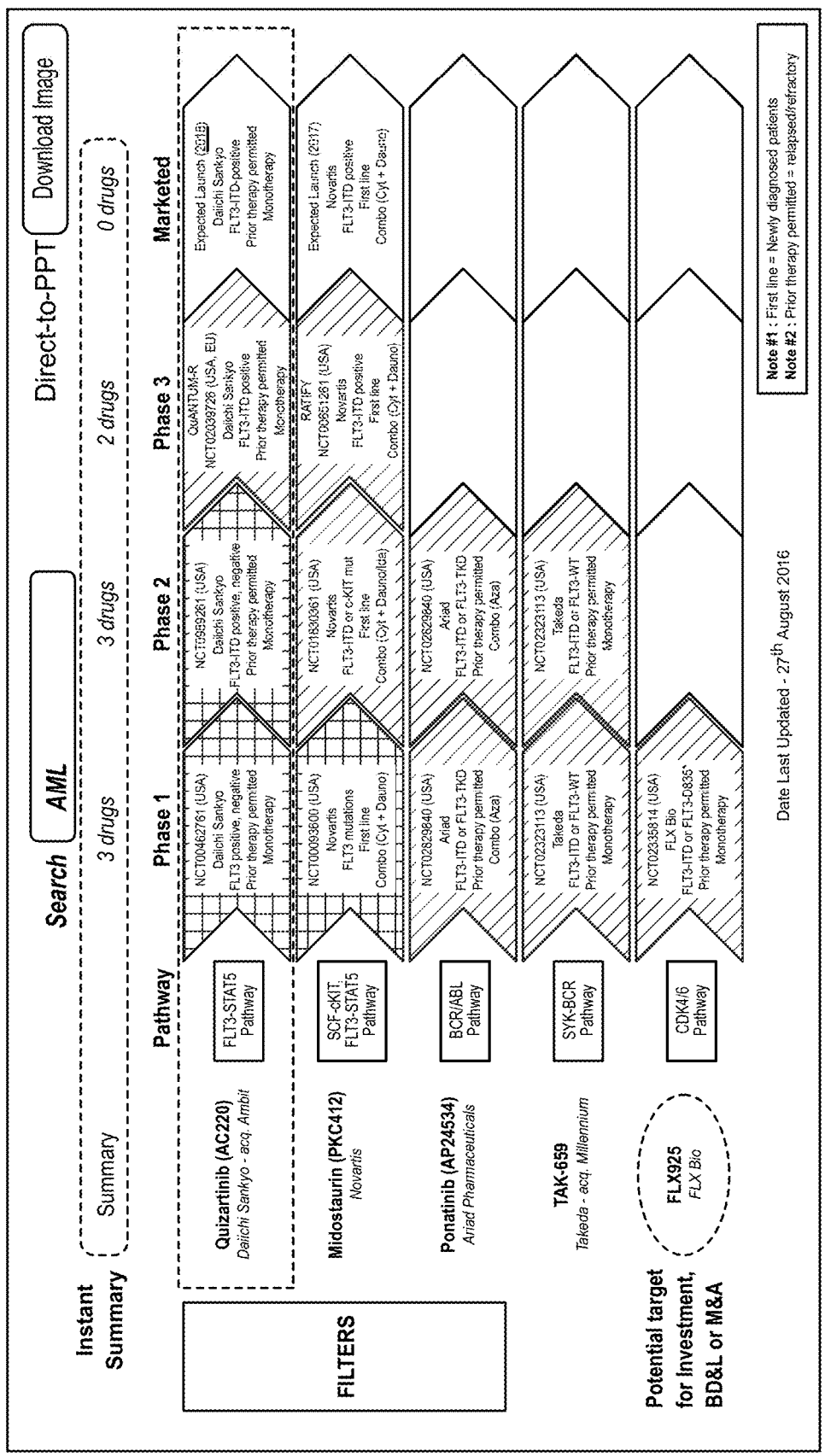
FIG. 8 illustrates a two dimensional matrix of data generated by the response synthesizer 112 (FIG. 1) in accordance with some embodiments of the present disclosure.

In some embodiments, a semantic search system can provide "summary answers" to a range of queries about the "temporal status" of drug or therapeutic entities. The temporal status can indicate the stage of development (e.g., preclinical, phase 1, phase 2, phase 3, marketed) of the drug. In some embodiments, the temporal status can be automatically mapped to an "entity" and/or "intersection of one or more entities" in a semantic bio-knowledge graph (e.g., as shown in FIG. 8). Non-limiting examples of entities can include: drug (e.g., Gleevec), company/organization (e.g., Roche, Dana Farber), indication (e.g., Non Small Cell Lung Cancer), phenotype (e.g., Remyelination, Angiogenesis), bio-molecular features including gene mutation (e.g., EGFR T790M in Lung cancer tumor), RNA or protein expression (e.g., PD-L1 overexpression in cancerous tumors; PLP1 in the demyelinating rare neurological disease PMD), signaling pathway (e.g., JAK/STAT pathway in blood cancer and autoimmune diseases such as Rheumatoid Arthritis), gene fusion (e.g., BCR/ABL fusion or Philadelphia Chromosome in Leukemia), Copy Number Alterations (e.g., BRCA in breast cancer, APC in colorectal cancer), and "therapeutic modality" (e.g., small molecule, antibody, immunotherapy, gene therapy, radiation therapy).

FIG. 1 illustrates a system architecture in accordance with some embodiments of the present disclosure. Embodiments of the present disclosure can advantageously extract key data prerequisites (e.g., entities, their attributes, entity types, logical and temporal sequence relationships) from different pathways (e.g., 101a and 102a) and consolidate the key data prerequisites in the system store 114 with the pathways taking advantage of the other. By using these extraction and consolidation methods, embodiments of the present disclosure can automate synthetic responses.

Information can generally be scattered across both structured and unstructured data. For example, temporal sequence of drugs administered as first line and second line therapies are embedded in sentences in clinical trials. Embodiments of the present disclosure can obviate the need to manually read through the sentences in clinical trials to construct temporal sequences.

Input data to the system can be structured data 101, semi-structured data 117, and/or unstructured data 102. In some embodiments, structured data 101 can be in the form of entity tuples. For example, structured data can include a key-value tuple, where the key is "disease" and the value is "cancer." In some embodiments, unstructured data 102 can include information in the form of phrases or sentences. For example, unstructured data can include the phrase "I have Parkinson's disease and I took drug X." In some embodiments, semi-structured data 117 can include both structured data and unstructured data. For example, semi-structured data can be hierarchical/flat structure of key/value tuples, where some of the values are unstructured.

In some embodiments, structured data 101 can pass through 101a to a structured data extraction classifier 103 that can identify entity types and their attributes (entities) unambiguously with available context. For example, if the structured data is "disease=cancer," the structured data extraction classifier 103 can identify that the entity type is "disease" and that the entity is "cancer." In some embodiments, the structured data classifier 103 can use a supervised learning model, such as a Support Vector Machine (SVM). The structured data extraction classifier 103 can store (103a) the extracted data in a system store 114. In some embodiments, the output of the structured data extraction classifier 103 can be entity types, entities, and the entity types' relationships to other entity types.

An entity type of an entity can be identified in various other ways. In some embodiments, an entity type of an entity can be identified based on a sequence model. For example, LSTM can be used. The sequence model can be trained on a particular corpus to learn the context in which words arise. Thus, the sequence model can uncover the context in which entities that presently are unassociated with an entity type arise. This enables an entity type to be associated with an entity, when an entity type is sought for the entity. Other suitable models for machine learning can also be used to uncover the context in which entities arise.

In some embodiments, neighbors of an entity can be used to identify the entity's entity type based on the neighbors' entity types. In some embodiments, the neighbors can be defined as other entities that are closely related—in terms of their cosine distances—to the entity. In some embodiments, a specific number of neighbors can be selected, and a weight can be assigned to each of the selected neighbors. For example, to associate an entity type with an entity, the entity's neighbors can be ranked based on their cosine distance from the entity, and the top 500 neighbors can be considered. Each of the 500 neighbors can be assigned a weight, such as a percentage weight, which can vary based on their rank. For instance, the first-ranked neighbor can be assigned a weight of 1%, the second-ranked neighbor can be assigned a weight of 0.9%, the third-ranked neighbor can be assigned a weight of 0.87%, and so on. In some embodiments, the decreasing rate of the weight can be based on an exponential decay function. In some embodiments, all the neighbors can be considered without any limit. In some embodiments, the amount of the weight can be directly proportional to the value of the cosine distance. In some embodiments, the amount of the weight can be directly proportional to the value of the rank. In some cases, such assignment of weights can be referred to as "continuous decay," because the weight continuously decreases as the rank moves towards the bottom. After the weights have been assigned, the neighbors' entity types can be examined and grouped by the same entity types. For each entity type, a sum of the percentage weights of the neighbors for that entity type can be calculated and assigned to that entity type. For example, if the entity type X is associated with three neighbors with three percentage weights (0.5%, 0.3%, and 0.1%), then X is assigned a percentage of 0.9%. In some embodiments, this percentage can indicate the probability of the entity being that entity type. In some embodiments, the system can associate an entity with an entity type if such a percentage exceeds a certain threshold number. In some embodiments, the system can associate an entity with an entity type with the highest percentage.

In some embodiments, instead of assigning varying weights to the neighbors, each neighbor can be assigned the same weight. For example, if the top 100 neighbors can be picked, and each neighbor can be assigned 1% as its weight.

In this case, even if neighbors have different cosine distances, they are treated the same when weights are assigned.

In some embodiments, unstructured data 102 can pass through 102a to an unstructured data extraction classifier 105. The output of the unstructured data extraction classifier 105 can store (105a) the extracted data in the system store 114. In some embodiments, the unstructured data extraction classifier 105 can use a class of artificial neural network (ANN) (e.g., a recurrent neural network (RNN)) and/or a word embedding generator.

In some embodiments, when there is latent information that can be extracted from structured data 101, a specialized encoder 104 can be used to generate unstructured data from the structured data 101. The specialized encoder 104 can send (104a) the generated unstructured data to the unstructured data extraction classifier 105, which can in turn send the output through the unstructured data extraction pathway 105a. In some embodiments, the generated unstructured data is in the form of unstructured text. For example, if the structured data is "disease=cancer; indication=weight loss; drug=methotrexate; side_effect=dizziness," the specialized encoder 104 can generate unstructured data in the form of "disease cancer indication weight loss drug methotrexate side_effect dizziness." In this example, latent information in the structured data can be that cancer can be associated with weight loss and methotrexate and that the patient suffers dizziness. Thus, such latent information can be extracted and leveraged by using the unstructured data extraction classifier 105 on the structured data 101 that has been processed by specialized encoder 104. In some embodiments, a part of structured data 101 can be processed using the specialized encoder 104. In other embodiments, the entire structured data 101 can be processed using the specialized encoder 104. In another example, the specialized encoder 104 can generate unstructured data by using the entities labels to position the entities in a given proximity. For example, given the same set of structure data, the specialized encoder 104 can apply a mapping of "drug disease drug indication drug side effect" to create the unstructured text of "methotrexate cancer methotrexate weight loss methotrexate dizziness".

In some embodiments, the structured data portion of the semi-structured data 117 can be passed to the structured data extraction classifier 103. In some embodiments, the unstructured data portion of the semi-structured data 117 can be passed to the unstructured data extraction classifier 105. In some embodiments, a part or the entire structured data portion of the semi-structured data 117 can be passed to the specialized encoder 104, which can send the output to the unstructured data extraction classifier 105.

In some embodiments, the output of the unstructured data extraction classifier 105 can include an entity type, entity, document/paragraph/sentence embeddings, entity relationships including temporal/logical sequence relationships, and sequence representations. In some embodiments, entities can be either labeled or unlabeled. A label can be used to describe an entity. For example, the entity "EGFR" can refer to "Epidermal Growth Factor Receptor," in which case the entity "EGFR" can be labelled as a gene. Without a label, there may be ambiguity as to what an entity may refer to. For example, if the entity "EGFR" is not labelled, "EGFR" can be ambiguous because "EGFR" can refer to the gene "Epidermal Growth Factor Receptor" or the laboratory test "Estimated Glomerular Filtration Rate." Entities can be labeled using various techniques. For example, a search (e.g., using Google) can produce a label for an entity. As another example, a corpus can provide labels. Wikipedia, for example, can provide labels for certain entities on many of its pages. For unstructured data, context surrounding entities can be analyzed to determine their labels. In some embodiments, a class of ANN (e.g., an RNN) can be used to perform such analysis. In some embodiments, the analysis performed using the ANN can be improved by leveraging systems and methods described below in connection with FIGS. 8 and 9.

In some embodiments, the system store 114 can capture information extracted from two or more source paths (e.g., 103a and 105a) in different forms to facilitate the synthesis of information and/or enable subsequent information extraction through different pathways (e.g., pathways 103a and 105a). The system store 114 can include information stored in a structured semantic database 106 (which can be a traditional database); a knowledge graph(s) 107 (which can be directed graphs of labeled (extracted from both paths 101a and 102a) and/or unlabeled entities (extracted from the 102a path)); word embeddings 108 (which can include word(s) and/or sentence(s)); document/paragraph/sentence embeddings 109; and sequence representations of unstructured data 110. In some embodiments, an example of word embedding can be word2vec. In some embodiments, an example of document/paragraph/sentence embedding can be doc2vec. In some embodiments, an example of sequence representations 110 can be Memory Neural Network (MemNN). In some embodiments, MemNN can be used for "Question and Answer" style discovery, where MemNN can be trained on questions to generate responses/follow-up questions. In some embodiments, these responses and/or follow-up questions can be used in case of ambiguity. For example, there may be ambiguity as to what an entity may refer to.

In some embodiments, the word embeddings 108 and/or document/paragraph/sentence embeddings 109 can be repositories of embeddings generated for a broad class of domain specific corpus. In some embodiments, these embeddings can capture one or more relationships of labeled and unlabeled entities in that domain. In some embodiments, these embeddings can be used to indicate and/or rank the strength of such relationships.

The embeddings can be used to construct one or more of knowledge graphs 107. The knowledge graph 107 can be representative of a universal graph, domain, and/or context specific graphs with labeled and/or unlabeled nodes having universal/domain/context specific weights. The corpus can determine the embeddings and in turn the neighborhood nodes in the graph. Sequence representations 110 can be a repository of universal, domain, and/or context specific sequences, and can be used to comprehend and respond to questions spanning multiple sentences/questions.

The system store 114 can serve to synthesize responses and facilitate subsequent information extraction through both pathways 107a and 108a. For example, the word embeddings 108 can be used to eliminate spurious information that can present in structured data. In some embodiments, if an entity is found in a structured record, and the entity is not semantically related to the other entities in the record, which can be revealed through word embedding neighborhood metrics, then that information can be passed (108a) to the structured data extraction classifier 103, and that entity can be isolated for manual verification. The structured database pathway 107a can be used to improve the named entity labeling scores. In some embodiments, the named entity labeling scores can be associated with the confidence score of labeling a term/phrase. In some embodiments, the structured semantic database 106 can be used to validate and/or confirm the entity type of a term/phrase; this can help improve the named entity labeling scores and can increase the confidence score of labeling a term/phrase.

The system store 114 can power a discrimination engine 116 that can include a dialog/query analyzer 111 (which can rely largely on sequence representations 110), a response synthesizer 112, and a response templates generator/chooser 115. The response template generator/chooser 115 can power user interfaces 113 through 116a. In some embodiments, the dialog/query analyzer 111 can analyze user input, such as a search term and filter criterion. For example, if a user searches the term "AML" on an interface (e.g., the interface in FIG. 8), the dialog/query analyzer 111 can receive and analyze this search term, and pass the search term to the response synthesizer 112 for further processing. In some embodiments, the dialog/query analyzer 111 can receive data from the system store 114 through 114a for the analysis function. The response synthesizer 112 can also receive data from the system store 114 through 114b, and use this data to synthesize responses that are relevant for producing results for the user's search action.

The response template generator/chooser 115 can generate/choose an appropriate template to be used for presenting search results to the user through an interface. Different types of templates can be used to generate different types of bio-knowledge graphs, such as the bull's eye bio-knowledge graph in FIG. 7 and the pipeline bio-knowledge graph in FIG. 8. In some embodiments, the response template generator/chooser 115 can generate a template based on the labels for the entities that are being presented on an interface. These entities can be selected based on their entity distribution. In some embodiments, the response template generator/chooser 115 can choose a template from a set of hard-coded templates. In some embodiments, a hard-coded template can be generated through training (e.g., a system can generate a template by learning certain types of entities and their labels from a corpus). In other embodiments, a hard-coded template can be manually generated. In some embodiments, a user can override a portion or all of the view in an automatically chosen/generated template. For example, a user can replace the drug information with the indication information by using filters.

Various components that are part of the system 100 can be implemented as hardware, software, or combinations of both. Various components and blocks described herein can be arranged differently (for example, arranged in a different order, or partitioned/combined in a different way) all without departing from the scope of the subject technology.

According to some embodiments, one or more computations by the system in FIG. 1 can be performed by one or more processors in a cloud system. In some embodiments, any rendering of output (e.g., rendering of user interface) can be performed by a user device (e.g., a personal computer, a mobile device, etc.). In some embodiments, any input to the system in FIG. 1 can be made by a inputting system that can involve hardware and/or software (e.g., a keypad, a keyboard, a microphone, speech recognition software, etc.). In some embodiments, a database (e.g., the structured semantic database 106) used in the system in FIG. 1 can be from any source, such as a relational database, NoSQL DB, flat files, and/or any other suitable database. In some embodiments, the database can be a local database and/or a remote database.

FIG. 2A illustrates one method of providing semantic responses to queries. A search engine, such as Google, can be used to find information on the search term "aml."

Figure 2B:
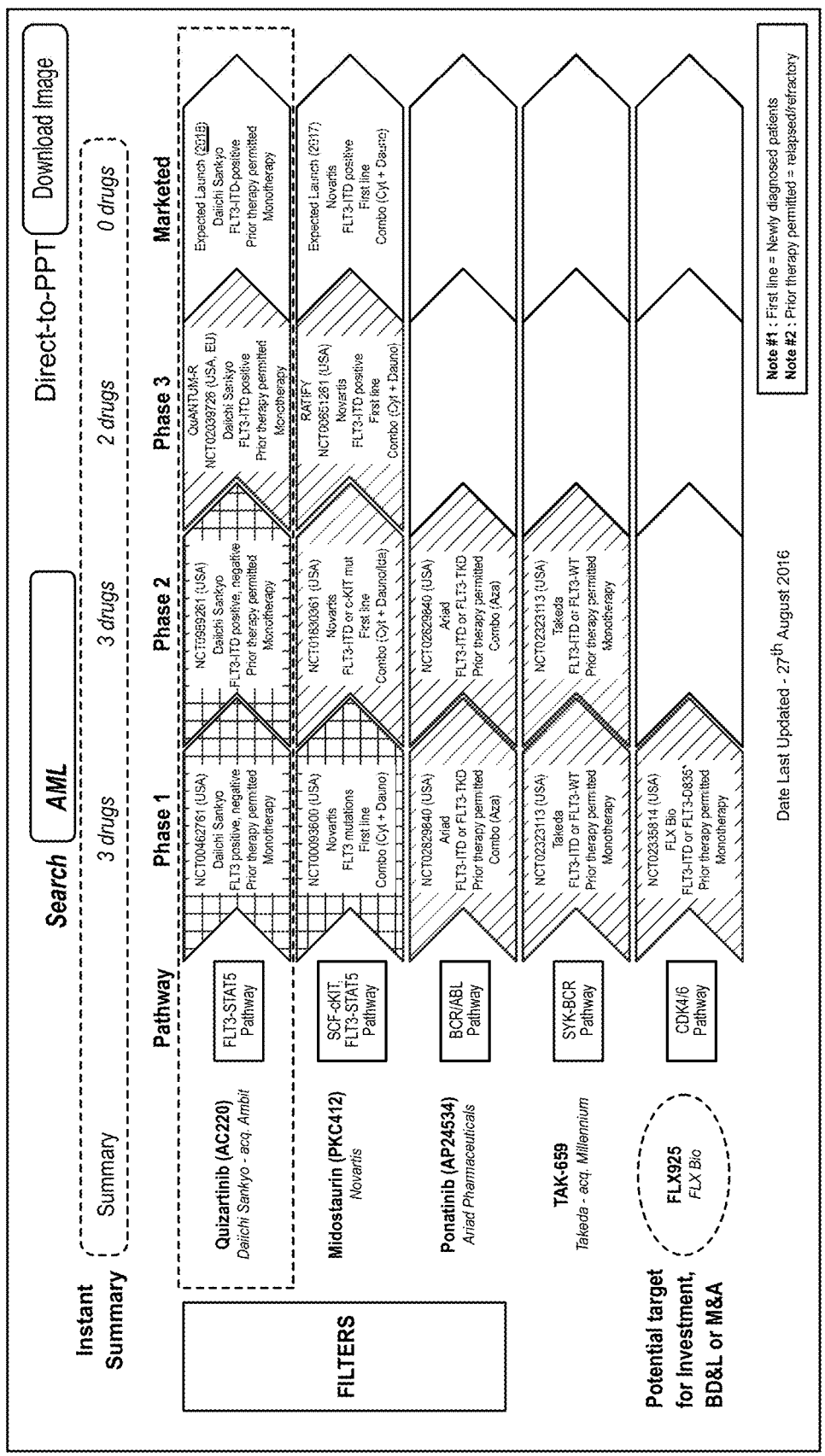
FIG. 2B illustrates a rendition of an interface enabled by synthesizing data from multiple pathways in accordance with some embodiments of the present disclosure.

FIG. 2B illustrates a rendition of an interface enabled by synthesizing data from multiple pathways in accordance with some embodiments of the present disclosure. In some embodiments, these pathways can be 101a and 102a from FIG. 1.

Figure 3B:
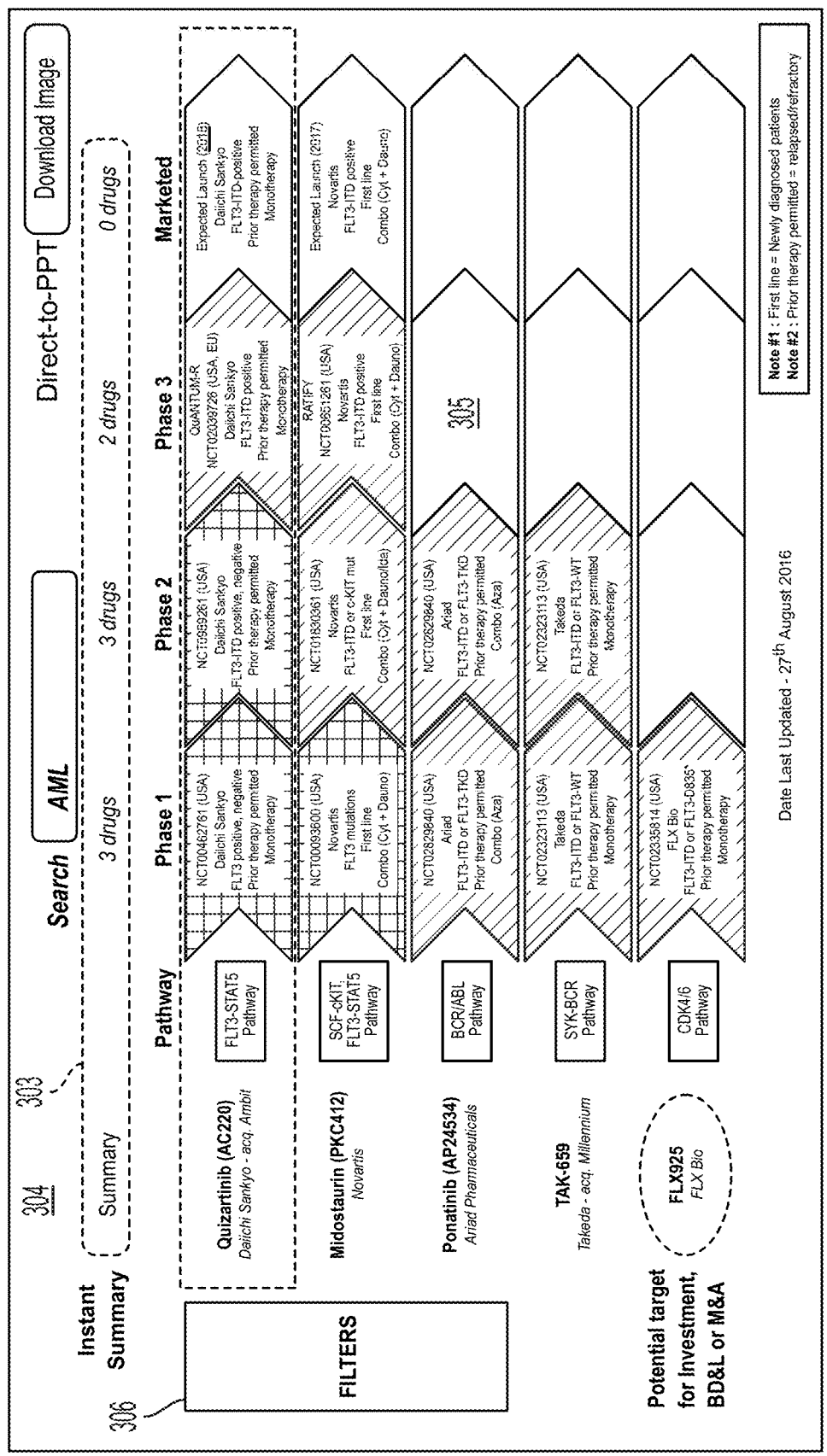
FIG. 3B illustrates a rendition of an interface enabled by synthesizing data from multiple pathways in accordance with some embodiments of the present disclosure.

FIG. 3A illustrates one method of providing semantic responses to queries. FIG. 3B illustrates a rendition of an interface enabled by synthesizing data from multiple pathways in accordance with some embodiments of the present disclosure. In FIG. 3A, the user interface is powered by a search index of documents 301 with an information box 302 of attributes for the search input "AML." Additionally, a set of questions semantically related to search terms is present in the backend driving the interface. In contrast, in FIG. 3B, the user interface can have rich semantic information. For example, the user interface may not have the search term "AML" present anywhere in the result. Even from a cursory glance, one can view that there are no results matching the search term "AML." In some embodiments, the synthesized data powering the interface can be a matrix of rows and columns, where the first column 303 and second column 304 are entities (in this example, the first column includes information related to drugs and their associated companies; and the second column includes information related to pathways) that can relate to the user input "AML." The subsequent columns can form a temporal sequence, where each column relates to a different phase of the drug development.

Figure 4:
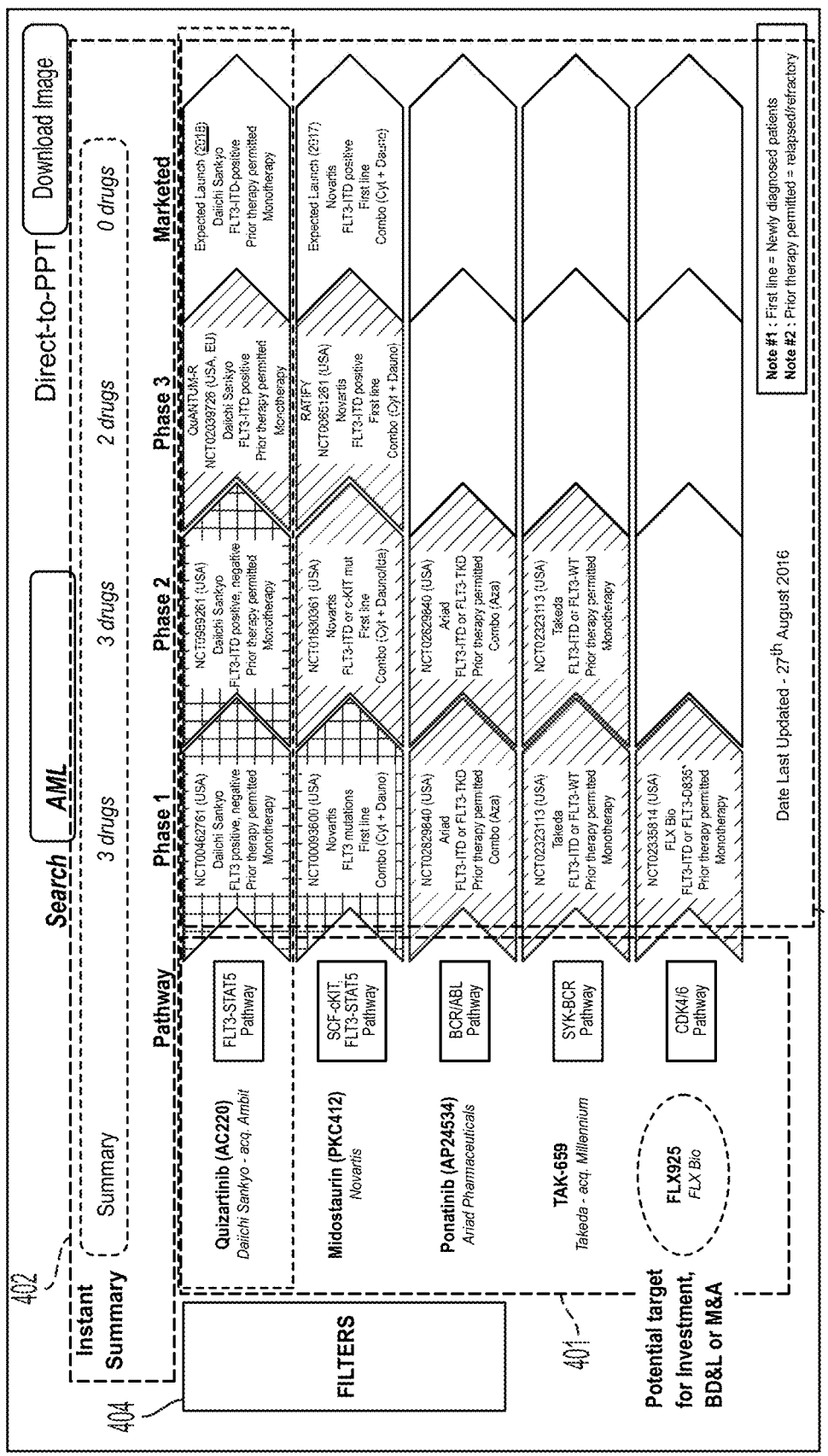
FIG. 4 illustrates a two dimensional matrix of data generated by the response synthesizer 112 (FIG. 1) in accordance with some embodiments of the present disclosure.

FIG. 4 illustrates an example two-dimensional matrix of data generated by the response synthesizer 112 (FIG. 1) in accordance with some embodiments of the present disclosure. This example two-dimensional matrix of data shows a response to the user input "AML," where the following items are shown: entities 401 (drugs+companies, pathways), temporal sequence of entities 403 (drugs in various stages of development), summary 402, and a matrix transform control 404 that can include semantic filters and transforms of data. The intent determination can be performed by query analyzer 111 (FIG. 1) that can result in the synthesis of the response making use of the response template chooser 115 (FIG. 1). In some embodiments, the template chooser/generator 115 can be trained by a neural network (e.g., a convolutional/RNN combination) to generate the appropriate response template involving entities and entity sequences.

In some embodiments, components that are supervised learning systems can have user sampling and validation including manual overrides. Even if the amount of labeled data to train a template chooser/generator 115 is initially low (e.g., for a specific domain and the system may memorize), such a system can scale better than a hand-engineered rules driven template system, where the availability of more labeled data (use cases) can cause the system to become more brittle. In neural nets, when the number of parameters in the network is large and the training data is small, the system can perform a close fit on the training data, given the large number of parameters. This is known as over-fitting. Overfitting can be like memorizing the trained data. This does not necessarily imply that it can generalize well beyond the training data. The response in FIG. 4 is shown in a two dimensional space for illustrative purposes. In some embodiments, embodiments of the present disclosure can power an interface with any number of dimensions, including a single dimension and more than two dimensions.

In the current state of art, a user interface is often powered from behind by a database view, where the data for the view is curated upfront with select labeled entities. In contrast, embodiments of the present invention, as illustrated in FIG. 4, enable a rich semantic response to be automatically synthesized dynamically, even when the input query includes unlabeled entities (e.g., remyelination, "elaborate on remyelination"). In some embodiments, the rich semantic response can be synthesized by (1) examining the entity distribution around the input terms based on the context of the query, where entity distributions can vary around a term within a corpus and/or between different corpora (e.g., FIG. 9 shows entity distribution for the term "remyelination"); (2) identifying candidate entities and entity sequences to construct the response; (3) creating the summary based on the identified candidate entities and entity sequences; and (4) choosing transforms appropriate to the chosen candidate entity and entity sequences.

Furthermore, the system components described in the present disclosure can learn either supervised, unsupervised, or semi supervised, from structured and unstructured data.

Systems and methods in accordance with embodiments of the present disclosure can address various challenges—examples of which are discussed directly below—in synthesizing semantic response to user queries.

An example challenge can be when a user makes a query that is not a labeled entity or entity class (e.g., remyelination). In this case, the knowledge graph (which includes both labeled and unlabeled entities) can facilitate finding labeled entities related to the user input by scanning its neighborhood. In addition, the classification of the labeled entities (e.g., genes, drugs, indications, companies etc.) can enable computation of an entity distribution (e.g., FIG. 9) to facilitate the choice of most relevant semantic rendition of this entity. This approach addresses the entity class inadequacy problem described above, where the current state of art systems would output just lexically matching results or just the entities in the neighborhood of word embedding for the unlabeled entity.

Another example challenge is that although word, document/paragraph/sentence embeddings have the inherent property of bringing semantically related entities together even if they do not co-occur in the corpus, these entities are difficult to discover from the embeddings.

Embodiments of the present disclosure can construct a knowledge graph by combining semantic relationships with labeled entities and/or entity classes. This can enable innovative insights to be unearthed, where those insights are not described as a co-occurrence in the primary literature. For example, the word "riluzole" (an ALS drug) and the word "vemurafenib" (a melanoma drug) are proximal to each other, as indicated by their cosine distance which can be about 0.48. The cosine distance is found to be significant as these two words are found in the context of treating a cancer, and thus, there is an overlap in the context, where these words are found. However, the proximate co-occurrence of the words "riluzole" and "vemurafenib" does not occur in any primary literature consumed. For example, a Google search shows no document containing these two words within a five word window proximity. In some embodiments, novel insights can emerge from a system that can show a relationship between words such as "riluzole" and "vemurafenib." These insights can lend themselves to effective generation of R&D hypothesis, clinical trial design, and commercial decisions. In some embodiments, visualization of these related entities can involve a mechanism that distinguishes these neighborhood entities from others that appear only because of physical proximity to the original term in document. An example can be seen in FIG. 11. In other words, and as described in more detail below, the relationship between the entities "riluzole" and "vemurafenib" is not discovered due to their proximity in the corpus. Rather, it is the similarity of the characterizations of those entities (e.g., by comparing the cosine distance of their vectors) based on an analysis of the entire corpus that uncovers the otherwise hidden relationship.

In some embodiments, the knowledge graph created from unstructured and structured sources can be used to create entity specific centroids (e.g., use all or some of the entities pertaining to a context) and use the synthesized centroids to validate the labeling of entities generated by a sequence learning model, such as bidirectional LSTM (Long short-term memory) RNN. The semantic bio-knowledge graph can be used to constrain the context in which a specific document has to be interpreted; this can help filter out a lot of "noise" from generic databases (e.g., considering a database of all HUGO genes).

In some embodiments, the key/value fields from a structured source are processed through a specialized encoder that may create a unstructured stream that can be fed to a learning model to generate word embeddings that reveal latent semantic relationships in structured data.

In some embodiments, the knowledge graph with labeled entities can be directly used to identify entities and generate responses. The knowledge graph can relate diverse entities, as highlighted for exemplary "neighborhood" (FIGS. 5A-5B) and "analogy" case studies (FIGS. 6A-6D). In some embodiments, the knowledge graph can include a collection of (1) an aggregate computer system housing all labeled and unlabeled entities, (2) entity specific computer systems, and (3) an unlabeled computer system houses all terms or phrases that are not labeled as entities.

Figure 5B:
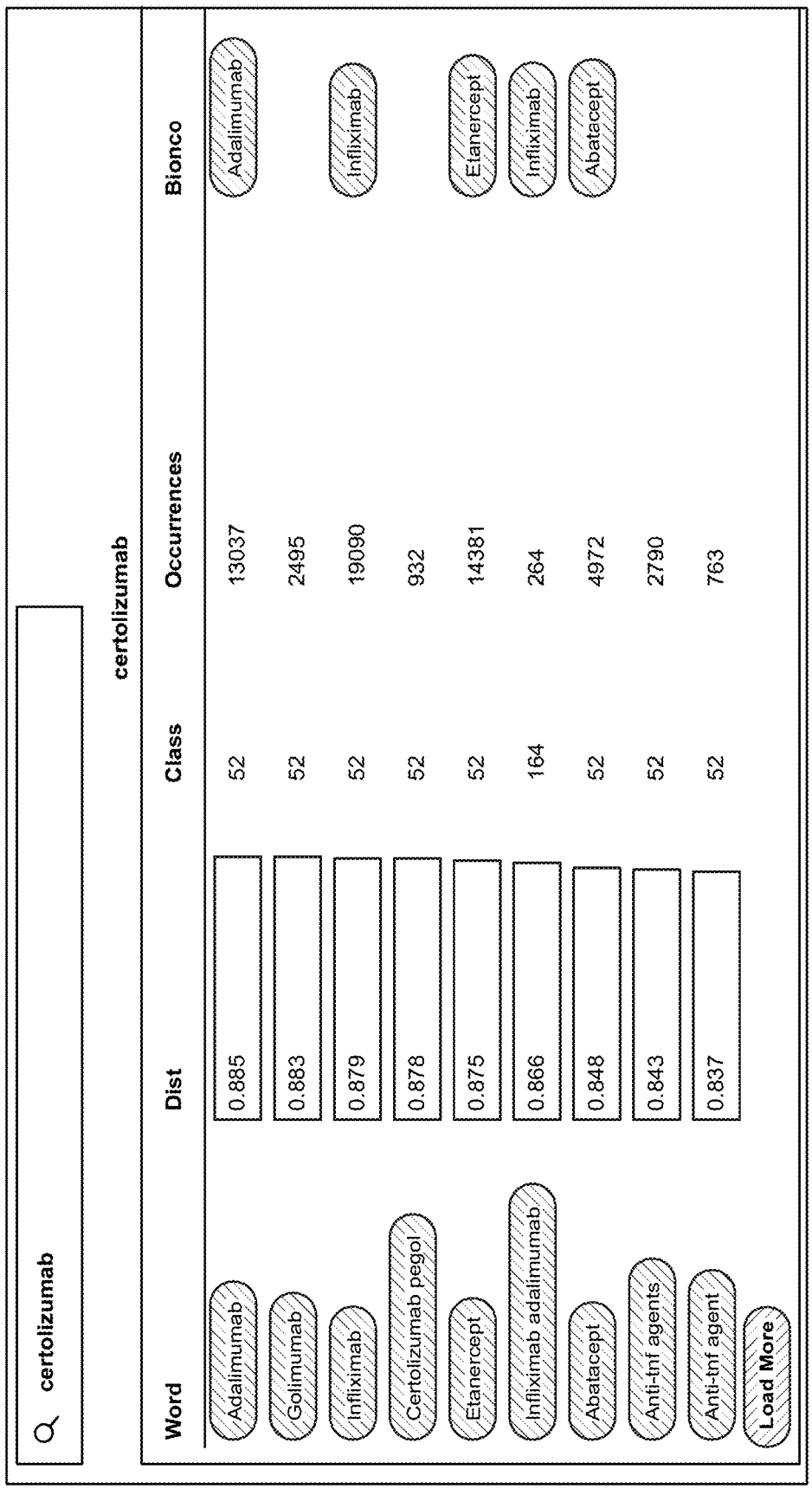

FIGS. 5A-B illustrate knowledge graphs that relate to diverse entities, as highlighted for the "neighborhoods" of the user-supplied exemplary queries in accordance with some embodiments of the present disclosure. The user-supplied exemplary queries are "Lacosamide" and "Certolizumab" respectively for FIG. 5A and FIG. 5B. These knowledge graphs can show how a system can function on a corpus (e.g., the "Core Corpus").

FIGS. 6A-6D illustrate examples showing how knowledge graphs relate diverse entities, as highlighted for the "analogies" in accordance with some embodiments of the present disclosure. In some embodiments, the knowledge graph includes labeled (word/document/paragraph/sentence embeddings with entities/entity classes assigned) and unlabeled entities.

FIG. 6A illustrates example #1, where "anti-EGFR:Erlotinib::infliximab:?" (using the well-known format of A:B::C:?, meaning A is to B as C is to?) exists and the top hits include anti-TNF which is the target of infliximab. FIG. 6B illustrates example #2, where "T315I:Ponatinib::CO-1686:?" exists and the top hits include T790M which is the genotype of CO-1686/Rociletinib. FIG. 6C illustrates example #3, where "Arthritis:Certolizumab::Rotigotine:?" exists and the top hits include parkinsonism which is the disease indication that Rotigotine is FDA-approved to treat. FIG. 6D illustrates example #4, where "Zyrtec:Allergy::Hypercholesterolemia:?" exists and the top hits include Rosuvastatin which is FDA-approved to treat Hypercholesterolemia.

In some embodiments, the revealed semantic relationships can help automate workflows for critical commercial, clinical, and R&D functionalities in pharmaceutics. An example is the generation of strategic insights into the landscape of complex diseases via an Orphan+Rare disease lens towards helping users identify high-value investment white-spaces. A related use case can be the generation of on-demand, powerful visual snapshots of the competitive clinical investment landscape towards supporting data-driven commercial and clinical strategy.

In some embodiments, one exemplary use case can involve workflow automation that can use the Bio-Knowledge graph for identifying Orphan/Rare disease innovation whitespaces. In some embodiments, different steps can be taken to achieve this workflow automation as follows. First, from the Semantic Bio-Knowledge Graph, the disease indication "entities" that are proximal in the neighborhood of each search term can be identified (e.g., for "real world phenotype" entities, such as "neurodegeneration," "remyelination," "angiogenesis," etc.). Second, for each identified disease indication, a system can determine the market(s) (e.g., commercial market, investment market) in one or more geographical areas, such as the United States, Western Europe, the United Kingdom, Japan, and emerging markets. The Bio-Knowledge Graph can be further used to power user interface (UI) to visualize the clinical competitive landscape for each disease and/or for each geographic region.

Figure 7:
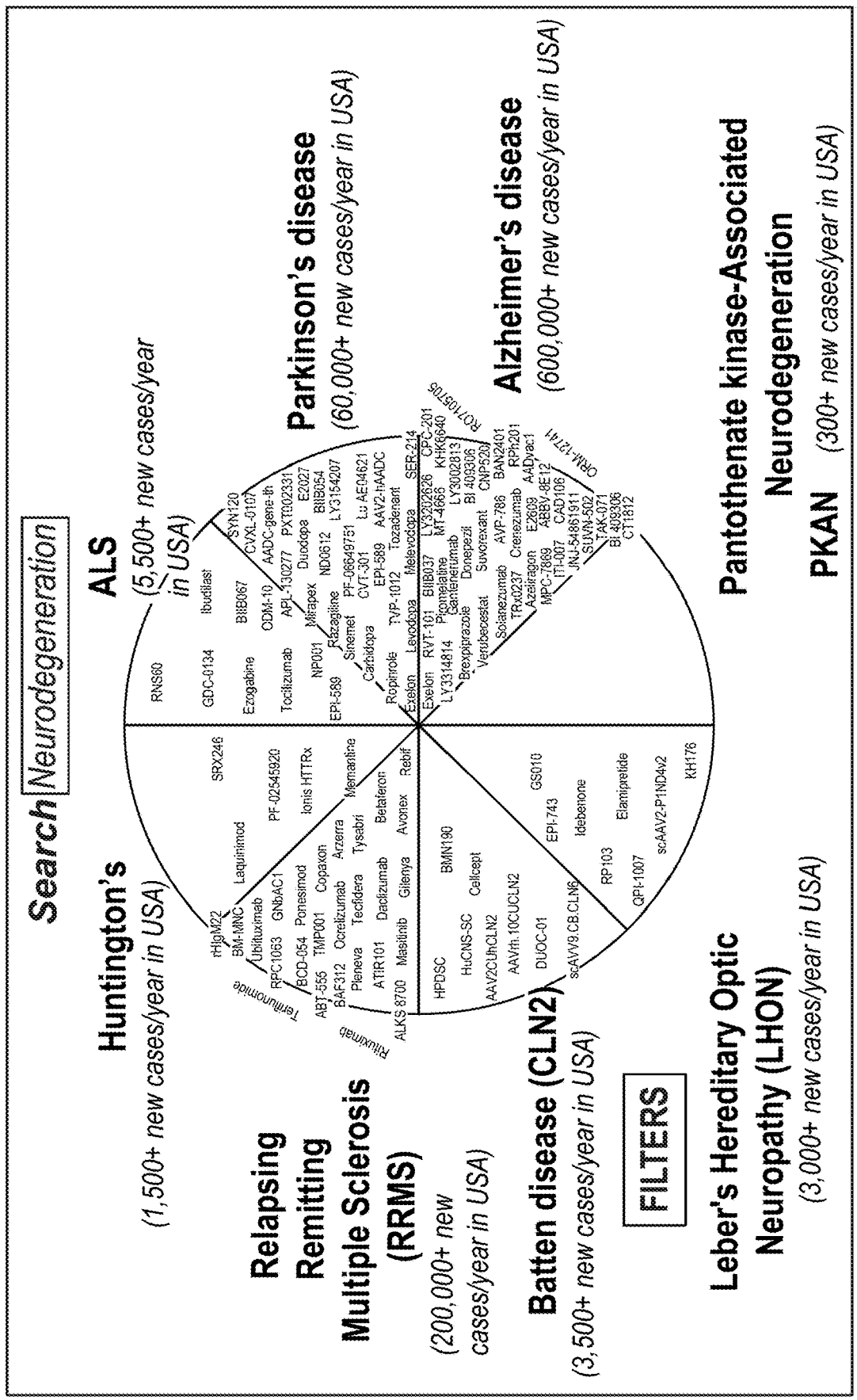
FIG. 7 illustrates a bull's eye view (an alternate 2D view) that can be a radial representation of the "symbolic" temporal phases in accordance with some embodiments of the present disclosure.

FIG. 7 illustrates an example bull's eye view (an alternate 2D view) that can be a radial representation of the "symbolic" temporal phases, where the closer to the center, the more advanced/marketed drugs; and where the closer to the periphery, the less developed/preclinical assets). The system can find and place drugs associated with each disease based on the cosine distance between the drug and the disease, and other factors (e.g., the search term, other related entity types, such as clinical trials). The exemplary bulls-eye visual shown for search term "Neurodegeneration" can show that rare diseases, such as PKAN, LHON, and CLN2, can offer innovation whitespaces. Third, the Bio-Knowledge Graph can also support subsequent user queries. For example, a use case can involve identifying additional risk factors associated with strategic bets for each disease-drug mechanism pair based on various types of information, including failed/terminated trials or signals from the Federal Adverse Event Reporting System (FAERS). Another common follow-up query can involve identifying specific assets (e.g., drugs, devices) that lend themselves to a Merger & Acquisition (M&A) or licensing strategy. This workflow can also be enabled by the visuals generated from the Bio-Knowledge Graph, such as one of the 2-D renderings (Bulls-eye, Competitive Pipeline, etc.). In some embodiments, the risk factors can be precomputed from one or more of various sources (e.g., FAERS, the number of failed/terminated clinical trials involving a specific drug and disease indication pair, etc.).

The bull's eye view of FIG. 7 also illustrates how a Bio-Knowledge graph can automatically capture real-time semantic relationships between any user-supplied query (e.g., "neurodegeneration") and different entities in its neighborhood (e.g., highlighted here for eight exemplary disease indications) in accordance with some embodiments of the present disclosure. For example, in FIG. 7, the user has searched "neurodegeneration." The system uses the Bio-Knowledge graph to identify the top labeled entities associated with the search term (e.g., "close" as measured by distance). The system then uses the entity type (taken from the label) associated with the top labeled entities to determine the nature of the data to display. In this example, the entity type/label "disease" is associated with the entities closest to the search term. Thus, the system associates each sector of the bull's eye with an entity that is a specific disease that is close to the search term "neurodegeneration" (e.g., ALS, Parkinson's, Alzheimer's, etc.). The system then discovers that the entity type/label "drug" is close to the search term. Thus, the system now fills in each respective sector of the graph with specific drugs that are close to the specific disease corresponding to that sector.

In some embodiments, the number of entities displayed can be fixed (e.g., the top eight disease indications). In some embodiments, the number of entities displayed can be overridden by using the "filters" function (e.g., the number can be increased or decreased; a specific entity can be added or removed). In some embodiments, the system can determine the initial number of entities to display based on the availability and significance of different entities in the results. The exemplary "Bulls-eye visual" shown here can pull together information from various clinical trials, drug names, and/or other associated information (e.g., company name, mechanism of action, etc.). This can ensure that corporate strategy and competitive intelligence functions are not misinformed of the market.

FIG. 8 illustrates a Bio-Knowledge graph that enables rapid organization of information on drugs and their competitors—across companies and mechanisms of action (or signaling pathways)—which can be at the heart of competitive market intelligence workflows in accordance with some embodiments of the present disclosure. In this example, for the search query "AML," the system can retrieve several different signaling pathways central to the disease, and represents drugs across the market in terms of their stage of development (e.g., here, clinical trial phases 1, 2, 3 and marketed are shown). Further, attributes of every trial that can impact commercial decisions and market sizing can be captured in the card views (e.g., genetic markers like FLT3-positive; First-line treatment information, and combination therapies like cytarabine+daunorubicin).

The example shown in FIG. 8 illustrates another exemplary use case involving competitive intelligence workflow automation that can integrate information across the diverse silos of R&D, clinical trials, bio-medical knowledgebase, company press releases/investor reports, and/or regulatory bodies to highlight commercially salient factors (e.g., first line treatment, bio-molecular constraints, combination therapy, etc.). In some embodiments, different steps can be taken to achieve this workflow automation. First, from the Semantic Bio-Knowledge Graph, for a disease indication entity searched by the user, the "pathway" entities and drugs that specifically act via these pathways from a mechanism of action (MOA) standpoint can be identified. Similar to the approach described for FIG. 7, the system displays entities that are pathways and drugs because these entity types/labels correspond to the labels associated with the closes entities associated with the search input "AML". Second, related entities from the drugs (such as the "company" that markets the drug, the stage of development (e.g., Preclinical, IND, Phase 1, Phase 1/2, Phase 2, Phase 3, Phase 4, NDA/Expected Launch, Marketed, etc.)) can be identified. "Trial group" entities, which can be series of clinical trials most closely related to each other (e.g., similar clinical trial parameters, such as first line treatment, combo/monotherapy, biomarker/target constraints) can be computed. Third, all the above information in a user-friendly perspective as a "competitive pipeline" visual can be integrated. For example, a pipeline view, as in FIG. 8, can be used. This pipeline view is a two dimensional spatial organization with each row identifying a specific drug (and the drug company) with the corresponding "stage of development" (the x-axis is the "symbolic" temporal phase, y-axis is individual drugs). One innovation in visualization can be the "aggregation" of drugs from different companies all sharing some common theme (such as the same molecular target mechanism). The system can identify such a common theme by examining the entity distribution. Each trial group can be shown as a distinct row and the individual clinical trial cards that constitute the group highlight just the commercially salient information that the Bio-Knowledge Graph has linked together. The entity distribution can identify candidate columns which can include entities and entity sequences. The ordering of terms can be based on templates or by training a model to generate the proper matrix of entity types to be rendered. Fourth, the competitive pipeline visual can enable quick summarization of the total number of drugs that are in various stages of development (e.g., Preclinical, IND, Phase 1, Phase 1/2, Phase 2, Phase 3, Phase 4, NDA/Expected Launch, Marketed, etc.). In some embodiments, the system can determine various stages of drug development based on distance relationships between the specific drugs/pathways of each row and clinical trial information in the Bio-Knowledge Graph. In some embodiments, this visual can provide rapid identification of the most clinically-advanced pathways (systems biology) and/or mechanism of action (of salient interest to R&D corporate strategy and market intelligence). The competitive pipeline visual can present an overview that enables rapid identification of assets of companies of specific interest, which can then be studied in a detailed fashion. Fifth, the visual shown here can also be readily expanded to (1) display the date the system last auto-updated information contained in the visual; (2) display subject matter experts (SMEs) involved in specifically validating the data displayed in the visual (including what date each SME last validated the data manually; and potentially even links to the SME's professional website/Linkedin); and (3) enable users to edit the visual displayed, save workflows/sessions, and download the visual directly as an image/PowerPoint slide, thus enhancing user productivity. The expansions can be based on associations between words that identify the knowledge being sought and the answers. For example, a user can click on the top row, enter "experts," and get the subject matter experts because of the distance between the drug's name and the expert's name. As another example, if the user enters "experts in CAR T-cell therapy," the system can retrieve all the current "key opinion leaders" in the field of chimeric antigen receptor T-cell (CART) therapy.

FIG. 9 illustrates a Bio-Knowledge graph queried for the exemplary phrase "Remyelination" followed by the Entity Recognition methods enable distinct entity classes to be visualized) in accordance with some embodiments of the present disclosure. In this illustrative example, drugs in panel 902, disease indications in panel 904, and biomolecular signals in panel 906 can show different entity types recognized in the neighborhood of the phrase "Remyelination." The entities can be ranked according to the cosine distance to the original query vector "Remyelination," where the cosine distance of 1 being the highest possible rank; and indicating the self-vector "Remyelination".

In some embodiments, another exemplary use case can involve enabling users to query "Real World Phenotypes" to visualize related entities ranked in decreasing relevance, to identify "Orphan/Rare disease" investment avenues. The real world phenotype "Remyelination" can be salient for pharmaceutical companies studying central nervous system (CNS) disorders. Yet the "word" Remyelination does not exist in human-curated disease/indication corpuses (such as ICD10) which only catalog disease indications. Given that individuals across each Pharmaceutical company possess their own unique set of "Real World Phenotypes," users of competitive intelligence and corporate strategy functionalities are very likely to query any system with real world phenotypes like "Remyelination." The use of existing databases for this purpose can lead to misinformed commercial, clinical and R&D investment decisions. In some embodiments, the Bio-Knowledge Graph includes several millions of entities, including thousands of Real-World Phenotypes like "Remyelination." The Bio-Knowledge Graph can further accurately capture the neighborhood of "Remyelination" for diverse entities such as drugs/compounds, diseases/indications, genes, etc. as shown in FIG. 9.

Examples above can show how visuals like the competitive pipeline and bulls-eye can be equipped with the distinctive ability to link diverse important entities (such as genes, drugs, diseases) for high-value queries like "Remyelination." For example, the results for "Remyelination" can identify the disease indication Pelizaeus-Merzbacher Disease (PMD) and the causally-linked PLP1 gene (refer to FIG. 10), reflecting these insights on the user interface (UI) makes the visuals "semantically accurate." This can overcome a fatal flaw of the existing predominantly-lexical search-and-retrieve powered user interfaces for competitive intelligence and corporate strategy functionalities. The results for "Remyelination" can also identify other disease indications (e.g., any of the other disease indications in panel 904) and find causally-linked genes and/or drugs using a bio-knowledge graph similar to the one shown in FIG. 10. In some embodiments, the system or user can choose any entity, and the system can determine other causally-linked entities based on the chosen entity using a bio-knowledge graph similar to the one shown in FIG. 10. In some embodiments, the system can populate the pathway inhibitor(s) by using a combination of structured knowledge bases to retrieve all known inhibitors that target a pathway that is identified by the system. In some embodiments, "neighborhoods" of an inhibitor can be used to identify all other "inhibitors" entities in that neighborhood, and then in each of those "inhibitors" neighborhoods, the system can determine how "close" are the "genes" or "pathway" case-by-case.

Figure 10:
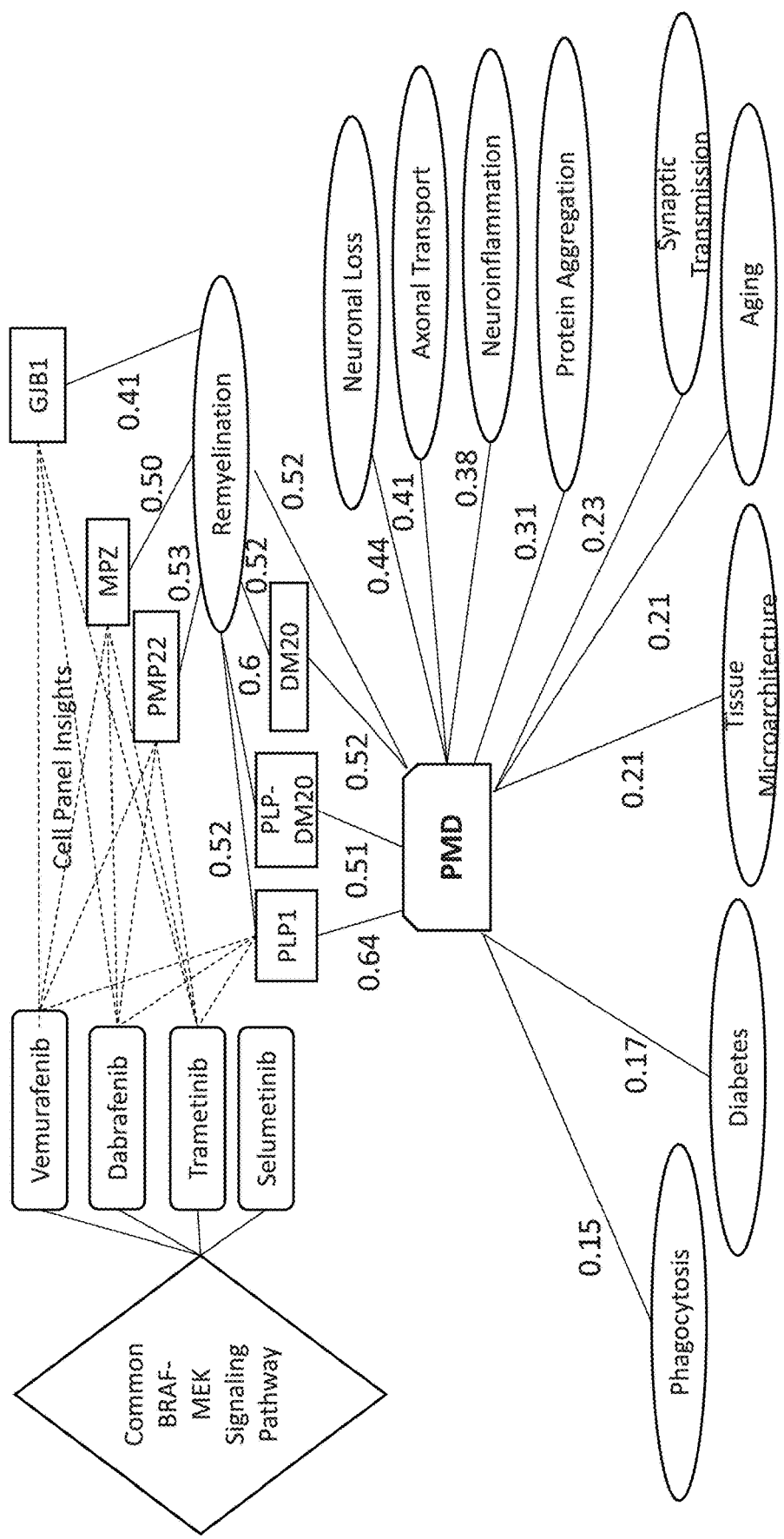
FIG. 10 illustrates output from a Bio-Knowledge graph that can enable identifying disease indications that are closely related to any real world phenotype query supplied by the user in accordance with some embodiments of the present disclosure.

FIG. 10 illustrates a Bio-Knowledge graph that can enable identifying disease indications that are closely related to any real world phenotype query supplied by the user in accordance with some embodiments of the present disclosure. For the illustrative example shown here, the query "Remyelination" can result in identification of the orphan/rare disease PMD (Pelizhus-Mazbacher Disease). Analysis of the neighborhood of PMD in turn can reveal several other real-world phenotypes in decreasing order of relation to PMD—specifically, neuronal loss, axonal transport, and neuroinflammation. The numbers in FIG. 10 represent cosine distances between two entities. Thus, the higher the cosine distance, the closer the two entities are. In this example, neuronal loss, axonal transport, and neuroinflammation are less coupled to PMD than Remyelination is. This can be followed by Protein aggregation, and finally the phenotypes with lowest connection to PMD are synaptic transmission, aging, tissue microarchitecture, diabetes, and phagocytosis, respectively. In this example, the genes PLP1 (including the splicing variant DM20), PMP22, MPZ, and GJB1 are all in the neighborhood of the PMD disease vector. Utilization of additional biopanel screening experimental data sets can further suggest that BRAF and MEK pathway inhibitors are specifically sensitive to samples that over-express the PLP1, PMP22, MPZ, and GJB1 genes. In some embodiments, these additional biopanel screening experimental data sets can come from one or more structured databases, such as the Cancer Therapeutics Response Portal (CTRP) v2 published by the Broad Institute, the Cancer Cell Line Encyclopedia (CCLE) published by the Broad institute, Sanger Institute's Catalogue Of Somatic Mutations In Cancer (COSMIC), and Genomics of Drug Sensitivity in Cancer (GDSC) databases. In some embodiments, any number of external structured databases or knowledgebases can be used to glean additional insights. Hence, the disclosed invention motivates testing BRAF-MEK inhibitors in remyelination assays. In this example, as above, the type of entities to show as related to the search term "PMD" can be determined by the types of entities associated with the actual entities that are closest to the search term (e.g., real-world phenotype). Each successive type of entity to be shown (e.g., genes) can in turn be determined by the type of entity associated with the search term "PMD" and the top entity value "remyelination". At each level, a new entity type is discovered (e.g., drug) from the top entities values associated with preceding entities values (e.g., the specific genes). In this way, multiple levels of relationships can be uncovered by the system.

In some cases, the same entity can refer to more than one entity type. For example, the entity "ICOS" can refer to a gene type (Inducible T-Cell Co-Stimulator), a company name (the trademark of Icos Corporation, which was a company that was acquired by Eli Lilly and Company in 2007), or some other entity type. Such an entity can create an ambiguity to traditional systems. For example, if a user enters the query term "ICOS" into a traditional search engine, the search engine produces results that do not account for different meanings of "ICOS." According to some embodiments, disclosed systems and methods can recognize different entity types for a given entity. These different entity types can be presented in different neighborhood senses. For each neighborhood sense, relevant entities associated with the given entity can be presented.

Figure 31:
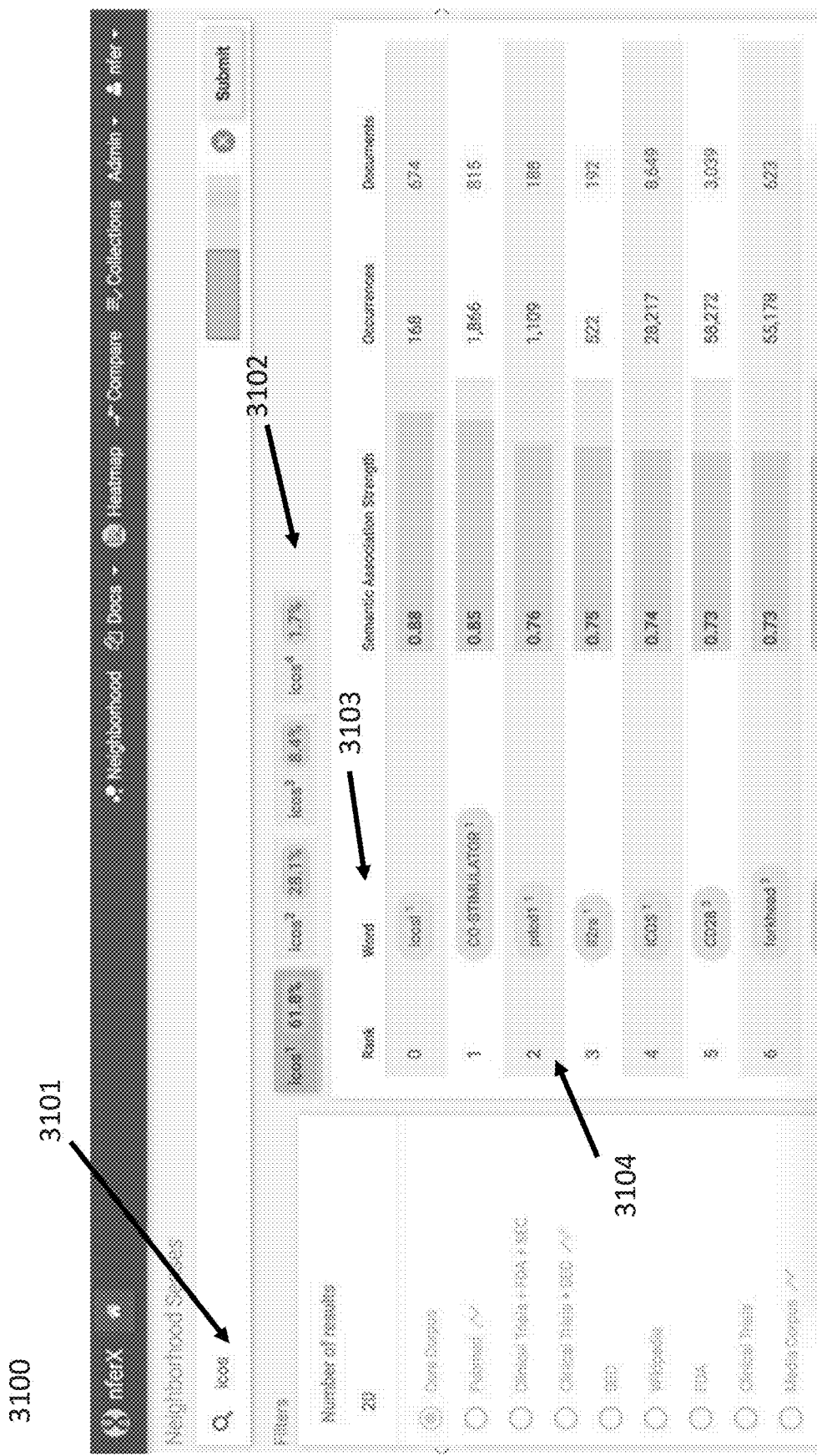
FIG. 31 illustrates an exemplary neighborhood sense interface in accordance with some embodiments of the present disclosure.

FIG. 31 illustrates an exemplary neighborhood sense interface 3100 in accordance with some embodiments of the present disclosure. When an entity is entered as a query term 3101 and the entity is associated with more than one entity type, then the neighborhood sense interface 3100 presents neighborhood senses, each of which corresponds to one of the different entity types. Each neighborhood sense is associated with entities that are associated with the query term 3101 and also with the entity type that corresponds to the neighborhood sense. For example, for the query term "icos" 3101, the neighborhood sense interface 3100 can present four different neighborhood senses 3102 ($icos^1$, $icos^2$, $icos^3$, and $icos^4$). In some embodiments, each neighborhood sense can be associated with a percentage that represents the probability of the query term 3101 being in the respective neighborhood sense. For example, the value of 61.8% shown beside $icos^1$ can indicate that the query term "icos" is associated with the neighborhood sense $icos^1$ 61.8% of the time in the corpus. In the neighborhood sense "$icos^1$," words or entities 3103 that are associated with the query term "icos" can include "icos1," "CO STIMULATOR," "pdcd1," "il2ra," "ICOS," CD28," and "forkhead"—which can be listed in a decreasing order of their semantic association strength with respect to the query term "icos." By analyzing these entities in the neighborhood sense $icos^1$, the system or the user can recognize that the entity type for "icos" in this neighborhood sense is likely to be "gene type." In this example, the row 3104 shows that the word "pdcd1" has the third highest semantic association strength of 0.76 and occurs 1,109 times in 188 of the documents in the corpus. For a given query term, its neighborhoods senses can be determined using various methods. For example, Adaptive Skip-gram (Adagram) model can be implemented to capture word vectors that are generated from an unsupervised learning model. Other methods and models that can be used include Multisense Skip-gram (e.g., Neelakantan et al. (2014)) and/or any other suitable model or method that can infer different senses of a word in a context (e.g., biological context).

Figure 32:
FIG. 32 illustrates an exemplary neighborhood sense interface in accordance with some embodiments of the present disclosure.

FIG. 32 illustrates an exemplary neighborhood sense interface 3200 in accordance with some embodiments of the present disclosure. FIG. 32 shows the results for the query term "icos," when the neighborhood sense is $icos^2$. In FIG. 32, entities that have the highest semantic association strengths include "henneys," "pharmaceuticals," "xoma," henney," "Genentech," "companies," and "therapeutics." From these entities, the system or the user can recognize that the entity type for "icos" in this neighborhood sense is likely to be "company name."

Figure 33:
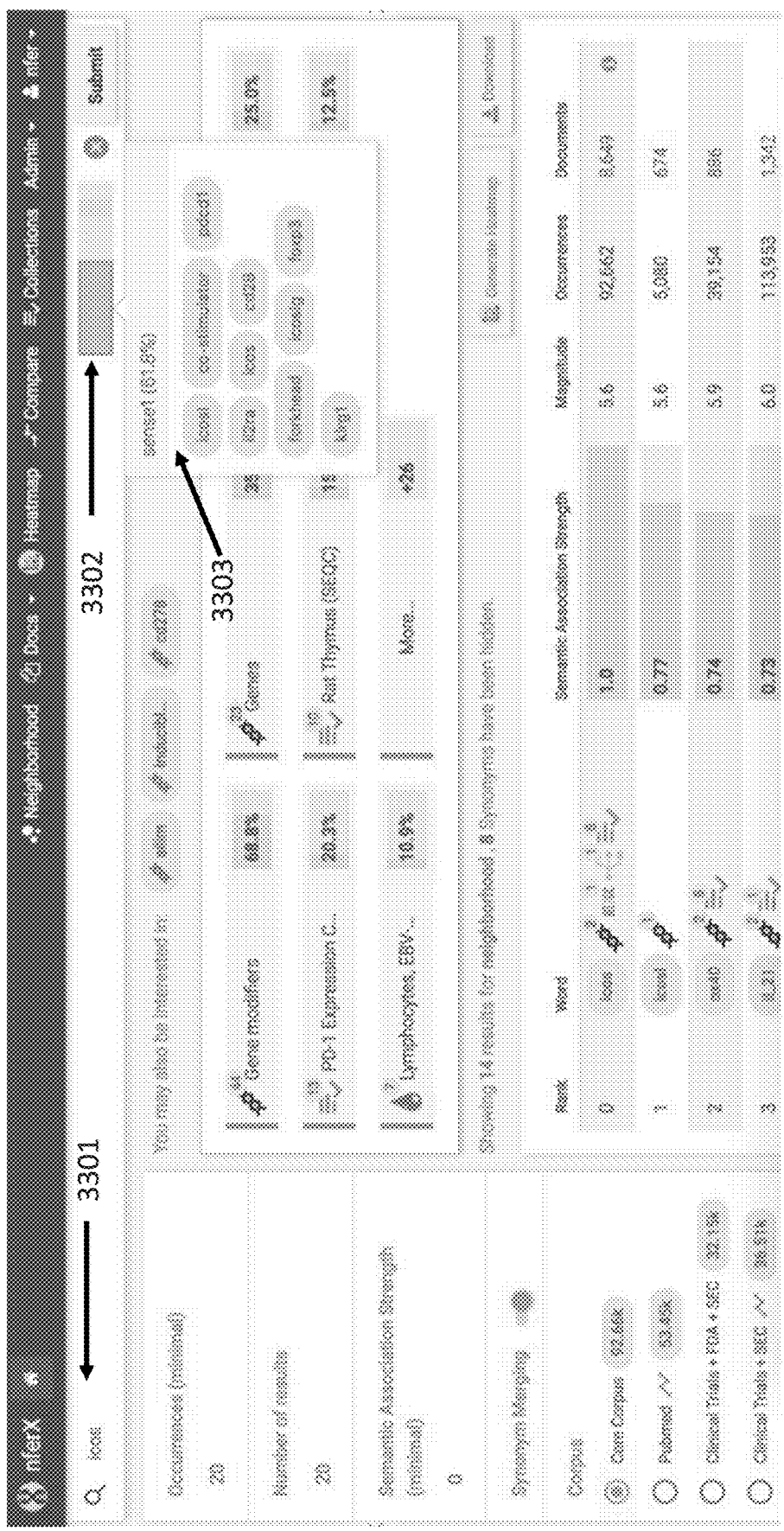
FIG. 33 illustrates an exemplary knowledge diagram interface in accordance with some embodiments of the present disclosure.

FIG. 33 illustrates an exemplary knowledge diagram interface 3300 in accordance with some embodiments of the present disclosure. The knowledge diagram interface 3300 can display different neighborhood senses 3302 associated with a query term 3301. Each neighborhood sense can be linked to a detail box 3303 that shows a probability of the query term 3301 being in the respective neighborhood sense and the list of entities associated with the neighborhood sense. For example, for the query term "icos" 3301, the knowledge diagram interface 3300 shows that there are four neighborhood senses 3302 (represented as four divisions of a rectangle). The probability of "icos" being in the first neighborhood sense is 61.8%. The first neighborhood sense includes the following entities: "icosl," "co-simulator," "pdcd1," "il2ra," "icos," "cd28," "forkhead," "icosig," "foxp3," and "klrg1." In some embodiments, the detail box 3303 can be accessed by clicking on the division in the rectangle 3302 that corresponds to the desired neighborhood sense.

Thus, in some embodiments, the system or the user can determine the neighborhood sense corresponding to the desired entity type by analyzing the resulting entities for each neighborhood sense.

Figure 34:
FIG. 34 illustrates an exemplary knowledge diagram interface in accordance with some embodiments of the present disclosure.

FIG. 34 illustrates an exemplary knowledge diagram interface 3400 in accordance with some embodiments of the present disclosure. The knowledge diagram interface 3400 is similar to the knowledge diagram 3300 (FIG. 33), except that the detail box 3403 now shows information for the second neighborhood sense. The probability of "icos" being in the second neighborhood is 28.1%. The second neighborhood sense includes the following tokens: "henneys," "pharmaceuticals," "xoma," "henney," "genentech," "companies," "therapeutics," "lilly," "boards," and "vaxgen."

Figure 35:
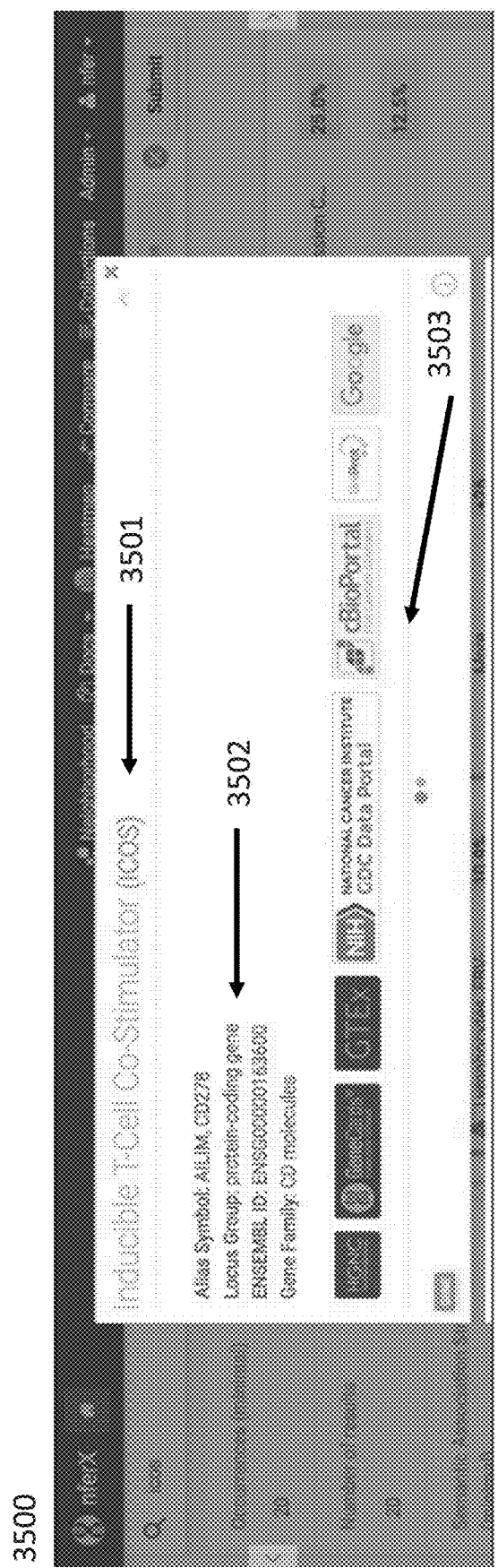
FIG. 35 illustrates an exemplary information box in accordance with some embodiments of the present disclosure.

FIG. 35 illustrates an exemplary information box 3500 in accordance with some embodiments of the present disclosure. The information box 3500 can provide aggregated information for an entity. This can be useful when there is ambiguity to which entity type the entity belongs. For example, when the information box 3500 for the entity "icos" is launched for the first neighborhood sense, the information box 3500 states that "icos" refers to "Inducible T-Cell Co-Stimulator (ICOS)" 3501 and provides detailed information 3502 about the gene "icos." The information box 3500 can further provide one or more resources 3503 from which such detailed information is retrieved. For example, the information box 3500 lists the following resources 3503: HGNC, GeneCards, GTEx, NIH National Cancer Institute GDC Data Portal, cBioPortal FOR CANCER GENOMICS, UniProt, and Google. In some embodiments, each of these resources can be linked to its respective resource website or database.

Figure 36:
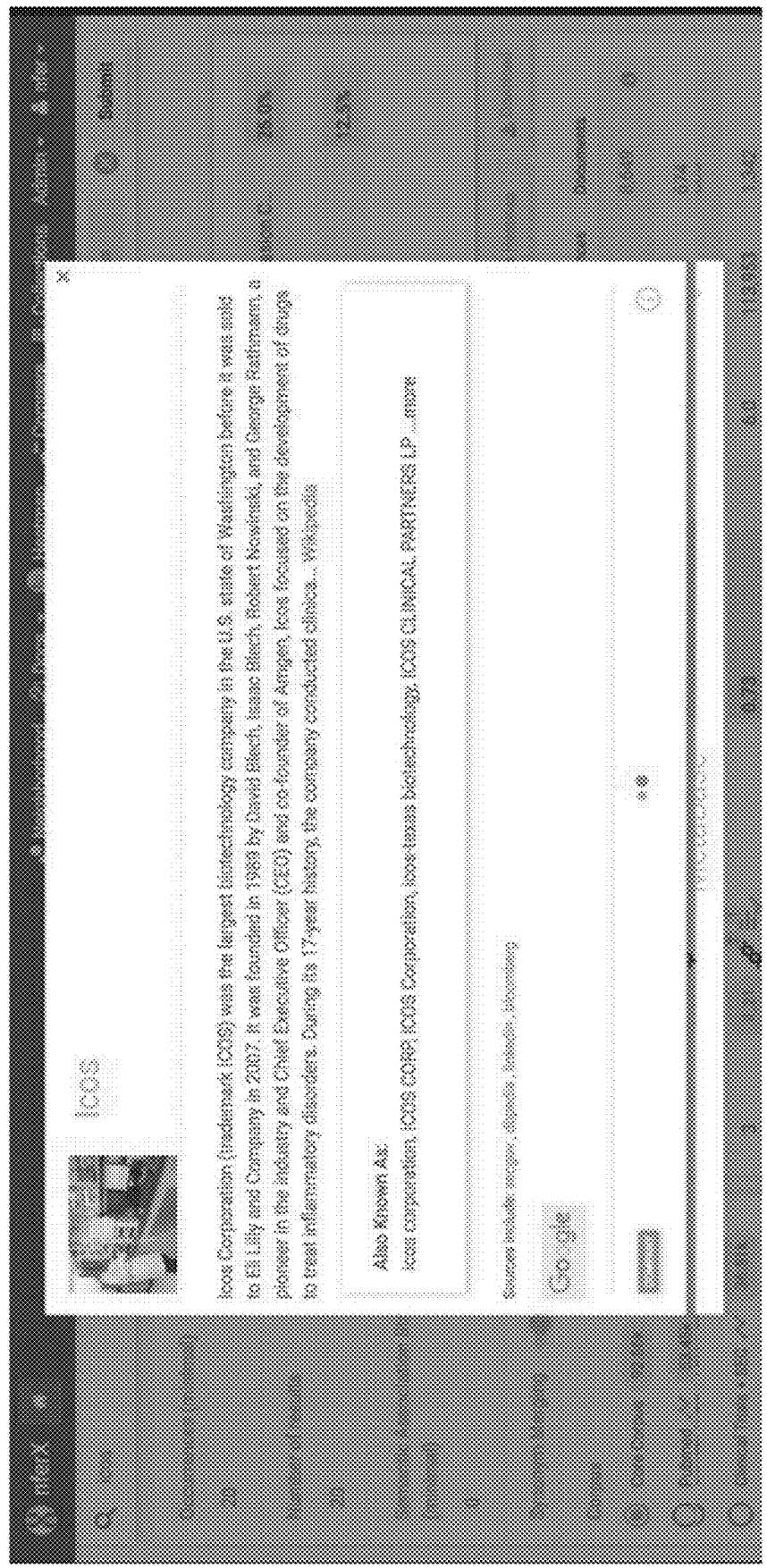
FIG. 36 illustrates an exemplary information box in accordance with some embodiments of the present disclosure.

FIG. 36 illustrates an exemplary information box 3600 in accordance with some embodiments of the present disclosure. The information box 3600 can provide information about the entity "icos" when the entity "icos" refers to the entity type "company name." In this context, the information box 3600 provides information about the company "icos" rather than about the gene type "icos." In some embodiments, only the resource links that provide information about the company "icos" can be displayed. For example, only the link to Google can be provided in the information box 3600 when all the other resources do not provide information about the company "icos."

Thus, in some embodiments, the system or the user can determine and choose the neighborhood sense corresponding to the desired entity type by analyzing the information in the information box.

FIGS. 52-56 illustrate neighborhood sense diagrams for the entity "Rho" that is associated with five different entity types in accordance with some embodiments of the present disclosure. In some embodiments, "Rho" can be represented as a different vector for each of its association with the five different entity types.

In FIG. 52, the first neighborhood sense (Rho') is associated with words related to mathematical correlations, such as "pearson" and "spearman." Thus, it can be concluded that this neighborhood sense captures the use of "Rho" (the Greek symbol) as the symbol for Spearman's Rank Correlation, which is also known as Spearman's Rho.

In FIG. 53, the second neighborhood sense (Rho$^2$) is associated with words related to other Greek symbols, including sigma, mu and pi. Thus, it can be concluded that this neighborhood sense captures the use of "Rho" as the 17th letter of the Greek alphabet.

In FIG. 54, the third neighborhood sense (Rho$^3$) is associated with words related to other GTPases, including "guanosine" and "RHOA." Thus, it can be concluded that this neighborhood sense captures the use of "Rho" as the family of small GTPases that act as molecular switches in signal transduction cascades.

In FIG. 55, the fourth neighborhood sense (Rho$^4$) is associated with words related to Rho Ventures (an investment fund), including the last name of its managing director "leschly," the last name of the managing partner "kairouz," and the word "ventures." Thus, it can be concluded that this neighborhood sense captures the use of "Rho" as the investment fund.

Figure 56:
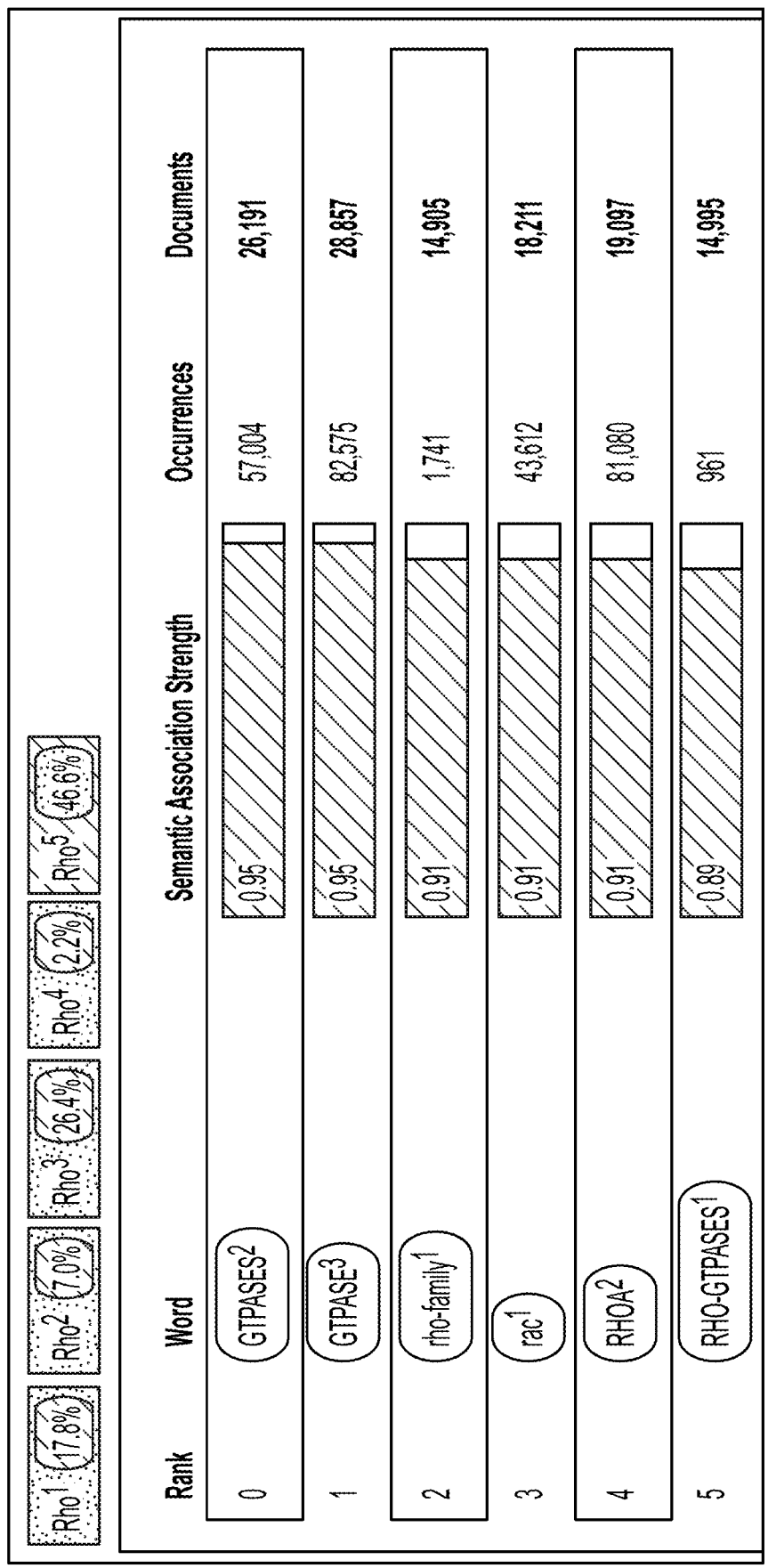

In FIG. 56, the fifth neighborhood sense (Rho$^5$) is associated with the words "GTPASES" and "GTPASE" as the top associations, in addition to "RHOA" (a gene symbol of the GTPase). Thus, it can be concluded that this neighborhood sense captures the use of "Rho" as the GTPase protein family.

Figure 37:
FIG. 37 illustrates an exemplary knowledge diagram interface in accordance with some embodiments of the present disclosure.

FIG. 37 illustrates an exemplary knowledge diagram interface 3700 in accordance with some embodiments of the present disclosure. In some embodiments, the knowledge diagram interface 3700 can provide a query box 3701, where the user can input a query term (a word or a phrase) which can be used to query for entities that have sematic association with the query term. The knowledge diagram interface 3700 can provide one or more filters for the query. In some embodiments, the minimum number of occurrences 3702 for the resulting entities can be set. For example, if the user sets the minimum number of occurrences 3702 to "20," the query results can only include entities that occur at least 20 times in the corpus.

In some embodiments, the number of results 3703 for the query can be set. For example, if the user sets the number of results 3702 to "20," only the 20 results are displayed in the output box 3708 that displays the results of cosine analysis of word embeddings and related data. If the number of results is less than 20, the number of results displayed in the output box 3708 can be less than 20. If the number of results is more than 20, only the top 20 results (e.g., the 20 entities with the highest semantic association strengths) can be displayed. The other results can be ignored. Alternatively, a function can provide the user to navigate to another page(s) for the other results.

In some embodiments, the minimum semantic association strength 3704 can be set. For example, if the minimum semantic association strength is set to "0.0," all the entities are considered for the query regardless of their semantic association strength. However, if the minimum semantic association strength 3704 is set to "0.3," only the entities that have their semantic association strengths of 0.3 or more are considered.

In some embodiments, the corpus selection function 3705 can set the corpus to be considered for the query. The core corpus can represent a superset of all the available data sets in the system. For example, if the corpus selection function 3705 sets "Core Corpus" (which includes 98.14k documents in this example), all the available data sets (including Pubmed, Clinical Trials, FDA, SEC, Wikipedia, and Media Corpus) are considered for the query. One or more of the individual data sets can be selected by selecting options other than the core corpus in the corpus 3705.

In some embodiments, the knowledge diagram interface 3700 can suggest one or more entities 3706 that may be of interest to the user. Such suggestions can be based on the user's query term, and/or the user's setting. Such suggestions can also be based on the user's previous interaction with the system and/or other user's interactions with the system. In some embodiments, the suggestions can be entities that have high semantic associations with the query term. In some embodiments, the suggestions can come from synonyms that are stored in a synonym database. In some embodiments, FASText can be used to determine synonyms.

In some embodiments, a knowledge synthesis box 3707 can list one or more token collections in the selected neighborhood sense for the query term 3701. For example, the token collections associated with the neighborhood of the query term "pcsk9" can include "Gene modifiers," "Genes," "All Genes," "Live Hepatocel . . . ," "Rat Liver (SEQC)," "Pathogenic Alle . . . ," "Liver (GTEx)," and other neighborhoods (shown as "More . . . +15"). In some embodiments, a token collection can refer to a collection of entities of the same entity type. In some embodiments, a token collection can be machine-generated and/or human-curated.

In some embodiments, a set of token collections can be determined based on one or more entities that are associated with the query term 3701. For example (hereinafter refer to as "Example A"), let's assume that the query term "E1" is associated with the following entities: "A1," "A2," "A3," "A4," "A5," and "A6." Let's also assume that "A1," "A2," and "A3" belong to the token collection "EC1"; "A4" and "A5" belong to the token collection "EC2"; and "A6" belongs to the token collection "EC3." In this example, the set of token collections can be determined to include EC1, EC2, and EC3. These token collections can be displayed in the knowledge synthesis box 3707 for the query term "E1." In some embodiments, the knowledge synthesis box 3707 can display only a subset of these token collections. For example, the system can select to display only the top two entity collections with the highest number of entities. In Example A, it can select to display only EC1 and EC2 because they each include more entities than EC3. In some embodiments, the system can select to display token collections based on other criteria—or example, selecting to display two token collections with the highest mean or median semantic association strengths of the entities included in each token collection.

In some embodiments, a set of token collections can be determined based on one or more entities that are associated with the query term 3701 and satisfy a certain condition(s). For example, to be included in the set of token collections, a token collection must have greater than, less than, or equal to a certain number of entities in the token collection. As another example, to be included in the set of token collections, a token collection must have a mean or median semantic association strength that is greater than, less than, or equal to a certain number of semantic association strength. In Example A above, if a token collection requires to have at least two entities to be included in the set of token collections, then only EC1 and EC2 would be included in the set of token collections. Yet in another example, not all entities that are associated with the query term 3701 are considered. In other words, the system can filter out those entities that do not satisfy a certain condition(s) before determining the set of token collections. In Example A above, let's further assume that the system requires all entities being considered to have at least a semantic association strength of 0.7; that A3, A4, A5, and A6 each have a semantic association strength that is greater than 0.7, but A1 and A2 do not; and that the knowledge synthesis box 3707 displays only one token collection with the most number of tokens. In this case, the knowledge synthesis box 3707 would display EC2 because the system would now determine that EC1 has only A3, EC2 still has A4 and A5, and EC3 still has A6.

In some embodiments, each token collection can be associated with a percentage, where the percentage can represent the number of tokens in the respective token collection divided by the total number of tokens in all of the token collections. In some cases, the sum of the percentages of the token collections can add up to more than 100% because one or more tokens can belong to more than one token collection. In some embodiments, the knowledge synthesis box 3707 can select to display token collections, whose percentages are greater than a certain threshold.

In some embodiments, one or more filters can be applied before, during, and/or after generating a list of token collections. In some embodiments, the query term's neighbors can be filtered out from the results or the token collections when the co-occurrence level between the neighbors and the query term is above or below a certain threshold. For example, only neighbors that have high co-occurrence levels can be selected. In another example, only neighbors that have zero co-occurrence levels can be selected. Using filters, it can be controlled to have one or more of the following types of results: (1) neighbors that have high cosine distances and high co-occurrence levels; (2) neighbors that have low or zero co-occurrence levels, but are related via other entities; (3) neighbors that have high cosine distances but low or zero co-occurrence levels; (4) neighbors that have a high occurrence within the overall corpora of interest and high co-occurrence levels; and (5) neighbors that have a low overall occurrence within the corpora of interest but have high co-occurrence levels. The later filter can be of particular interest, as it can indicate an association between entities/tokens that is starting to emerge but is not yet well-known or recognized. These types of results are non-limiting and are not necessarily mutually-exclusive.

In some embodiments, the output box 3708 can produce results associated with the query term 3701. For example, the output box 3708 can provide the results in a decreasing order of the semantic association strengths of the resulting entities. The output box 3708 can also display a magnitude, a number of occurrences, and a number of documents associated with each entity in the results. In some embodiments, the magnitude can refer to the magnitude of a vector associated with an entity, where the magnitude is the L2-norm (i.e., the square root of the sum of the squares of the individual dimensions of the vector). For example, the entity "circulating_pcsk9"'s semantic association strength is 0.81. Its magnitude is 5.4. It occurs 494 times in 237 of the documents in the selected corpus. Moreover, entity collections that are associated with each entity can be displayed.

Figure 38:
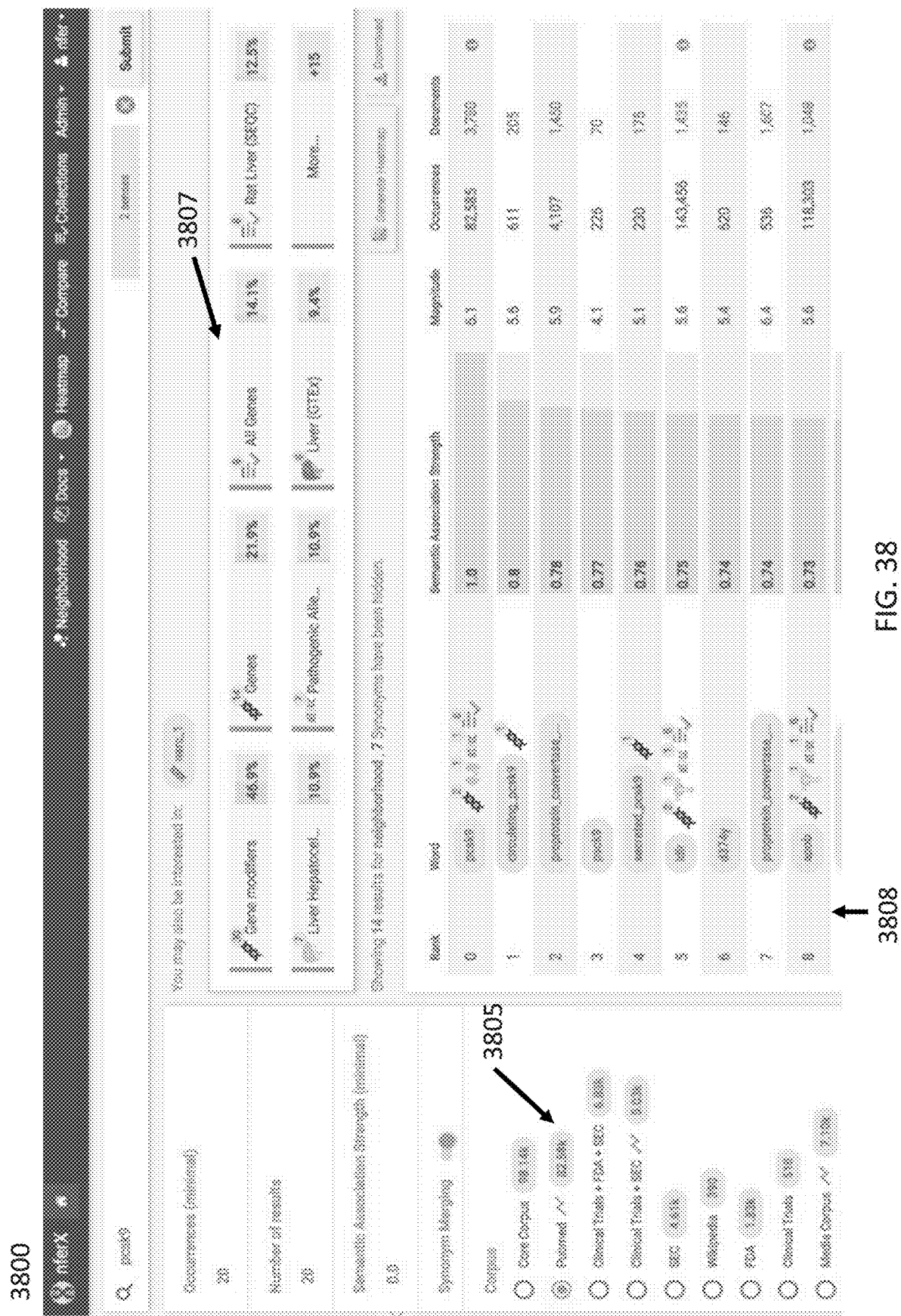
FIG. 38 illustrates an exemplary knowledge diagram interface in accordance with some embodiments of the present disclosure.

FIG. 38 illustrates an exemplary knowledge diagram interface 3800 in accordance with some embodiments of the present disclosure. The knowledge diagram interface 3800 is similar to the knowledge diagram interface 3700 (FIG. 37), except that the selected corpus 3805 is "Pubmed." Thus, in this example, the query is limited to the documents that exists in the Pubmed database, causing different results to be produced in the knowledge synthesis box 3807 and the output box 3808.

Figure 39:
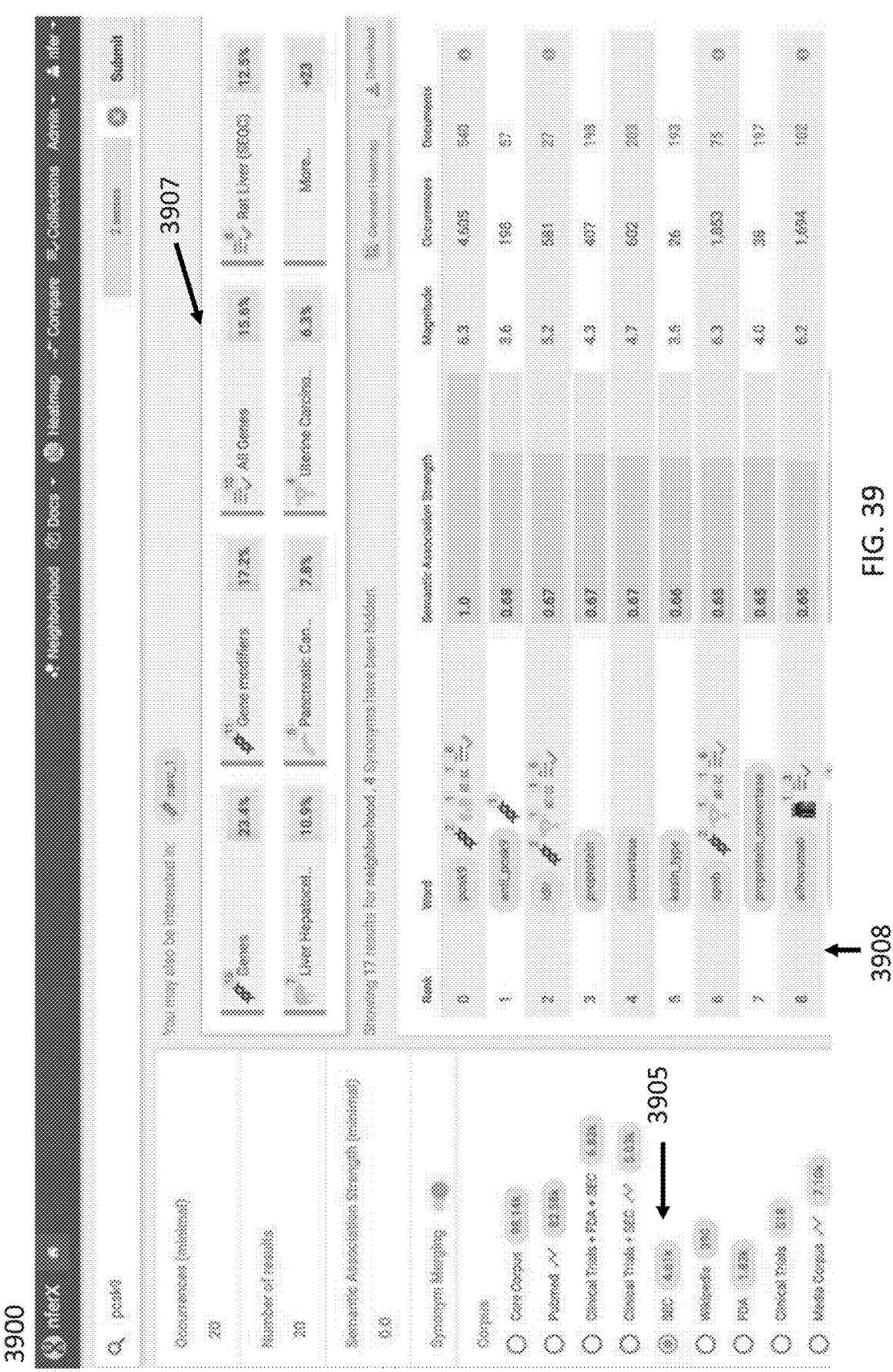
FIG. 39 illustrates an exemplary knowledge diagram interface in accordance with some embodiments of the present disclosure.

FIG. 39 illustrates an exemplary knowledge diagram interface 3900 in accordance with some embodiments of the present disclosure. The knowledge diagram interface 3900 is similar to the knowledge diagram interface 3700 (FIG. 37), except that the selected corpus 3905 is "SEC." Thus, in this example, the query is limited to the documents that exists in the SEC database, causing different results to be produced in the knowledge synthesis box 3907 and the output box 3908.

Figure 40:
FIG. 40 illustrates an exemplary knowledge diagram interface in accordance with some embodiments of the present disclosure.

FIG. 40 illustrates an exemplary knowledge diagram interface 4000 in accordance with some embodiments of the present disclosure. The knowledge diagram interface 4000 is similar to the knowledge diagram interface 3700 (FIG. 37), except that the selected corpus 4005 is "Media Corpus." Thus, in this example, the query is limited to the documents that exists in the Media Corpus database, causing different results to be produced in the knowledge synthesis box 4007 and the output box 4008.

Figure 41:
FIG. 41 illustrates an exemplary knowledge diagram interface in accordance with some embodiments of the present disclosure.

FIG. 41 illustrates an exemplary knowledge diagram interface 4100 in accordance with some embodiments of the present disclosure. An entity can be associated with one or more synonyms. For example, the entity "pcsk9" can have the following synonyms: "pcsk9s," "pcsk9_pcsk9," "pcsk9_ldlr," "ldlr_pcsk9," and "pcsk9_mediated." In some embodiments, synonyms can be generated in the same way as how suggestions can be generated, as described above. Disclosed systems and methods can merge synonyms for an entity such that results of a query do not list synonyms as separate words. In some embodiments, the knowledge diagram interface 4100 can allow the synonym merging functionality 4101 to be enabled or disabled. When the synonym merging functionality is disabled 4101, the system treats an entity and its synonyms as different entities. For example, when the synonym merging functionality is disabled 4101, the entity "pcsk9" and any of its synonyms above are treated as different entities.

Figure 42:
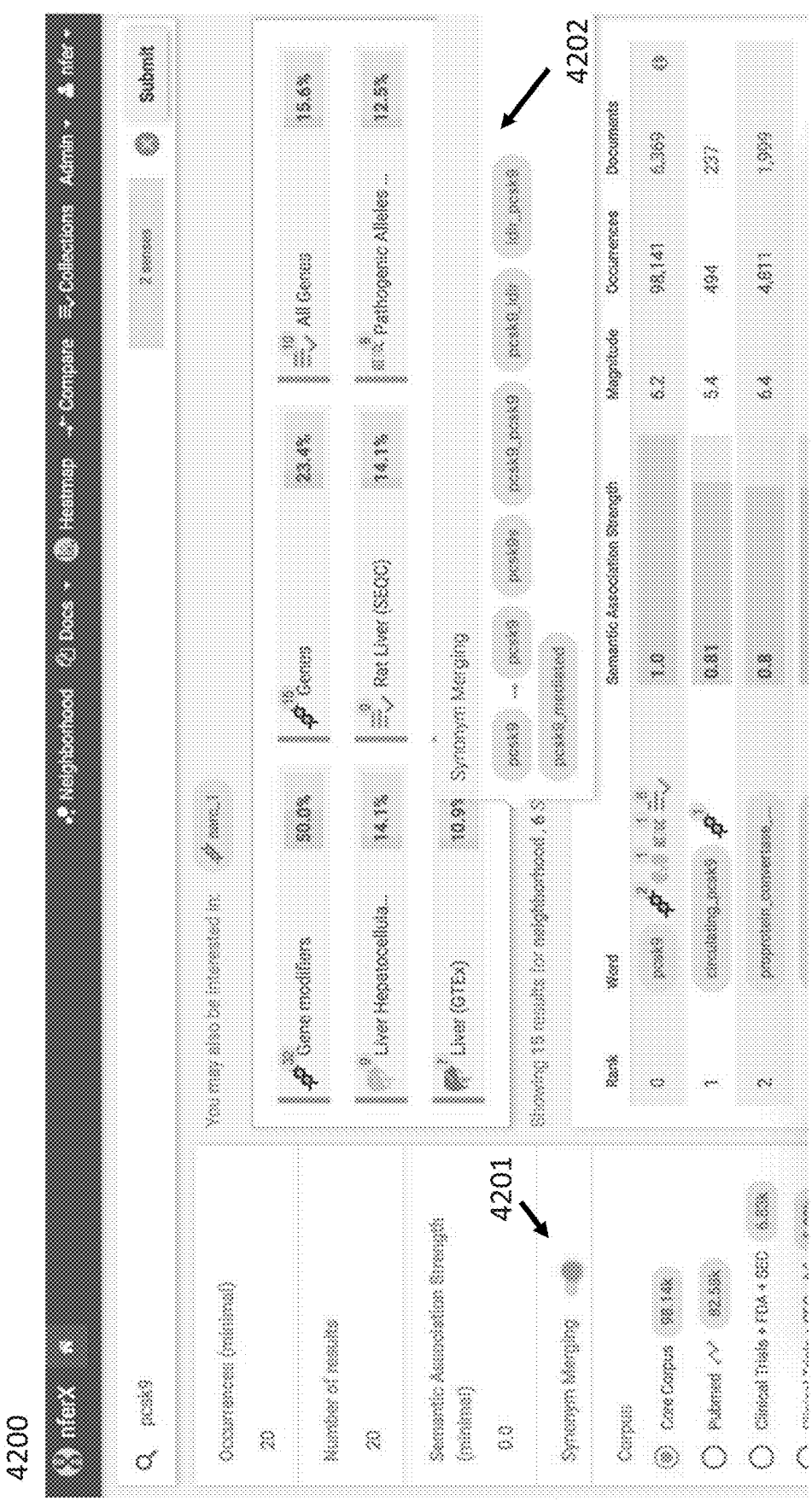
FIG. 42 illustrates an exemplary knowledge diagram interface in accordance with some embodiments of the present disclosure.

FIG. 42 illustrates an exemplary knowledge diagram interface 4200 in accordance with some embodiments of the present disclosure. In FIG. 42, the synonym merging functionality is enabled 4201, causing an entity and its synonyms to be treated as a single entity. For example, the synonyms in the synonym list 4202 shows all the synonyms of the entity "pcsk9" that are treated as the same entity as the entity "pcsk9."

Figure 43:
FIGS. 43-44 illustrate exemplary knowledge diagram interfaces in accordance with some embodiments of the present disclosure.
Figure 44:
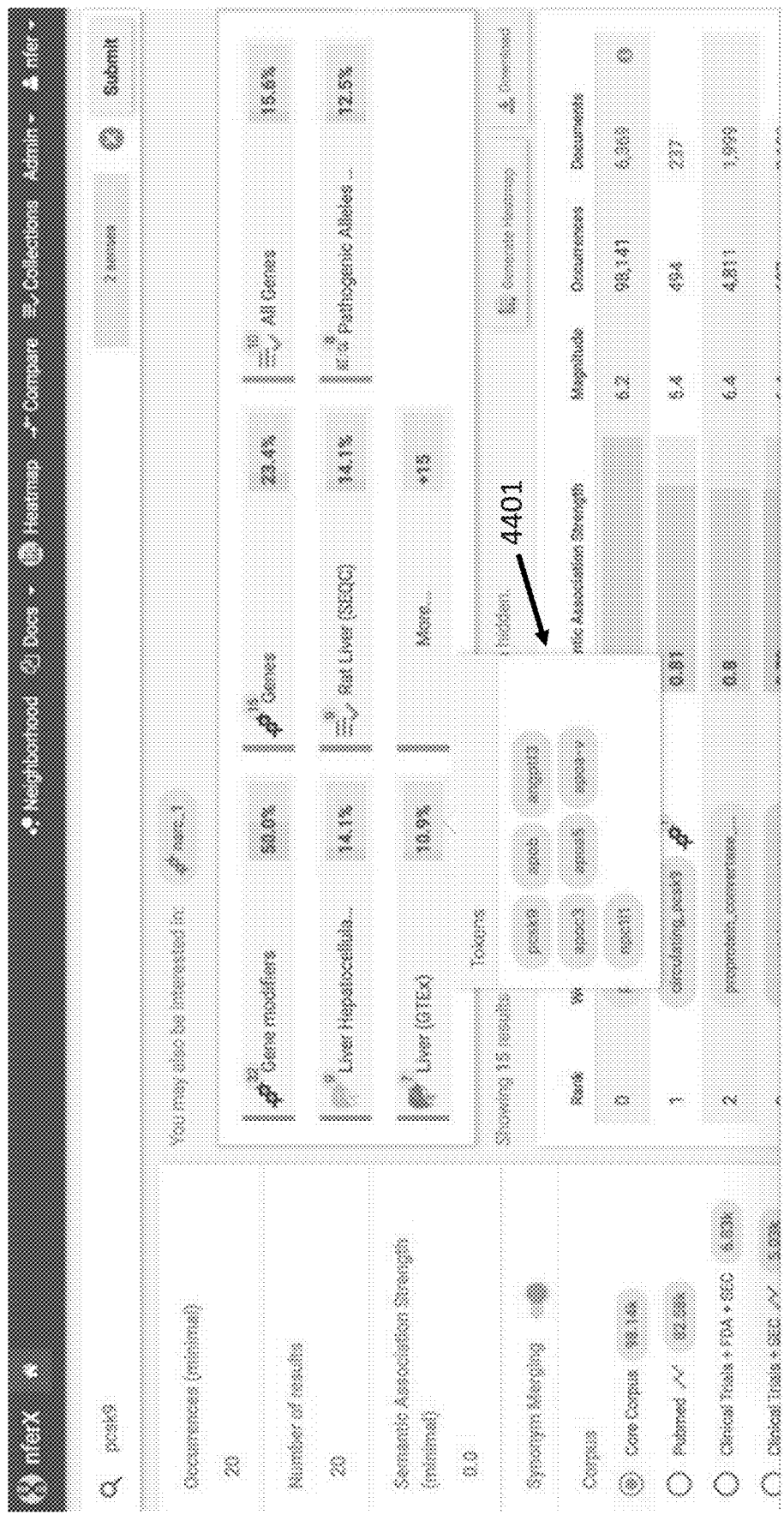

FIGS. 43-44 illustrate exemplary knowledge diagram interfaces 4300, 4400, respectively, in accordance with some embodiments of the present disclosure. The knowledge diagram interfaces 4300, 4400 illustrate token lists 4301, 4401, each of which lists the tokens in a given token collection. For example, the token list 4301 lists all the tokens in the Genes token collection. As another example, the token list 4401 lists all the tokens in the Liver (GTEx) token collection.

Figure 45:
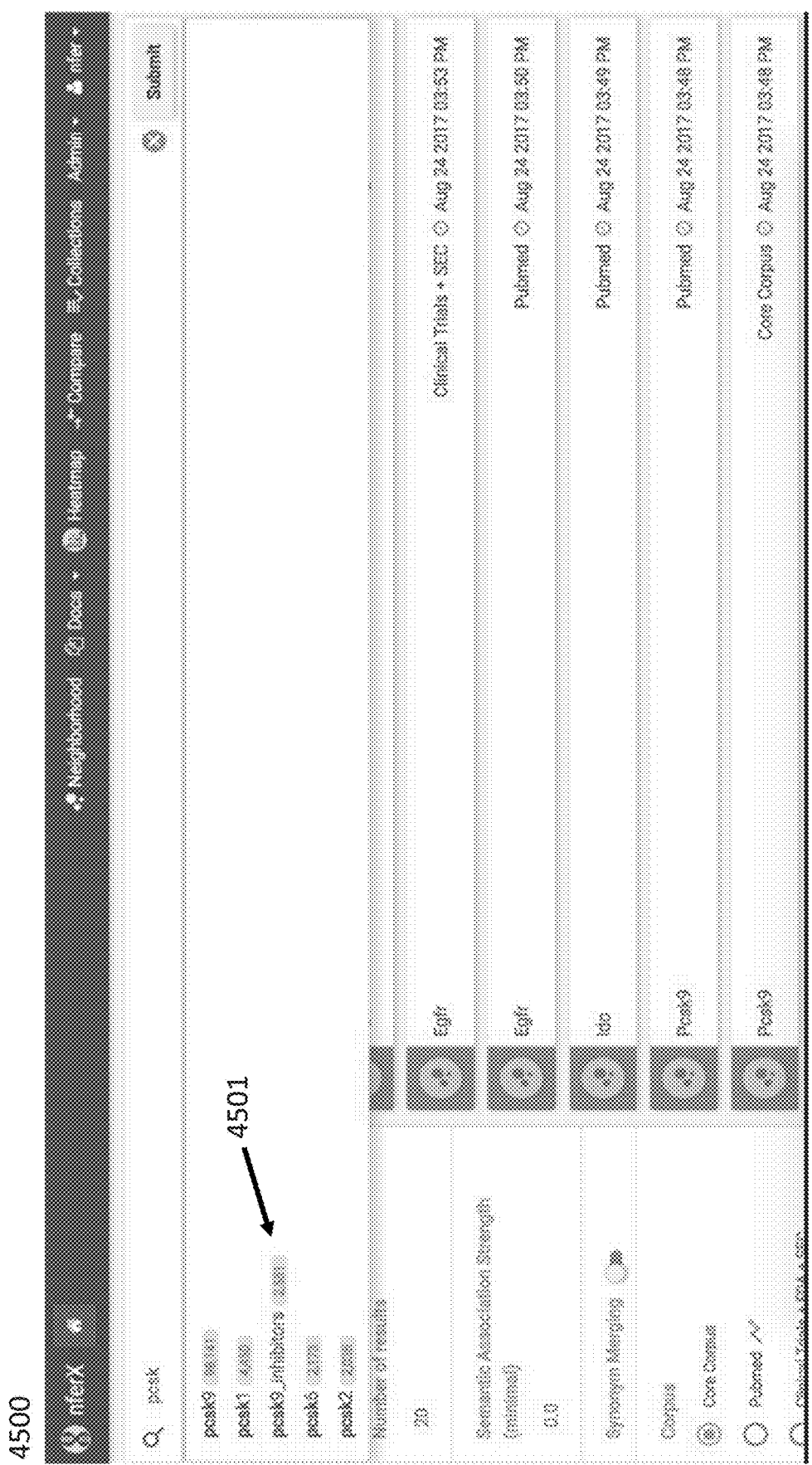
FIG. 45 illustrate an exemplary knowledge diagram interface in accordance with some embodiments of the present disclosure.

FIG. 45 illustrate an exemplary knowledge diagram interface 4500 in accordance with some embodiments of the present disclosure. The knowledge diagram interface 4500 can provide an autocomplete function 4501. When a user starts typing an entity in the query box, the autocomplete function 4501 can predict the entity and provide one or more suggestions. In some embodiments, each of the suggested entities can also include additional information, such as the number of occurrences each suggested entity occurs in the selected corpus.

Figure 46:
FIG. 46 illustrates an exemplary heatmap in accordance with some embodiments of the present disclosure.

According to some embodiments, a heatmap can provide a two-dimensional view of associations between multiple entities and identify relationships between them. FIG. 46 illustrates an exemplary heatmap 4600 in accordance with some embodiments of the present disclosure. The heatmap 4600 can show associations between genes (as listed on the y-axis) and drugs (as listed on the x-axis). In this example, the top row is for the gene "pd_1" and the other rows are other genes that are related to the gene "pd_1." These genes can be compared to a collection of entities that are FDA-approved drugs (which can include about 6,500 drugs). A subset of these drugs that have the highest sematic association strength with the gene "pd_1" can be selected and displayed as columns. Each cell in the heatmap can represent the semantic association strength between the corresponding row and column entities. In some embodiments, different colors and/or different gradients of colors can be used to represent various semantic association strengths. A color legend 4603 can map a color (or a gradient of color) to a semantic association strength. The heatmap 4600 can uncover various relationships between entities. For example, in the first row, one can observe that nivolumab and pembrolizumab are drugs that bind pd_1, and "pd_1" is most strongly associated with these drugs, as compared to other drugs. In some embodiments, the heatmap 4600 can include an average 4601 and/or a standard deviation 4602 of the semantic association strength for each row.

Figure 47:
FIG. 47 illustrates an exemplary heatmap in accordance with some embodiments of the present disclosure.

FIG. 47 illustrates an exemplary heatmap 4700 in accordance with some embodiments of the present disclosure. In this example, the top row represents the drug "rituximab," and the other rows represent other drugs that are associated with the drug "rituximab." These drugs are compared to a collection of disease entities (which can include about 9,500 diseases). A subset of these diseases that have the highest semantic association with the drug "rituximab" can be selected and displayed as columns. Similar to the heatmap 4600, every cell value can represent the semantic association strength between the pair of entities (i.e., between a pair of the drug and disease that are represented at that cell). The heatmap 4700 can reveal that not only the indications where rituximab is currently used (i.e., various subtypes of Lymphoma), but also indications that are seemingly "off-label" including Lupus Nephritis (highlighted).

Figure 48:
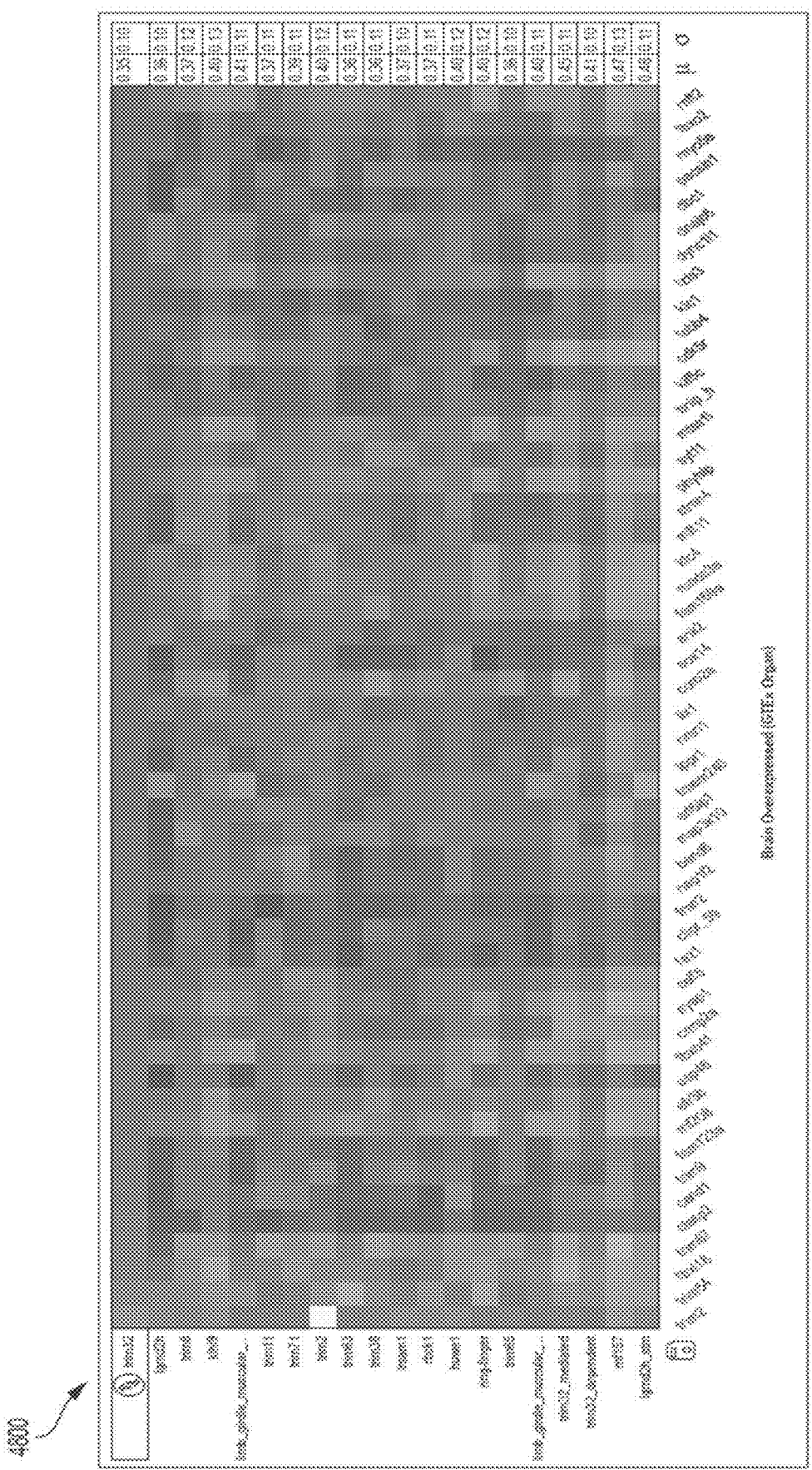
FIG. 48 illustrates an exemplary heatmap in accordance with some embodiments of the present disclosure.

FIG. 48 illustrates an exemplary heatmap 4800 in accordance with some embodiments of the present disclosure. The heatmap 4800 can incorporate molecular analytics. In this example, the top row represents the gene "TRIM32," and the other rows represent the other genes that are associated with the gene "TRIM32." These genes are compared to a collection of entities that represent genes that are specifically overexpressed in human brain tissues obtained from the GTEx database. This can represent a unique comparison that combines knowledge synthesis with molecular analytics related to expression of genes in the human brain. In this example, TRIM32 has a very high association to genes that are expressed specifically in the brain. This can be seen by TRIM32 having high mean semantic association strengths across the columns. The gene "TRIM2" also connects very strongly to TRIM32, and TRIM2 itself is highly expressed in the brain.

Figure 11:
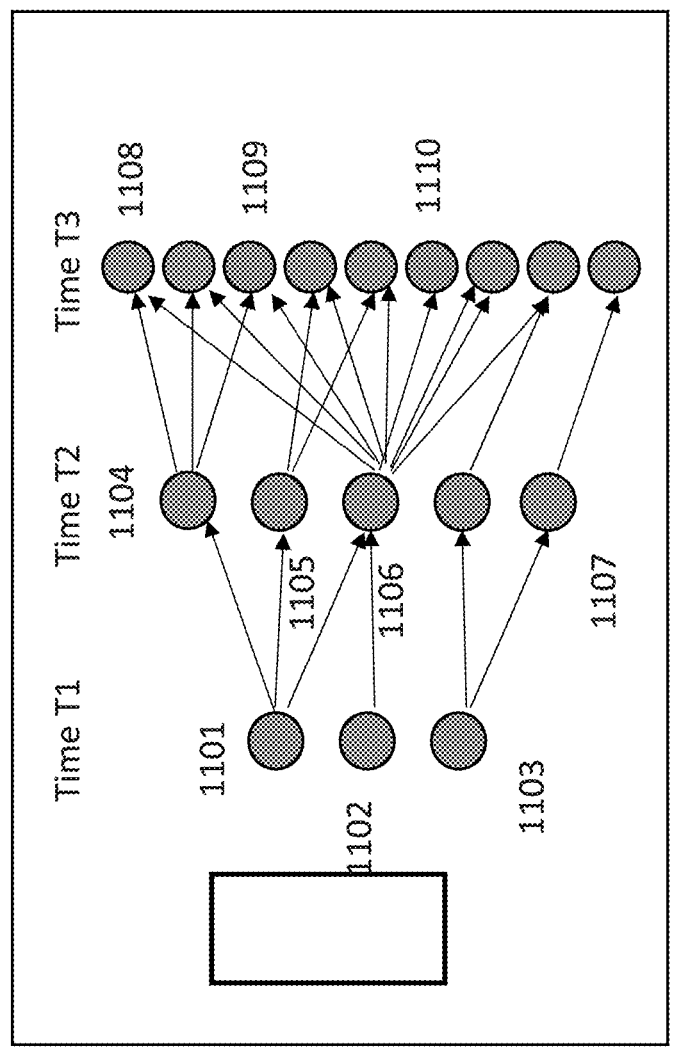
FIG. 11 illustrates entity distribution for a search input where the neighborhood nodes change with time in accordance with some embodiments of the present disclosure.

FIG. 11 illustrates entity distribution for a search input where the neighborhood nodes change with time. In FIG. 11, each time slot (T1, T2, T3) illustrates the new nodes that emerged at that timestep (for the purpose of illustration). The transform 1102 can be used to vary the time ranges, etc. The matrix can capture entity neighborhood change with time and can also indicate how a node 1101 relates to other nodes in the subsequent time step (1105 and 1106). For example, for a term like "dropout," a key method to avoid overfitting in machine learning models, can be used in the context of many neural net models, subsequent to the success of this technique, resulting in a large fanout as illustrated with node 1106. In addition to terms that relate to each other by actual co-occurrence in the input corpus used to construct the Knowledge graph, entities that are in the neighborhood that are not co-occurring, but are semantically related (1109 and 1110 in black) can also be identified by this process. While these semantically related entities may have false positives, these entities generate a candidate class for potential insights that would have otherwise been difficult to find out by ocular perusal of neighborhood sets across time.

Figure 12:
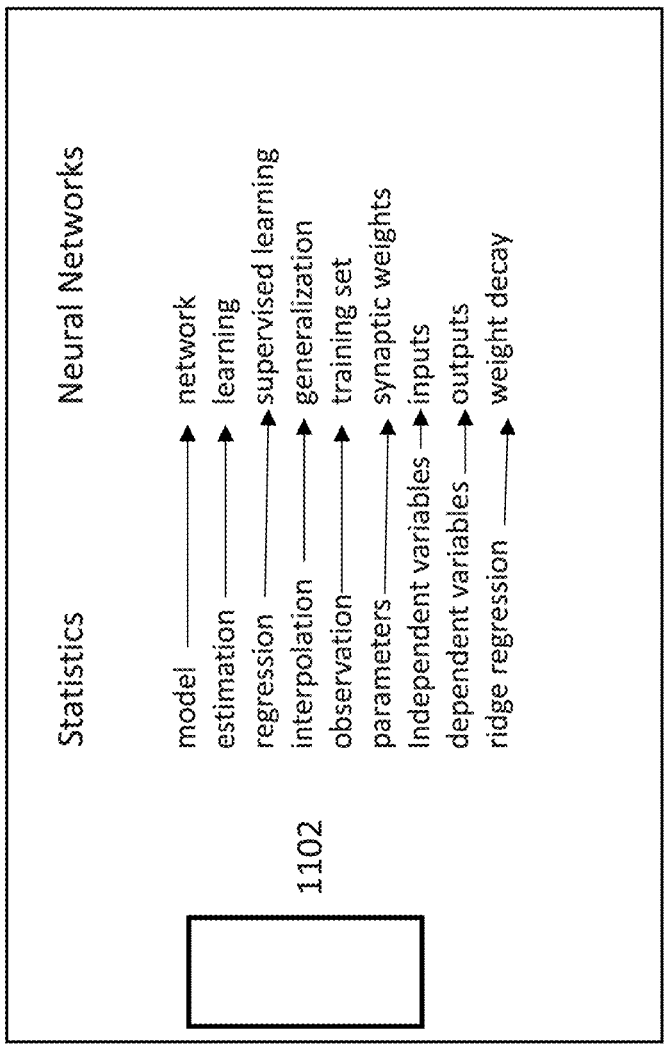
FIG. 12 illustrates an instance of output the temporal progression of concepts across entity classes in accordance with some embodiments of the present disclosure.

FIG. 12 illustrates an instance of output the temporal progression of concepts across entity classes. In the illustration, the entities in the neighborhood of entity class "statistics" can be compared with entity class "neural networks," where the filter/transform 1102 can be used to compare entity class statistics at a time that precedes the entity class for neural networks, and where an entity class is a label to a set of entities. The filter/transform 1102 can be used to alter the date/time ranges to compare the neighborhood change of entity with time. FIG. 12 also illustrates the evolution of entities representing the same concept from the space of "statistics" to "neural networks" space. For an equivalent case from the biological space, the entity distribution in Knowledge graph neighborhood of drug cenicriviroc changes before and after 2014. Before 2014, the entity distribution is dominated largely by "anti-viral" drugs belonging to the drug class "ccr5 antagonists". However, post 2014, the entity distribution in Knowledge Graph neighborhood for the same drug shows the emergence of "liver related diseases" such as NASH (non-alcoholic steato hepatitis).

Figure 13:
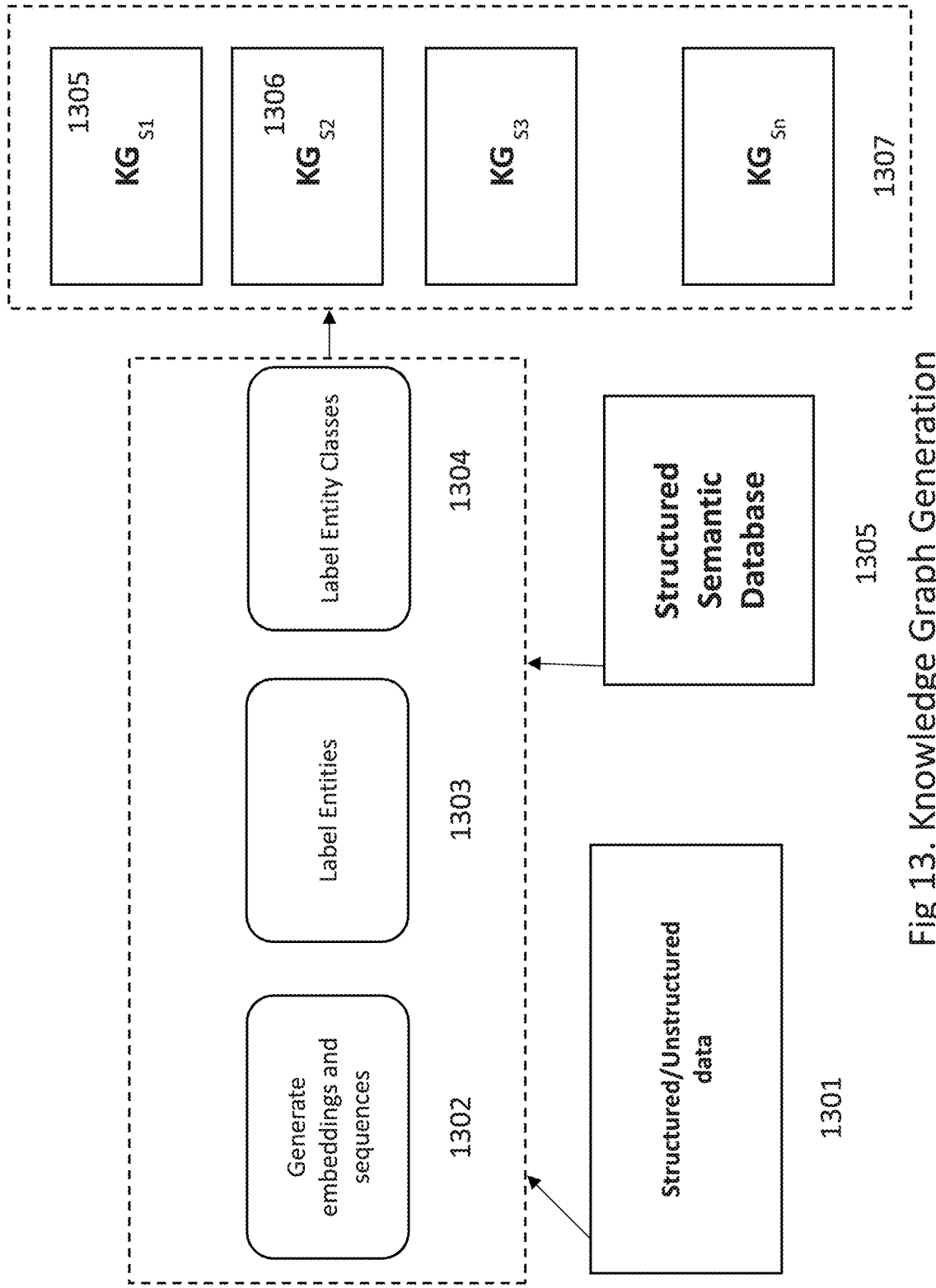
FIG. 13 illustrates the creation of an instance of Knowledge graph subsets at an instant of time in accordance with some embodiments of the present disclosure.

FIG. 13 illustrates the creation of an instance of Knowledge graph subsets at an instant of time. A structured/unstructured data snapshot 1301 at an instant of time can be used to generate word, sentence, and document embeddings 1302, which in turn are used to create label entities 1303, and collection of labels 1304. Embeddings can be generated by unsupervised methods like word2vec, doc2vec and also using sequence learning models like RNNs. These terms/phrases from this process can then be labeled as entities and entity classes, where structured semantic database 1305 can also used. Furthermore, this process can also yield candidate entities and entity classes that have not been labeled with a priori knowledge. This can be done making use of entity distribution of unlabeled entities and the asymmetry of neighborhood between pairwise entities. For example, even though term1 and term2 have one cosine distance measure, the ordering of neighborhood terms of term1 and term2 are asymmetric. This asymmetric nature can also yield different entity distributions and different entity rankings. Thus, term1 can be a medicine that comes as a neighbor of term2, but not vice versa. Also term2 can have as its neighbors more entity classes, which term1 may not. These types of asymmetries can be used to identify candidate new entities and entity classes. The output of this process can be a knowledge graph of labeled entities and entity classes and unlabeled entities. The knowledge graph store 1307 can be a store of a universal as wells as domain and sub-domain knowledge graphs, where a single entity (either labeled or unlabeled) can have different entity distributions.

Figure 14:
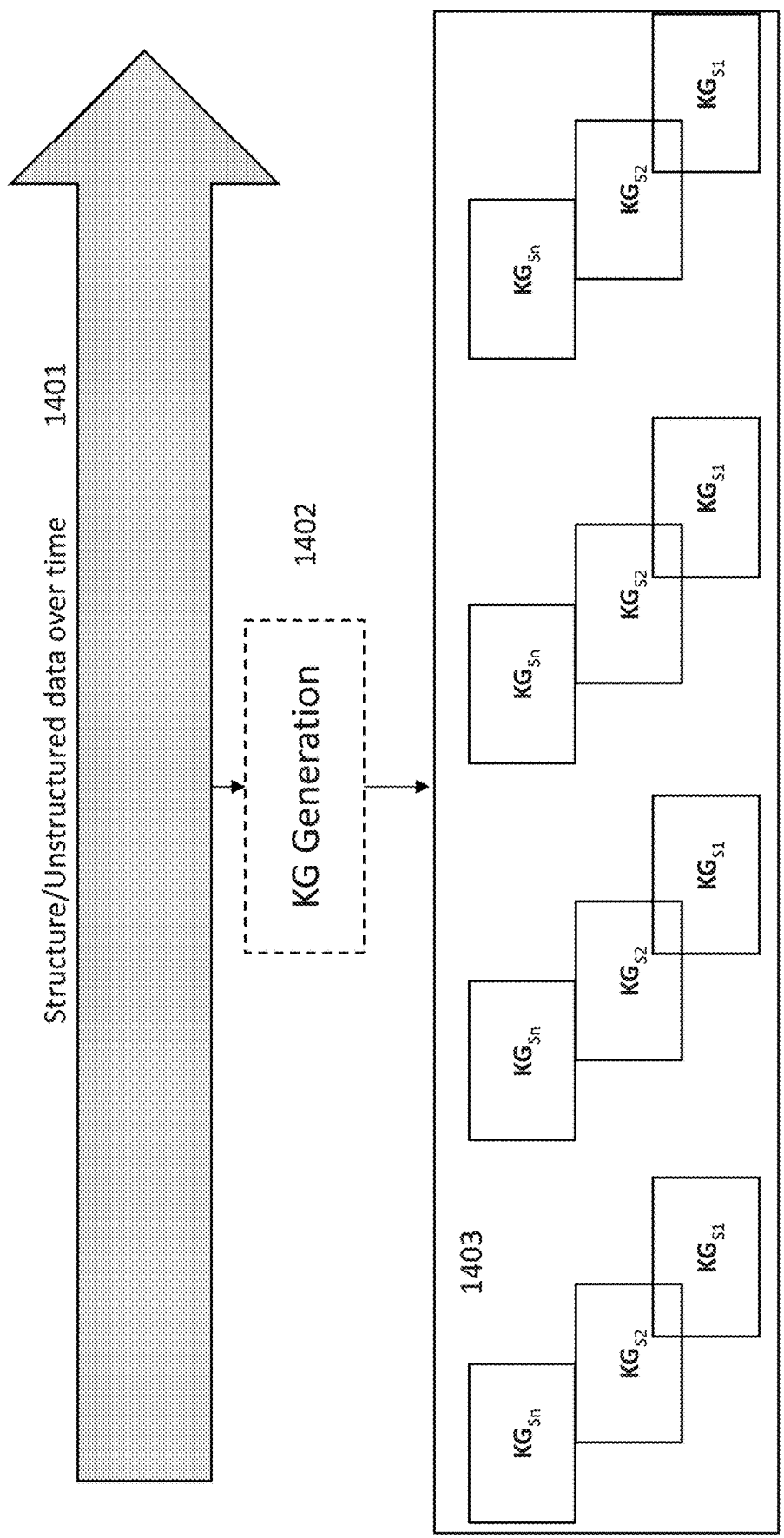
FIG. 14 illustrates the capturing of temporal progression of entities and consequently entity distribution over time in Knowledge Graph ("KG") in accordance with some embodiments of the present disclosure.

FIG. 14 illustrates the capturing of temporal progression of entities and consequently entity distribution over time in Knowledge Graph ("KG") as knowledge graph snapshots for subset spaces (KGS1 . . . Sn) [1403] accrued over time, from structured and unstructured data 1401 by the knowledge graph generation process 1402.

Figure 57:
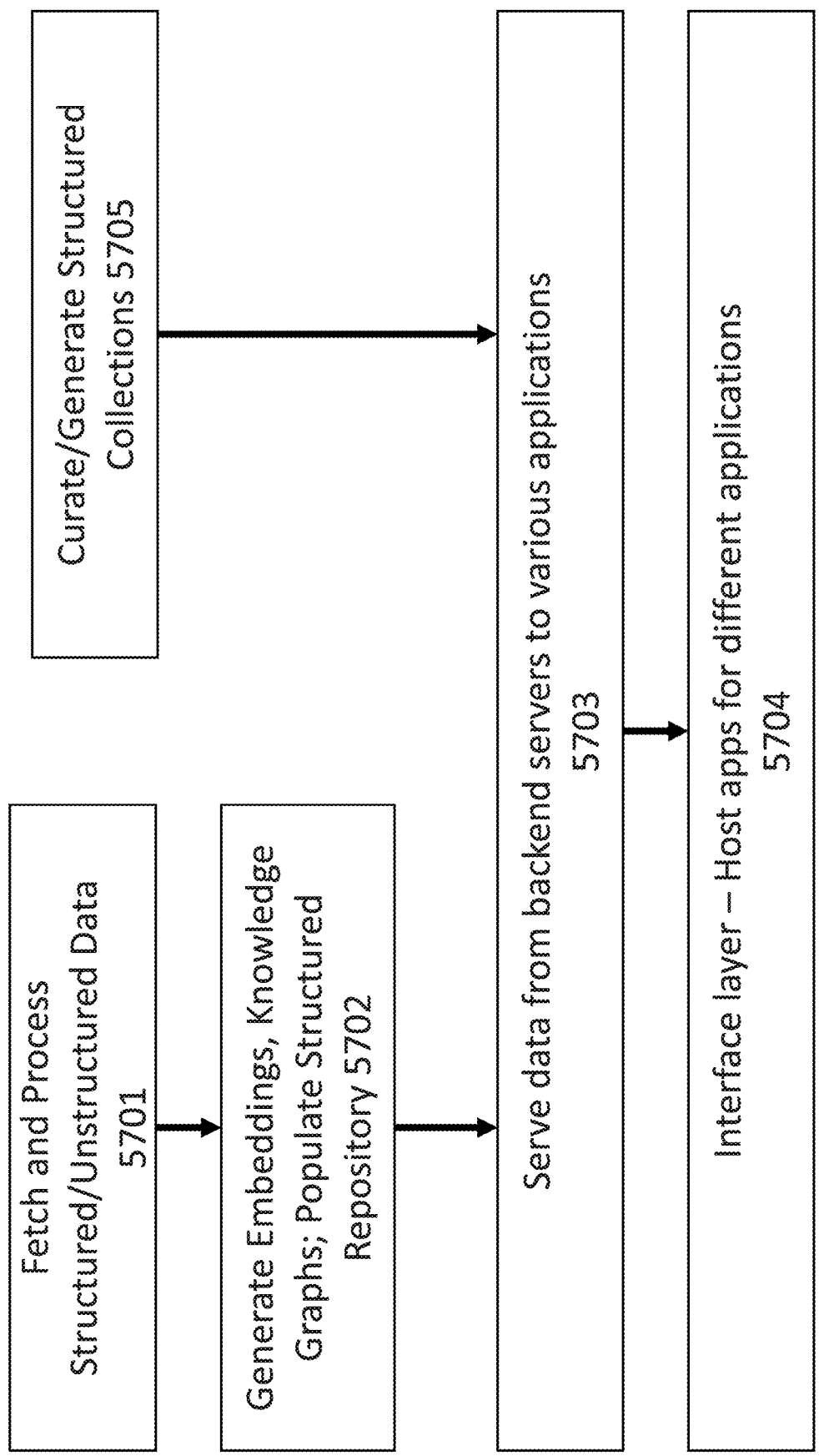
FIG. 57 illustrates a data flow in accordance with some embodiments of the present disclosure.

FIG. 57 illustrates a data flow in accordance with some embodiments of the present disclosure. In some embodiments, structured and/or unstructured data can be fetched and processed by the system described in FIG. 1 (5701). The processed data can be used to generate word/sentence embeddings and/or knowledge graphs (5702). The processed data can also be used to populate a structured database (5701). Different assets from 5701 and 5702 can be served through different backend servers/computer systems catering to different applications (5703). For example, word embeddings can be hosted by word vector servers (5703) and cater to downstream applications, such as a neighborhood app, which can generate neighborhood sense diagram (5704). Sense embeddings can be hosted by an Adagram server/computer system and cater to sense embedding app (5704). Word embeddings can also be used to generate heatmap data for a Heatmap app (5704). Moreover, word embeddings can cater to temporal analysis app (5704). Concurrent to this data flow, collections can be created and hosted in backend servers/computer systems. The curation of collections can be performed locally by leveraging off structured and/or unstructured data (5702). The curation of collections can also be performed remotely by anyone who wishes to enrich a particular domain of interest by curated/automatically created collections (5705). These collections can then be hosted on backend servers (5703). Alternatively, the backend servers can be a proxy to remotely hosted collections.

Figure 58:
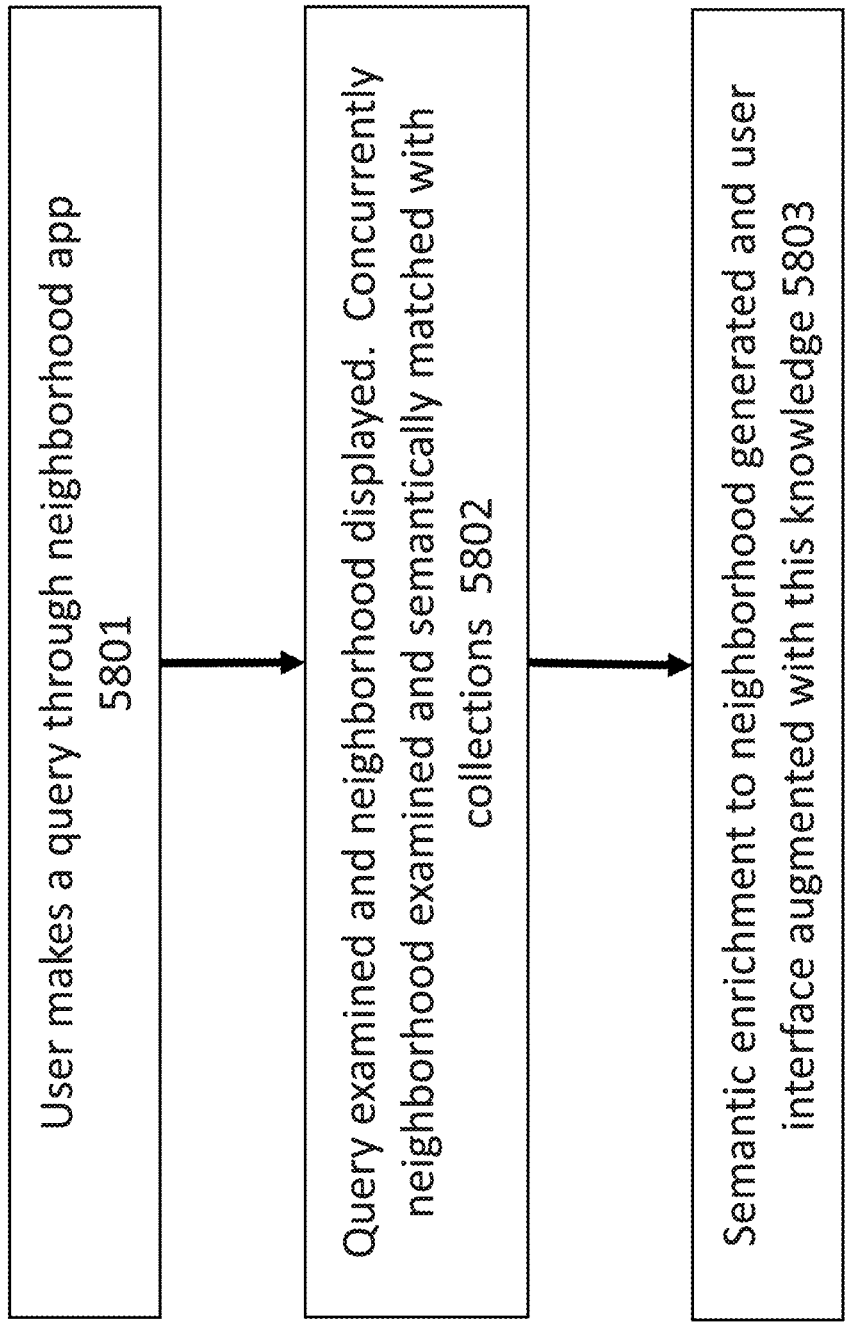
FIG. 58 illustrates a control/data flow when a user makes a query request to a neighborhood app in accordance with some embodiments of the present disclosure.

FIG. 58 illustrates a control/data flow when a user makes a query request to a neighborhood app (5801) in accordance with some embodiments of the present disclosure. The neighborhood app can provide a user interface, where the user can enter a query term and the neighborhood app can generate different neighborhood senses associated with the query term. The user interface can look similar to FIGS. 31-32. In some embodiments, if the user query is a gene, the neighborhood (5802) of that page would most likely contain gene entities and perhaps other related entities like diseases, drugs etc. In some situations, when the query term has multiple meanings, the neighborhood page would have entities semantically related to those different meanings. The sense embeddings serves to separate the senses to some degree. (See FIGS. 52-56.)

The semantic match with collections can generate an enriched representation through the knowledge synthesis (5803) and provide a broader/enriched view beyond just semantic neighborhood from word embeddings. For example, even if the neighborhood did not have any diseases associated with the gene, disclosed systems and methods can semantically match genes with disease collections associated with the query gene and show an enriched view that shows beyond just the semantic neighborhood. The matching of collections with the neighborhood can span from simple lexical matches to semantic matches with varying degrees of abstraction/separation. (See FIGS. 7-10.) For example, while a query about a gene can be enriched with gene collections, it can also be enriched by a related disease or even a collection involving people doing research on those genes. In some embodiments, the triangulation that picks candidate collections is not fixed, and is quite broad and varied (lexical to semantic match) offering a truly enriched experience beyond just neighborhood entities to a query. In some embodiments, the triangulation process can refer to mapping neighborhood results to entity collections that may be manually curated and/or machine generated. In some embodiments, a lexical match can refer to matching a search term with the name of a token collection. In some embodiments, a semantic match can refer to analyzing neighbors of the search term and entity types that are associated with the neighbors. In some embodiments, disclosed enriched synthesis boxes are distinct from existing search systems whose information augmenting results—even if semantic—are just clusters of the semantic results, or synopsis results. Disclosed systems and methods provide true enrichment by not only semantically matching neighborhood with collections but also enable the user in one interface to get a panoramic view of the semantic match information of the collections and the current page.

Disclosed systems, methods, and computer readable media can identify significant associations between life science entities at their incipient stages of knowledge creation, including prescient associations that predate seminal publications establishing those precise causal associations. In some embodiments, the system can also provide seamless incorporation of the growing repertoire of human curated entity collections, including custom entity collections that are subsets, supersets, or entirely novel sets of entities from across life science corpora. In some embodiments, the system can rely on pre-created and/or regularly updated corpora that are temporally sliced to various resolutions, enabling retrospective and near-real-time tracking of the temporal evolution in semantic association strength between life science entity pairs. In some embodiments, the system can readily make statistical inference of the specificity that may be attributed to each association based on the affiliated entity collections.

Disclosed systems and methods establish that the discovery of novel biological associations can be achieved through temporal analysis of the semantic neighborhood (e.g., in all documents found in PubMed) of a given pair of entities (words or phrases). These pairs can be of any entity type used in the Life Science literature (e.g., gene-gene or gene-disease) leading to hypothesis generation that can have a profound impact in strategic decision making. The complex set of phrases that constitute life science entities (e.g., diseases, genes) are often constituted of multiple words, and preserving such phrases is central to maximizing the value of Natural Language Processing (NLP) in the Life Sciences.

According to embodiments, temporal analysis of semantic association strengths or scores can enable identification of novel associations that predate or coincide with a seminal biological discovery published in the scientific literature.

The strong semantic association score signal can occur on the year of the seminal publication, or several years prior to such a seminal publication. Consequently, the semantic association scores (cosine distances) described herein can be used today to predict novel biological associations that have yet to be disclosed in the biomedical literature.

Disclosed systems and methods can identify and visualize, at the incipient stages, significant associations between life science entities (e.g., the gene EGFR is a life science entity). Sets of entities can be grouped into entity collections, which include but are not limited to the following: Biomolecules (e.g., genes, DNA or RNA polymers, proteins, lipids, metabolites, coding and non-coding RNA, peptides, antigens, mutations, etc.), Bio-entities (e.g., cells, organs, etc.), Diseases (e.g., Non small cell lung cancer, Rheumatoid Arthritis, Hypercholesterolemia, Multiple Sclerosis, Parkinson's disease, NASH, NAFLD, AIDS, Sepsis, etc.), Adverse Events, Microorganisms (e.g., *H. pylori*, Influenza H1N1 virus, Hepatitis C Virus, *Candida albicans*, etc.), Assays (e.g., High throughput cell screening, Kinome profiling, Growth inhibition, mass spectrometry, etc.), Companies/Institutions (e.g., pharmaceutical, biotechnology, CROs, diagnostics/device manufacturers, hospitals, clinics, universities, etc.), People (e.g., researchers/scientists, doctors/physicians, physician names, NPI IDs of physicians, executives, etc.), Phenotypes (e.g., in-vitro, in-vivo observable/measurable/subjective, etc.), Drugs (e.g., compounds/small molecules, antibodies, cells, etc.), Medical Instruments, Medical Procedures (e.g., surgery, transplantation, radiation etc.), and other entity collections that can be compiled by users of diverse Biomedical corpora (see FIG. 15). In some embodiments, the terms "knowledgebase" and "entity collection" are interchangeable.

Figure 15:
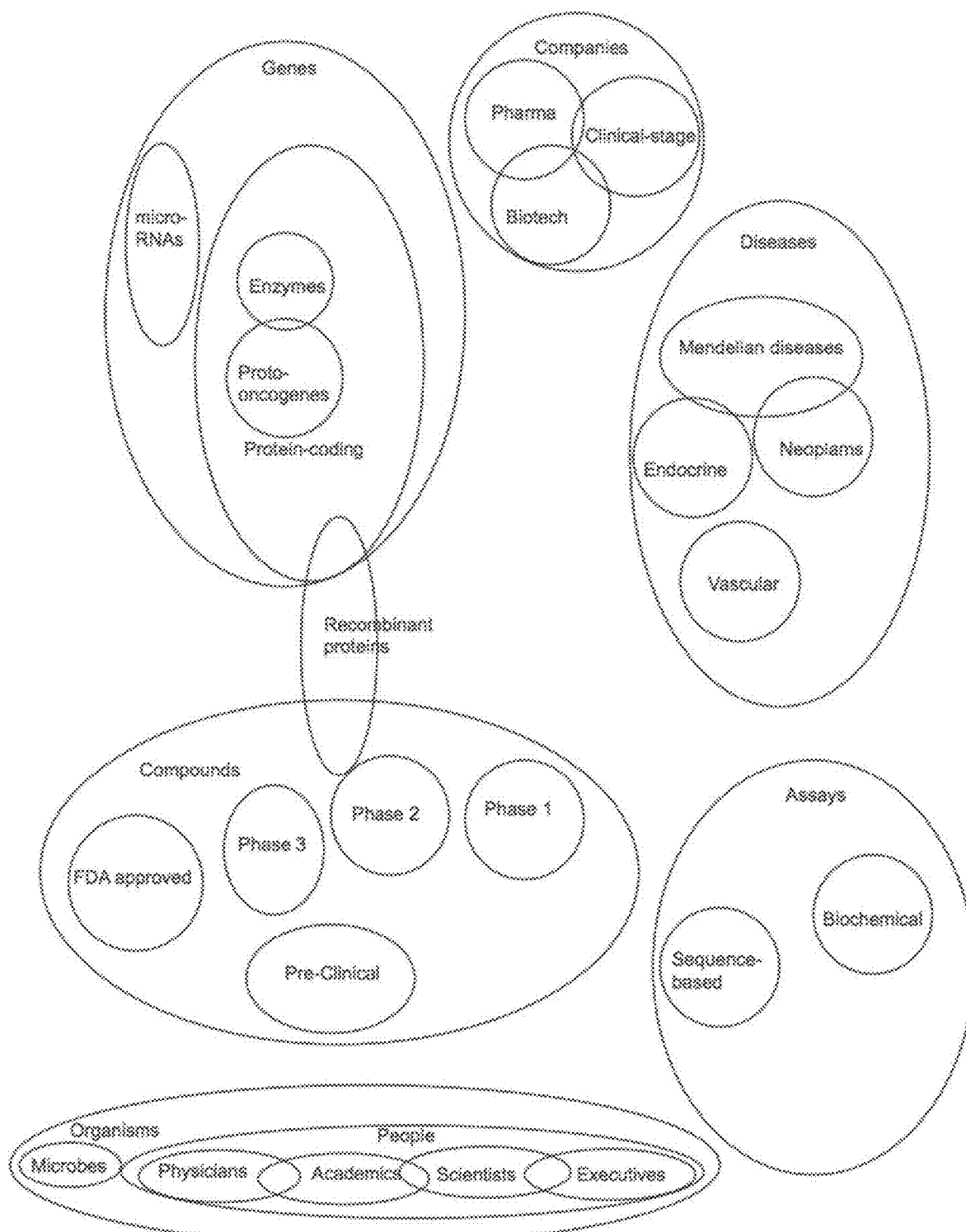
FIG. 15 illustrates exemplary entity collections in accordance with some embodiments of the present disclosure.

FIG. 15 illustrates exemplary entity collections in accordance with some embodiments of the present disclosure. FIG. 15 highlights super-collections that include several smaller sub-collections, as well as collections that overlap across multiple other entity collections in accordance with some embodiments of the present disclosure. The superset of all collections in the Life Science corpus itself may be construed as a "Master Entity Collection" (the collection of all collections and entities in the corpus). In some embodiments, custom collections that will be created by users of the system may also be labeled as Entity Collections. In the entity collection schematic visualized herein, diverse entity collections can be deposited, where entities can belong to multiple entity collections, and entity collections can be nested within one another or extend across other entity collections.

According to some embodiments, a set of industry specific entity collections can be created to provide a basis for the comparison of the evolution history of the "aggregated collection" against a singleton entity so that statistically robust inference can be made, for example, on the salience of the singleton entity's association with another entity over time.

Vector Space Models represent words in a continuous vector space where "semantically" similar words are mapped to neighboring points (i.e., such words are embedded nearby each other in a synthetic high-dimensional space). Such techniques have a long, rich history in the field of Natural Language Processing (NLP), but all methods depend in some way or another on the Distributional Hypothesis, which states that words that appear in the same contexts share semantic meaning. The different approaches that leverage this principle can be divided into two categories: count-based methods (e.g., Latent Semantic Analysis), and Predictive methods (e.g., neural probabilistic language models). Count-based methods compute the statistics of how often some word co-occurs with its neighbor words in a large text corpus, and then map these count-statistics down to a small, dense vector for each word. Predictive models directly try to predict a word from its neighbors in terms of learned small, dense embedding vectors (considered parameters of the model). Word2vec is a particularly computationally-efficient predictive model for learning word embeddings from raw text. It comes in two flavors: the Continuous Bag-of-Words model (CBOW) and the Skip-Gram model. (See Section 3.1 and 3.2 in Tomas Mikolov, Kai Chen, Greg Corrado, and Jeffrey Dean, Efficient Estimation of Word Representations in Vector Space, ICLR Workshop, 2013 ("Mikolov et al.")). Algorithmically, these models are similar, except that CBOW predicts target words (e.g., "mat") from source context words (e.g., "the cat sits on the"), while the skip-gram does the inverse and predicts source context-words from the target words. This inversion might seem like an arbitrary choice, but statistically it has the effect that CBOW smoothens over a lot of the distributional information (by treating an entire context as one observation). For the most part, this turns out to be useful for smaller datasets. However, skip-gram treats each context-target pair as a new observation, and this tends to do better for larger datasets, such as the gargantuan Life Sciences corpus summarized in Table 1 below.

TABLE 1

| Data Source | Data Type |
|---|---|
| Drugs@FDA (www.accessdata.fda.gov/scripts/cder/drugsatfda/) Drug marketing labels (full prescribing information) and associated FDA filings such as medical reviews, pharmacology reviews, and labeling revisions | Largely unstructured text |
| Clinical Trials (https://clinicaltrials.gov/) Phase 1, Phase 1/2, Phase 2, Phase 2/3, Phase 3, and Phase 4 clinical trial records: inclusion/exclusion criteria, trial purpose, trial arms, outcome measures, title, etc. | Semi-structured data sets |
| FDA Adverse Event Reporting System (FAERS) (https://open.fda.gov/data/faers/) Real World Evidence (RWE) of adverse event reports submitted to FDA by pharmaceutical/biotechnology companies, health care practitioners, and patients | Structured database |
| PubMed structured abstracts from the National Library of Medicine (NLM) (www.nlm.nih.gov/bsd/policy/structured_abstracts.html) Abstracts from the scientific literature published across journals cited in PubMed including GWAS studies, precision medicine efforts, clinical trial outcomes, etc | Largely unstructured text |
| PubMed Central (PMC) Open Access Full-text Papers (https://www.ncbi.nlm.nih.gov/pmc/tools/openftlist/) Complete scientific journal articles from the PMC Open Access (OA) papers | |
| Security and Exchange Commission (SEC) filings (www.sec.gov) SEC filings from pharmaceutical, biotechnology, and healthcare companies | Largely unstructured text |
| Wikipedia (www.wikipedia.org) Wikipedia articles | Largely unstructured text |

TABLE 1-continued

| Data Source | Data Type |
| --- | --- |
| Press Releases and Media Articles BusinessWire, STAT news, MedPage today, Xconomy, FierceBiotech, FiercePharma, and primary webpages of biotechnology, pharmaceutical, and medical device companies, CROs and regulatory agencies | Largely unstructured text |

According to some embodiments, the Biomedical corpora can include, but not limited to, data from one or more of the following sources: scientific literature (e.g., articles found in PubMed, PubMed Central—PMC Open Access, NCBI Bookshelf, etc.), clinical literature (e.g., records in clinical-trials.gov), regulatory literature (e.g., FDA documentation), and commercial literature (e.g., SEC filings, drug marketing information, drug prescription & transaction datasets, etc.). The exemplary sources of the Biomedical corpora are enumerated in Table 1. This corpus can be expanded and enhanced with various customer-supplied proprietary documents and/or public documents from across the Life Sciences ecosystem with the methods introduced herein. Examples of proprietary databases are Electronic Health Records (EHRs), Physician notes, Adverse event reports, etc. The formats of documents can include, but are not limited to, slide decks prepared or reviewed by scientists (e.g., presentations made in PowerPoint or Keynote), text files or spreadsheets with analyzed data (e.g., in TXT, CSV, XLS, or XLSX formats), or documents capturing scientific, medical, clinical, commercial or regulatory insights (e.g., in DOC, DOCX, PDF, or any other suitable formats).

As illustrated in FIG. 1 in accordance with some embodiments of the present disclosure, the system store 114 can capture information extracted from two or more source paths (e.g., 103a and 105a) in different forms to facilitate the synthesis of information and/or enable subsequent information extraction through different pathways (e.g., pathways 103a and 105a). In some embodiments, FIG. 1 includes the system store 114 that can be used to convert words into vectors and analysis of the resulting semantic BioKnowledge graph in accordance with some embodiments of the present disclosure. The system store 114 can include information stored in a structured semantic database 106 (which can be a traditional database); a knowledge graph(s) 107 (which can be directed graphs of labeled (extracted from both paths 101a and 102a) and/or unlabeled entities (extracted from the 102a path)); word embeddings 108 (which can include word(s) and/or sentence(s)); document/paragraph/sentence embeddings 109; and sequence representations of unstructured data 110. In some embodiments, an example of word embedding can be word2vec. In some embodiments, an example of document/paragraph/sentence embedding can be doc2vec. In some embodiments, an example of sequence representations 110 can be Memory Neural Network (MemNN).

According to some embodiments, the system in FIG. 1 can take as input structured data 101 (e.g., curated by humans), unstructured data 102 (e.g., raw text), and/or semi-structured data 117 (e.g., any combination of the structured and unstructured data). Examples of structured data is a table of name-value pairs, or a curated ontology of terms. Unstructured data can be just text (e.g., this very description). Structured and semi-structured data can go to 101a through a normalization and classification processes (103, 104) that merge them into the existing structured semantic database 106. In some embodiments, the normalization process can involve generating Resource Description Framework (RDF) triples (node A, node B, with an attribute edge connecting them). The normalization/classification can leverage 107a, 108a off the existing structured data 106 and embeddings 108 for merging. Unstructured data can go to 102a through a tokenization/normalization, which can involve, for example, cleaning up tokens. In some embodiments, tokens can be words and/or phrases that constitute input to a machine learning model. For example, the word "the" is a token. As another example, the words "new york" is a two-word phrase that can become one token by adding a special character (e.g.," ") as follows: "new_york." In some embodiments, text input can go through input processing, which converts the text into one or more tokens. In some embodiments, phrases can be created as tokens independently of prior knowledge outside given input. For example, when the words "New York" occur frequently in the input, "New York" can be converted into a phrase, which can then become a token as "New_York." In some embodiments, a plurality of words can become a phrase and/or a token even if they do not occur frequently in the input. For example, if the words "lung cancer" do not occur frequently in input, they can be forced to become a phrase and/or a token. In some embodiments, a known technique (e.g., Word2Phrase) can be used in the tokenization process. Specialized encoders may be used for handling the parsing of specific data sources 104a. Further still, phrases can be recognized/generated by analyzing a structured database in which such phrases exist as identified entities.

All the processed data can flow (103a, 105a) into a repository, such as the system store 114. This data along with models generated from this data 107, 108, 109, 110 can serve as the system store 114. Word and document embeddings 108 can include embeddings generated from both structured (converted to a text stream through specialized transformation) and unstructured data using models/tools, such as Word2vec, Adagram, Fasttext, doc2vec, and/or any other suitable model/tool. Incremental and temporal versions of embeddings can also be generated and stored in the system store 114. Sequence embeddings can be generated using Recurrent Neural Network (RNN) family of neural net models (e.g., bidirectional Long Short Term Memory (LSTM) networks). In addition to embeddings, other models can also be stored in this repository—such as the knowledge graph 107 and neural net models facilitating interactions (e.g., recurrent entity networks).

A sub-system 116 represents one embodiment of modules 111, 112, 115 facilitating interaction with the sub-system 113. Data can flow from the system store 114 to the sub-system 116 via paths 114a and 114b. Data can flow between the sub-system 116 and the sub-system 113 via a path 116a. While the system in FIG. 1 has been illustrated from an information flow perspective, some of the models can be trained end-to-end using the data in the system store as input and as labeled data (structured data used as labeled data). The word end-to-end can have the specific meaning that the parameters of the computational flow graph is trained end to end with one loss function. For example, a bi-directional LSTM encoder/decoder can be used with word embeddings 108, representing a language, and generate output in another language for an interactive application. The models in 114 and 116 can be generated by unsupervised, supervised, and/or reinforcement learning methods for a wide variety of discovery methods. Generative models (GANs) can also be used to create labeled data for tasks, where labeled data is sparse.

The system in FIG. 1 can also leverage traditional graph based algorithms taking as input word embeddings to find patterns that can compensate for absence of labeled data (e.g. entity distribution). The system can leverage off state of the art models adapting them to specific tasks and/or combining/augmenting them with traditional algorithms, one example of which is to compensate for absence of labeled data. The models can afford live or offline interaction with system through any of the interfaces 113.

The system depicted in FIG. 1 can include a processor(s) that is configured to implement the functionality described herein using computer executable instructions stored in temporary and/or permanent non-transitory memory. The processor can be a general purpose processor and/or can also be implemented using an application specific integrated circuit (ASIC), programmable logic array (PLA), field programmable gate array (FPGA), and/or any other integrated circuit.

The processor(s) can execute an operating system that can be any suitable operating system (OS), including a typical operating system such as any version or type of Windows, Mac OS, Unix, Linux, VXWorks, Android, Blackberry OS, iOS, Symbian, or other OS. The processor(s) can also execute any instructions from web-server related hardware and/or software.

Figure 16:
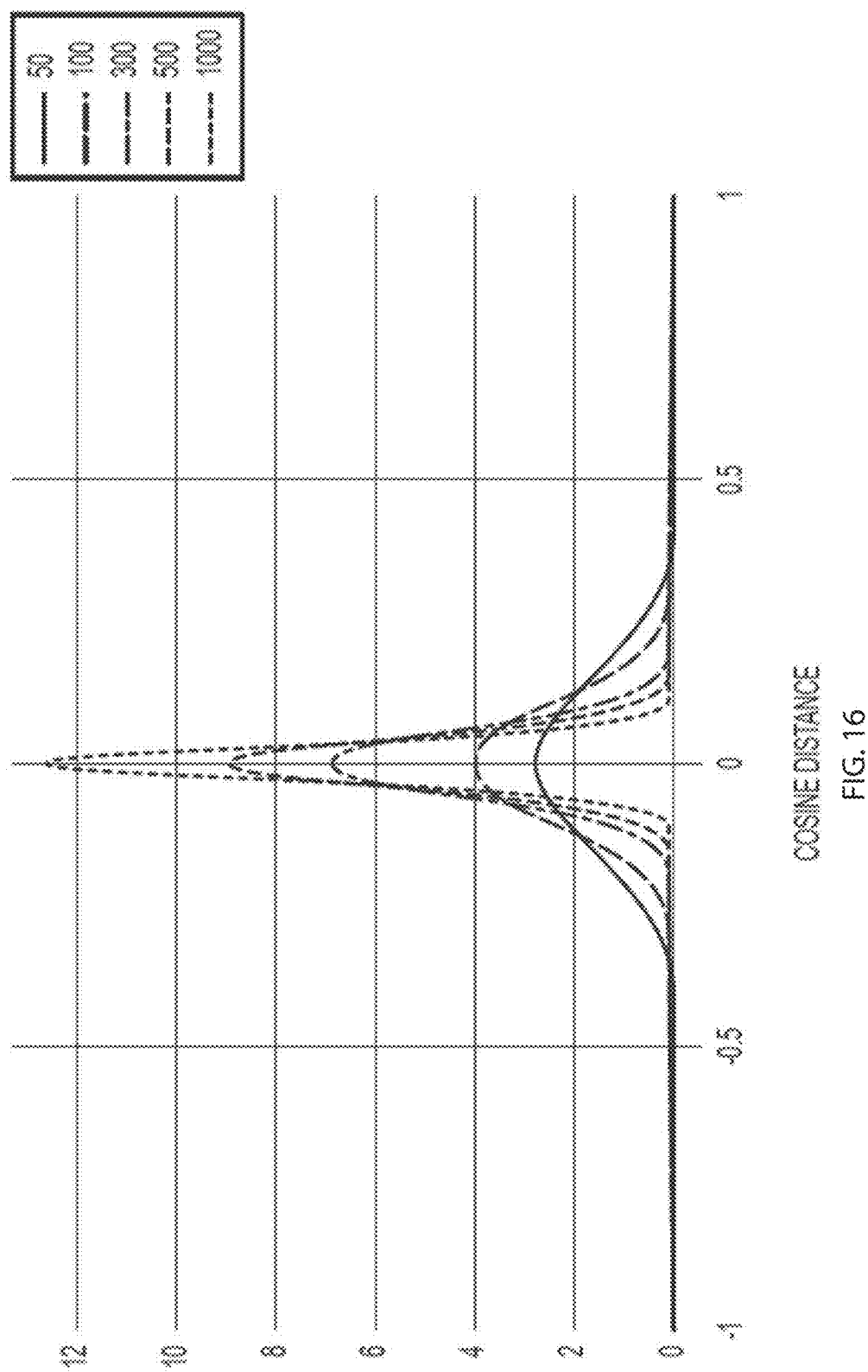
FIG. 16 illustrates a cosine distance probability density function (PDF) graph in accordance with some embodiments of the present disclosure.

FIG. 16 illustrates a cosine distance probability density function (PDF) graph in accordance with some embodiments of the present disclosure. The graph visually describes the implementation of a word2vec like Vector Space Model based on the system store 114. The system store 114 can result in a Semantic Bio-Knowledge Graph of nodes representing the words/phrases chosen to be represented as vectors and edge weights determined by measures of Semantic Association Strength (e.g., the Cosine Distance between a pair of word embeddings represented as vectors in a large dimensional space). The cosine distance ranges from 0 (representing no semantic association) to 1 (representing strongest association). This metric of association can reflect the contextual similarity of the entities in the Biomedical Corpora.

Figure 17:
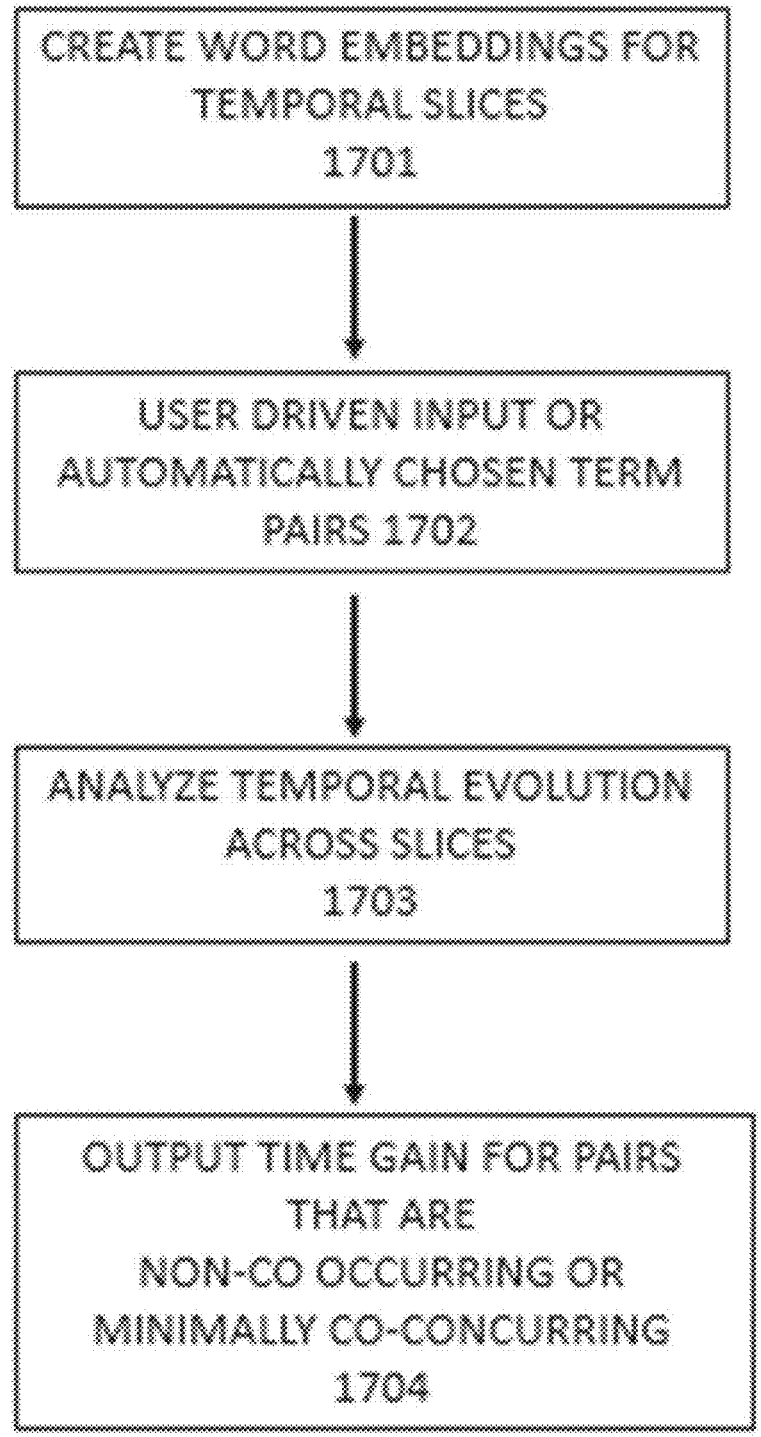
FIG. 17 illustrates a flow chart for temporal analysis in accordance with some embodiments of the present disclosure.

FIG. 17 illustrates a flow chart for temporal analysis in accordance with some embodiments of the present disclosure. Word/Phrase embeddings of temporal slices of documents can be created (Step 1701) as described in accordance with some embodiments of the present disclosure. Word embeddings can be generated by means that are not limited by the ways described herein.

In some embodiments, a time slice can represent a specific period of time (e.g., a month, a year, five years, a decade, a century, or any other period of time). Word embeddings can be generated for each time slice. For example, all journal articles published in a year can be taken as one time slice—e.g., science articles from 1996 belong to one time slice, science articles from 1997 belong to another time slice, and so on. In some embodiments, the terms "word embeddings" and "word vectors" are interchangeable.

In some embodiments, word vectors can be generated for each time slice separately or independently. In this case, word vectors for entities are initialized randomly and independently for each time slice during the training process in machine learning. For example, when creating word vectors for entities in science articles from 1996 and 1997, the time slice for the science articles from 1996 can be initialized independently of the time slice for the science articles from 1997. Thus, semantic associations that exist in 1996 do not affect semantic associations for 1997 because no word vector from 1996 was used in generation of the word vectors for 1997. This approach can be useful for analyzing semantic associations for each time slice independently.

In some embodiments, word vectors can be generated for each time slice by leveraging off word vectors from one or more of other time slice(s). In this case, when generating word vectors for entities for a time slice, word vectors from another time slice(s) are used to start off the training process in machine learning. For example, when creating word vectors for entities in 1997, the word vectors that were created for 1996 can be used to start off the training process. Thus, semantic associations from 1996 can affect semantic associations for 1997 because the word vectors from 1996 were used in generation of the word vectors for 1997. This approach can be useful for analyzing sematic associations for a time slice in view of semantic associations from another time slice(s).

In some embodiments, these other time slice(s) can be from a previous time slice(s). In some embodiments, word vectors can be generated from the entire corpus, where these embeddings can become the universe. In some embodiments, after word vectors are generated, disclosed systems and methods can analyze how the semantic neighborhood of a term changes over time.

Once embeddings of time slices are generated, term pairs can be chosen either automatically or by user (Step 1702). In the automatic case, for instance, candidate pairs can be chosen from a combination of entity types, such as gene x gene, gene x disease, or any other suitable combination of entity types. In some embodiments, the candidate set can be culled by picking those that occur either infrequently or do not occur at all in a time slice. These candidates, in contrast to highly co-occurring pairs, can be potential pairs for prediction. These pairs can then be analyzed (Step 1703) across time slices. In some embodiments, one method includes a novelty measure that varies across time and the cosine distance between the two terms. This analysis can yield as its output (Step 1704) items for which the system can predict that these terms will likely be associated stronger in future. The novelty measure can bring to the fore term pairs that occur infrequently or do not occur together at all, thereby enabling the discovery of potential links between term pairs that could strengthen over time slices, and are candidates for time gain prediction. For term pairs that have a high co-occurrence in the time slices examined, disclosed systems and methods can perform a retrospective causal path study between two terms.

In order to study the evolution of concepts quantitatively, it is important to understand the behavior of the semantic association strength metric. The metric and the statistical properties of the metric are described under the Null hypothesis in order to make stronger statements on the semantic association strength's salience that arises from disclosed systems and methods. In some embodiments, the word embedding (d-dimensional vector representation of a word or phrase in the corpus under consideration) generated by the Unsupervised Neural Network can be compared to another by using the dot product (or inner product). The dot product between two vectors a and b is defined as:

$$a \cdot b = \|a\| \|b\| \cos \theta$$

where $\|a\|$ and $\|b\|$ are the respective magnitudes (also termed L2 norm) of the vectors, and $\cos \theta$ is the cosine distance with a value ranging from $-1$ to $1$. The objective function used by the Neural Network is formulated in such a fashion as to bring together the words that co-occur in a local sliding window. That is, the angle between such pair of words will be closer together, and the cosine distance will be higher.

One of the behaviors exhibited by the Neural Network is to cluster words that are semantically close to each other. In a corpus containing a diverse set of entities ("classes" of words such as Genes, Diseases, Companies, Drugs, People, etc.), words of the same entity type tend to have high cosine distances compared to a randomly chosen pair of words. Hence, one question that repeatedly shows up while investigating word associations is the statistical significance of a particular cosine distance observed between a pair of word vectors. Towards assessing the statistical significance, we first formally analyze the nature of cosine distances that can be observed in a d-dimensional space consisting of word vectors that are distributed uniformly. To declare a certain word pair association as significant would entail that the cosine distance of that pair should be highly unlikely to have been generated by the above random distribution.

Let us choose a vector v on the d-dimensional unit sphere (d-sphere that lives in $R^d$). We want to compute the probability that another vector w randomly chosen from the unit sphere has cosine distance x from v. All the vectors can be assumed to be uniformly distributed in the d-sphere. We have a random variable, the angle between the vectors, and a random variable $X = \cos\theta$, the cosine of the angle $\theta$ between the randomly chosen w and the fixed vector v. For example, the 3-dimensional space (d=3) can be analyzed. In a unit sphere, an arbitrary unit vector v can be fixed. The vectors which are at angle $\theta$ from v all live on a circle of radius $\sin\theta$ (the plane of this circle is at a distance $\cos\theta$ from the center of the sphere—see FIG. 15). To compute the probability that the vector w has an angle $\theta$ with respect to vector v, we need to know the fractional area of the sphere where w will live. In the 3-dimensional space, such a fractional area is nothing but the product of the circumference of the specific circle (which has a radius $\sin\theta$) and a small differential $\Delta\theta$ $$\left(\lim_{\Delta\theta \to 0} \Delta\theta = d\theta\right).$$

The probability is then $$\frac{2\pi \sin\Theta d\theta}{4\pi}.$$

For the general case of a d-dimensional space, these vectors will live in a (d-1)-sphere of radius $\sin\theta$. Let $A_d(r)$ denote the surface area of a d-sphere. Examples: $A_2(r) = 2\pi r$, $A_3(r) = 4\pi r^2$. The fractional area of the is $A_{d-1}(\sin\theta)d\theta$ and the probability that the angle is $\theta$:

$$f_\Theta(\Theta)d\theta = \frac{A_{d-1}(\sin\Theta)d\theta}{A_d(1)} \propto (\sin\Theta)^{d-2}d\theta \quad \text{(Eq. 1)}$$

In the above equation, the proportionality holds, since a d-sphere of radius r has a surface area proportional to $r^{d-2}$. Changing variables from $\theta$ to x: Let $x = \cos\theta$ and hence $$\sin\Theta = \sqrt{1-x^2} \quad \text{(Eq. 2)}$$

$$dx = -\sin\Theta d\theta \Rightarrow |d\theta| = \frac{|dx|}{\sin\Theta} = \frac{dx}{\sqrt{1-x^2}}$$

-continued

From Eq. 1, $f_X(x)dx \propto \left(\sqrt{1-x^2}\right)^{d-2} \frac{dx}{\sqrt{1-x^2}}$ $\Rightarrow f_X(x)dx \propto \left(\sqrt{1-x^2}\right)^{d-3} dx$ $f_X(x) = \frac{\left(\sqrt{1-x^2}\right)^{d-3}}{Z}, -1 \leq x \leq 1$ where $Z = \int_{-1}^{1} \left(\sqrt{1-x^2}\right)^{d-3} dx$ Eq. 2 gives the probability density function of the cosine distance distribution.

FIG. 16 illustrates the probability density function (pdf) for the various N-dimensional space in accordance with some embodiments of the present disclosure. In some embodiments, the typical dimensionality used by a neural network is 300. As can be seen in the graph, the distribution is highly peaked with most of the mass centered around 0—that is, a randomly chosen pair of vectors typically are orthogonal or close to orthogonal (angle is close to $$\frac{\pi}{2}).$$

The following Table 2 shows the probability of observing vector pairs having a certain cosine distance and the expected number of random vectors for various cosine distances.

TABLE 2

| Cosine distance | p-value | Expected number of random vectors above the cosine distance |
|---|---|---|
| 0.90 | 5.538751e−111 | 1 |
| 0.85 | 2.302365e−86 | 1 |
| 0.80 | 1.939344e−69 | 1 |
| 0.75 | 9.426968e−57 | 1 |
| 0.70 | 9.109259e−47 | 1 |
| 0.65 | 1.152092e−38 | 1 |
| 0.60 | 5.855381e−32 | 1 |
| 0.55 | 2.457876e−26 | 1 |
| 0.50 | 1.389285e−21 | 1 |
| 0.45 | 1.493984e−17 | 1 |
| 0.40 | 3.933236e−14 | 1 |
| 0.35 | 3.061398e−11 | 1 |
| 0.30 | 8.135050e−09 | 1 |
| 0.25 | 8.253500e−07 | 40 |
| 0.20 | 3.493872e−05 | 1678 |
| 0.15 | 6.638752e−04 | 31867 |
| 0.10 | 6.040020e−03 | 289921 |

For example, at a cosine distance of 0.9 (approx. angle 26°), the probability is exceedingly tiny at $5.5 \times 10^{-111}$, and even at a larger cosine distance of 0.3 (approx. angle) 73°), the probability is small at $8.1 \times 10^{-9}$. In some embodiments, a typical corpus that is encountered in a disclosed system tends to have several million words/phrases. Consequently, the conventional belief of using the random distribution (e.g., cosine distribution) will give very good p-values, resulting in flagging too many associations as statistically significant. One way to make the interpretation of associations tighter is to compare the expected number of random vectors above the observed cosine distance with the actual number of vectors above that cosine distance. The third column of Table 2 shows the expected number of random vectors for various cosine distances. As an example, on a core corpus with 48 million vectors, for several Life Science entities such as Genes, Diseases, Drugs etc., we typically have 50K+ vectors above a cosine distance of 0.3. In such cases, it can be a logical basis to use the ratio of expected random vectors to observed actual vectors as a measure of statistical significance. When assessing statistical significance of closely related entities (such as Gene/Gene or Gene/Disease associations), a higher bar may be needed for credibility.

In some embodiments, statistical interpretation of the significance of association strength between a pair of entities involves multiple covariates, including but not limited to the number of documents, the source of documents, and the entity collections that contain the pair of word embeddings. The resulting association metric can be tracked over time, allowing for a temporal inference of the relationship between two Life Sciences entities and establishing the statistical significance of such a relationship. A number of examples listed below illustrate that a high semantic association strength pre-dated the eventual seminal publications that firmly established the relationship between the two entities. This notion can be captured as "Time Gain," which can represent the amount of time (e.g., years) between the emergence of the "semantic signal" (i.e., an increase in Semantic Association Strength) and the actual occurrence of the association in the primary literature (i.e., an increase in documents reporting the association).

This methodology can be used to identify specific pairs and networks of statistically significant entity associations. Analyzing semantic association strength over time (i.e., performing Temporal Analysis) can discover and track nascent seminal associations from corpora, such as the Life Science corpora. Temporal Analysis can compare two entities, such as Life Sciences entities, by tracking their semantic association strength over time. In some embodiments, more than two entities can be compared. For example, if there are entities A, B, C, and D, then these entities can be compared pair-by-pair in an order—such as A-B, then B-C, then A-C, then A-D, then B-D, then C-D, etc. Life Sciences entities can be classified de-novo or defined using pre-existent classification schemes found in the scientific literature. In the latter case, structured databases can be leveraged to determine entity classes. For example, genes can be derived from NCBI's Gene Records (https://www.ncbi.nlm-.nih.gov/gene) and/or the HUGO Gene Nomenclature Committee data set (https://www.genenames.org). Similarly, disease names and ontologies can be obtained from the Medical Subject Headings (MeSH) collection (https://meshb.nlm-.nih.gov).

Once entity types are determined, their association strength in the Biomedical Corpora can be tracked over time. Entities can be first generated by a phrase generation process, where the candidate entities are selected not only by the standard measure of their occurrence/co-occurrence of the n-gram words composing them, but also by forcibly choosing candidates obtained from a dictionary compiled from structured collections. The standard measure can be a Pointwise Mutual Information (PMI) measure. This can ensure a phrase is generated even if the occurrence counts do not satisfy the thresholds for becoming a phrase. This can be of particular value in temporal slices, where the vocabulary may not be large enough and occurrence/co-occurrence of terms constituting an important phrase may not be sufficient.

In some embodiments, the phrase generation process can use the vocabulary generated for any time slice as part of the preserved word list of the subsequent time slice. This can ensure terms that occur in a time slice can be tracked from that point onwards regardless of the counts of the individual terms constituting a phrase being low. The first step of the cascading can use a corpus vocabulary that is combination of all the corpora text, increasing the likelihood of important phrases being preserved in time slice training despite the low occurrence of individual terms constituting the phrase. The phrase generation process can also ensure that the count of the constituent terms of a phrase are at least as many as the phrase count itself. This can ensure that during the training, all the phrases and their constituent terms can participate in the training process, individually and as composites.

The training process can generate word vector embeddings by iterating through the corpus generated above. Word embeddings can be generated for each time slice that is then used for temporal analysis and comparison of entities over time.

The training process can perform two forms of generation of vectors. In one form, the word vectors of every slice is initialized randomly, and the vector embeddings are learnt during training. This form of training is useful to see how a particular term evolved relative to another term independent of its past. In the second form of training, every time slice is instantiated prior to training by the embeddings of the previous instance. This can be particularly useful to see how a term evolved over time.

The entity type of each term in a time slice can be evaluated for that time slice using an entity type distribution computation, constrained to that corpus. This can enable the tracking of a term's semantic meaning over time. For instance, the neighborhood of a term may change with time, causing its entity type distribution to change with time. This method can enable tracking of entity type distribution change over time.

For each time slice, causal pathways that brought two terms together can be analyzed by examining a training graph generated by keeping track of words that occur within the training window. This training graph overlaid on the trained cosine distance graph can provide the causal explanation for words coming together at different levels of indirection.

Within the Temporal Analysis plots, certain markers associated with nascent associations can be identified. A sharp increase in Semantic Association Strength that precedes an increase in documents containing both entities can be a clear signal that the system can predict seminal associations before they are reported in the literature. The increase in Semantic Association Strength can be captured as a maximum of the second-derivative of the curve, whereas the increase in the document count can be captured by looking at the slope of the curve in a fixed axis or through crossing of a pre-specified document count threshold. Repeated Time Gain cases for known seminal associations validate disclosed systems and methods as having predictive capabilities. Life Sciences entity pairs that have a high Semantic Association Strength today with no documents with both of them occurring can be flagged as potentially novel and seminal associations.

Nascent Life Sciences entity associations that are detected can be further characterized by their features that can be found in various proprietary and/or public datasets. For example, for gene entities, their expression in normal human tissues can be determined by using a dataset, such as the GTEx dataset from the Broad Institute (https://gtexportal.org/home/), and correlate that to their Semantic Association Score. Similarly, gene and disease associations can be stress-tested for novelty by determining their association score in database, such as the OpenTargets database (https://wwww.targetvalidation.org/), which should be low for our predicted nascent Life Sciences entity pairs.

Statistical Interpretation

Multiple factors can affect the association between two entities. When comparing two entities, the entity collection to which each entity belongs can affect the Semantic Association Strength. Furthermore, each entity has a different distribution of Semantic Association Strength when being compared to a given entity collection.

Figure 18:
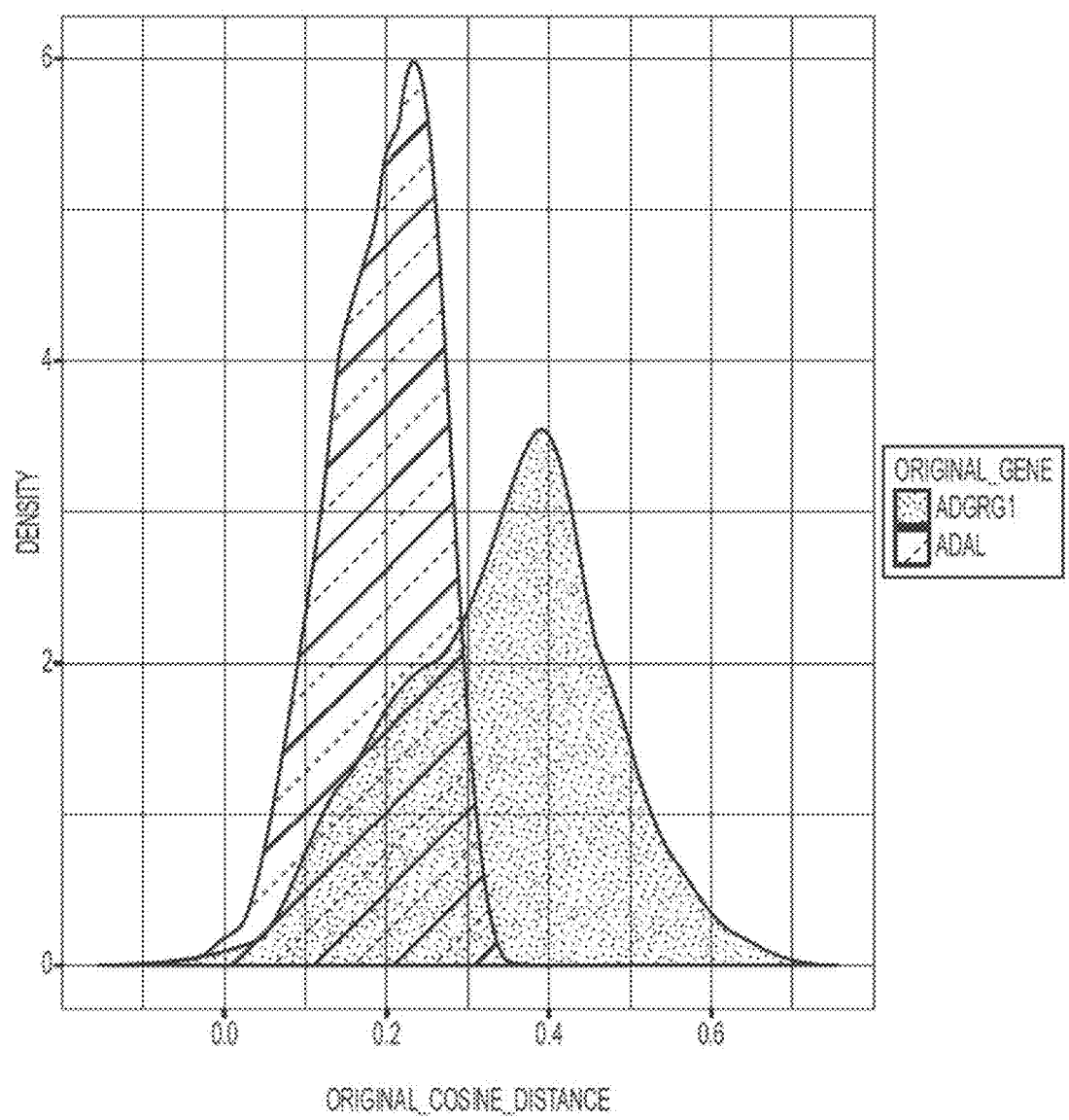
FIG. 18 illustrates a density distribution of semantic association strength for two genes against all disease entities in accordance with some embodiments of the present disclosure.

FIG. 18 illustrates a density distribution of semantic association strength for two genes against all disease entities in accordance with some embodiments of the present disclosure. The semantic association strength (cosine distance on the x-axis and probability density function on the y-axis) can be measured for genes, such as ADAL and ADGRG1, against some or all disease entities. The two distributions can be different. For example, FIG. 18 illustrates that the distributions for ADAL and ADGRG1 are different. When comparing the gene ADGRG1 to all disease terms in an entity collection of diseases, the distribution of Semantic Association Strengths has a mean of 0.34 and a standard deviation of 0.13. On the other hand, when comparing the gene ADAL to the same collection of disease terms, the distribution of Semantic Association Strengths has a mean of 0.19 and a standard deviation of 0.067. On average, one would expect that majority of gene-disease associations to be noise rather than representing causal links. In some embodiments, because the distribution of Semantic Association Strengths for a given entity class varies depending on the entity queried, this effect should be accounted for in attempting to draw statistical inferences.

Figure 19:
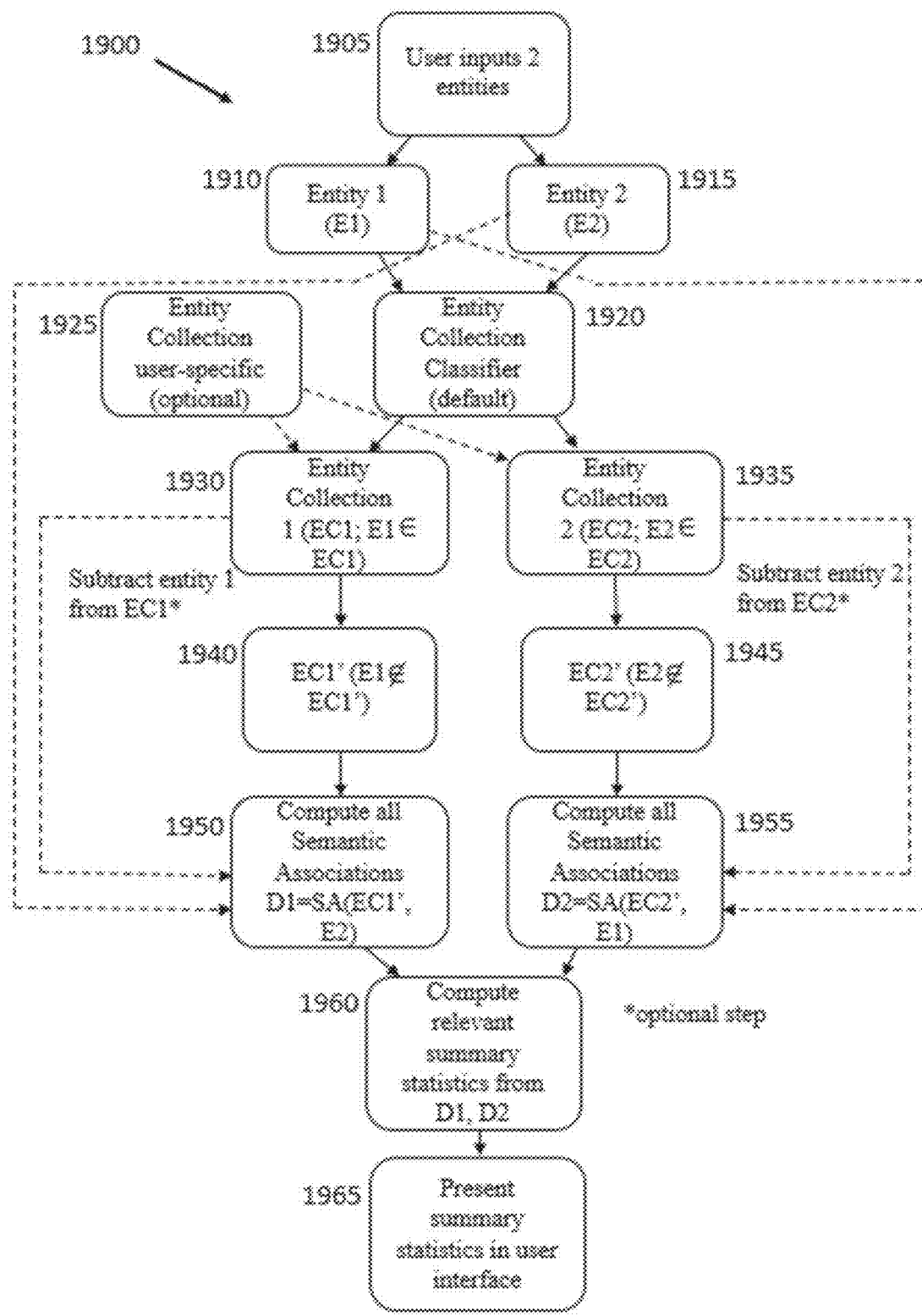
FIG. 19 illustrates a process for evaluating statistical background model and presenting summary statistics to user in accordance with some embodiments of the present disclosure.

Disclosed systems and methods can aid users in interpreting their queries by providing a measure of the background model of the semantic association strength for a query of the type they are entering. FIG. 19 illustrates a process for evaluating statistical background model and presenting summary statistics to user in accordance with some embodiments of the present disclosure. A user can input two entities E1 and E2 for comparison (Steps 1905, 1910, 1915). A suitable entity collection (e.g., the most relevant entity collection) to which E1 and E2 each belong can be computed by default, or the user can specify the entity collection to be used for each entity in the query (Steps 1920, 1925). The two selected entity collections can be defined as EC1 (length $n_1$) and EC2 (length $n_2$) for E1 and E2, respectively (Steps 1930, 1935). E1 can be subtracted from EC1 to generate a new entity collection called EC1'. (Step 1940). The same operation can be performed on EC2 to generate EC2' (Step 1945). The Semantic Association Strength between E1 and all members of EC2' (containing $n_2$-1 members) can be computed to generate a vector $D_2$ with length $n_2$-1. The Semantic Association Strength can also be computed between E2 and all members of EC1' (containing $n_1$-1 members) to generate vector D1 (Steps 1950, 1955).

The vectors D1 and D2 represent the distribution of Semantic Association Strengths for all queries of type E2×EC1 and E1×EC2, respectively. These distributions can be useful for the purpose of using as a background (null) model for statistical inference of significant associations. To aid in this statistical inference, summary statistics such as the mean of D1 and/or D2 can be computed and presented to the user (Steps 1960, 1965). These summary statistics include, but are not limited to the mean, median, percentiles, and p-values. More complex functions can also be presented. One such function can be the area to the right of the probability distribution function of random draws from D1 and D2. In this equation, one views points from D1 and D2 as random variables (d1 and d2). The sum of these random variables is defined as a new random variable h (Equation 1). The probability distribution function of h can be computed as the convolution (*) of D1 and D2. The observed Semantic Association Strength of E1×E2 ($SASE_{E1 \times E2}$) is drawn from D1 and D2, thus the statistic of merit ($p_{conv}$) is the proportion of random draws from D1 and D2 that exceed twice $SASE_{E1 \times E2}$.

$$h = d1 + d2$$

$$pdf(h) = D1 * D2$$

$$p_{conv} = \int_{SAS_{E1 \times E2}}^{\infty} pdf(h) dh$$

Figure 20:
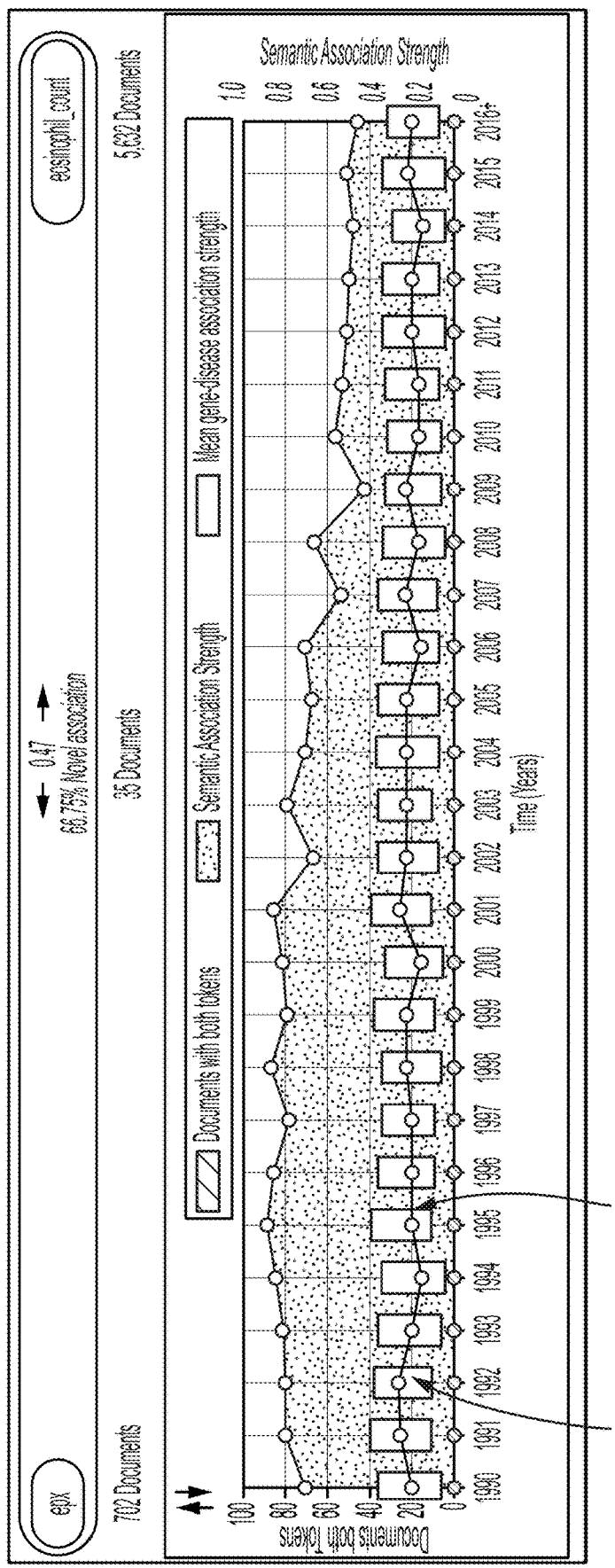
FIG. 20 illustrates an example of summary statistics overlayed with temporal analysis in accordance with some embodiments of the present disclosure.

FIG. 20 illustrates an example of the display of these summary statistics overlayed with temporal analysis. In this example, the gene "EPX" is queried against the disease entity "eosinophil_count." Summary statistics—including the mean (line 2001), $25^{th}$ percentile and $75^{th}$ percentile (box 2002) of the semantic association strength for all queries of type EPX vs disease_entity—are presented for each year presented in the temporal analysis. Summary statistics include, but are not limited to, the mean, median, percentiles, and p-values. The number of documents containing both entities is also shown for each year.

Novelty Measure

One of the interesting properties of the high dimensional vector space produced by the Neural Network is the clustering of certain vectors, whose corresponding phrases have not co-occurred in the corpus even once. This is counter intuitive at first sight: the optimization criteria used to train the Neural Network relies on maximizing the probability of words occurring with a small local sliding window. The vectors corresponding to the words in a sliding window are typically brought together as part of the back propagation process—that is, more frequently two words occur together in a sliding window, it would be natural to expect a high cosine distance between that pair of vectors. However, one principle used in the training process (also called as Negative Sampling or Noise Contrastive Estimation), explicitly minimizes the cosine distance between frequently occurring words (e.g., common English words, such as "the," "of," "to," etc.) and other words in the sliding window. The net result of the above can enable two words that have not co-occurred even once (or have co-occurred very few times) to still have a high cosine distance. Such an association can be termed as a "Novel Association," as the association between such pair of words is strong (i.e., high cosine distance) despite the lack of evidence in the primary literature.

Figure 21:
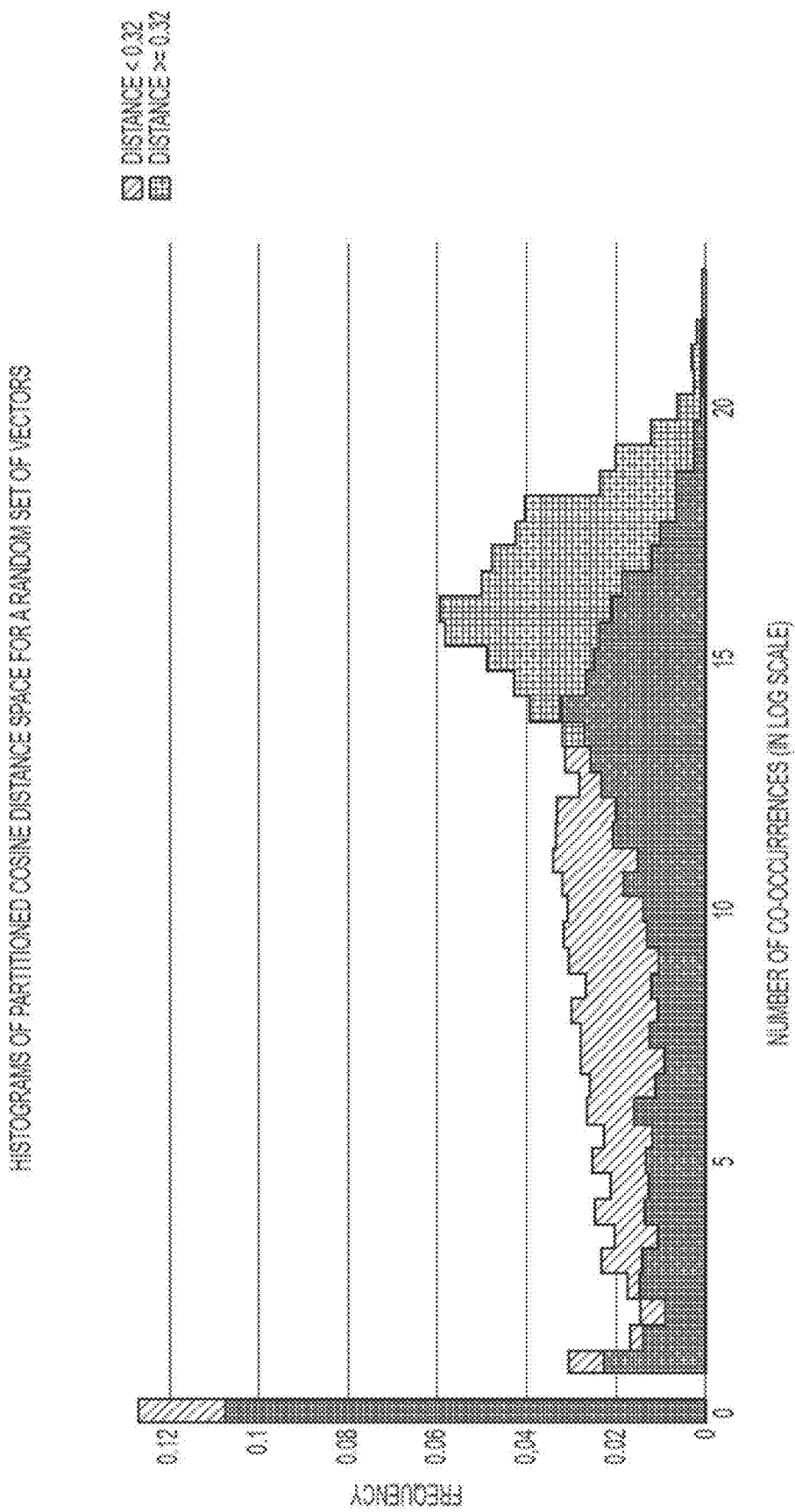
FIG. 21 illustrates two histograms generated from a random set of vectors in accordance with some embodiments of the present disclosure.

FIG. 21 illustrates two histograms generated from a random set of vectors (in vector space generated by the Neural Network) where one distribution (denoted as "DISTANCE<0.32") represents all vector pairs whose cosine distance is less than 0.32 (deemed "not strong associations") and the other distribution (denoted as "DISTANCE>=0.32") represents all vector pairs whose cosine distance is greater than 0.32 (deemed "strong associations"), in accordance with some embodiments of the present disclosure. This can show how common a phenomenon it is to find word vector pairs that have very good cosine distances but yet not co-occur even once in the corpus. The "DISTANCE>=0.32" bar at zero value suggests that roughly 11% of vector pairs whose cosine distances where greater than 0.32 ("strong associations") never occurred together even once in a document. It is also clear from the figure that albeit more of the mass of the "DISTANCE>=0.32" distribution is skewed to the right as expected (more co-occurrences and hence unsurprisingly larger cosine distances), there is a long tail of the "DISTANCE<0.32" distribution (very high co-occurrences but small cosine distances). The long tail is a direct consequence of negative sampling—where vectors corresponding to common words that co-occur quite often with significant words in a sliding window are moved away from vectors of the other words.

According to some embodiments, a quantitative metric can be provided to measure Novelty based on Pointwise Mutual Information (PMI). The PMI measures the strength of association between two random variables X and Y as follows:

$$pmi(x; y) = \log \frac{p(x, y)}{p(x)p(y)},$$

where p(x) and p(y) are the probabilities of random variables X and Y, and p(x, y) is the joint probability of X and Y.

Let $w_1$ and $w_2$ be the number of occurrences of words 1 and 2 respectively. Let $w_c$ be the number of co-occurrences of words 1 and 2 in a corpus of size T.

$$pmi = \log \frac{\frac{w_c}{T}}{\frac{w_1}{T}\frac{w_2}{T}}$$

$$pmi = \log \frac{w_c T}{w_1 w_2}$$

We constrain the pmi values between 0 and 1 by using the logistic function (sigmoid) and additionally use exponential damping to disfavor very large co-occurrence counts. The rationale is that the larger the co-occurrence count $w_c$, we expect the Neural Network to bring the vectors together and the damping helps to account for that artifact.

Taken together, we define the novelty measure as follows:

$$\text{novelty} = e^{-\alpha w_c} \frac{1}{1 + e^{pmi}},$$

where α is the damping coefficient (e.g., typically set to 0.01). A novelty of 1 (or 100%) indicates that $w_c$=0. The novelty measure should be carefully interpreted in conjunction with the cosine distance, as it is possible to have a good novelty score and yet have a weak cosine distance. In some embodiments, a typical practice is where we tend to interpret the novelty as 0 below a certain threshold cosine distance (e.g., approx. 0.3 would make a good choice in 300 dimensional space of a 50 M word corpus, as it represents the distance above which there is utmost one random vector and that too with a very small probability).

Figure 22A:
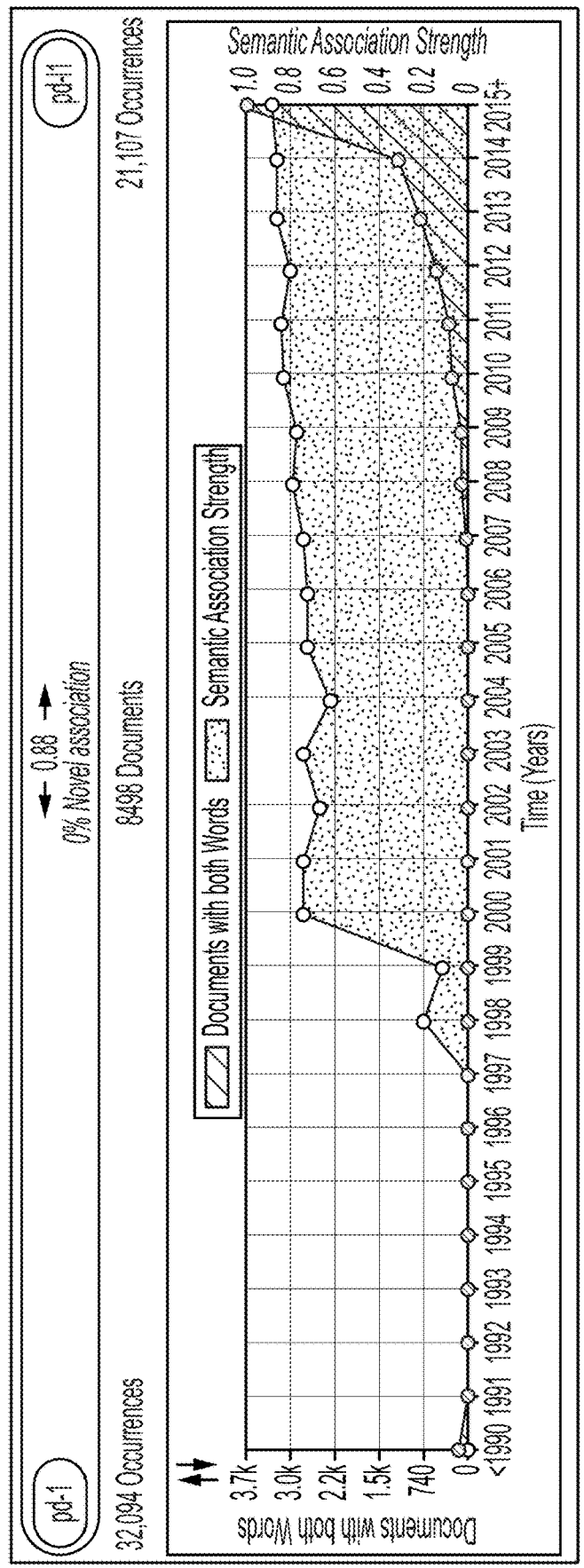
FIGS. 22A-B illustrates temporal analysis of bona-fide Life Sciences entity pairs in accordance with some embodiments of the present disclosure.
Figure 22B:
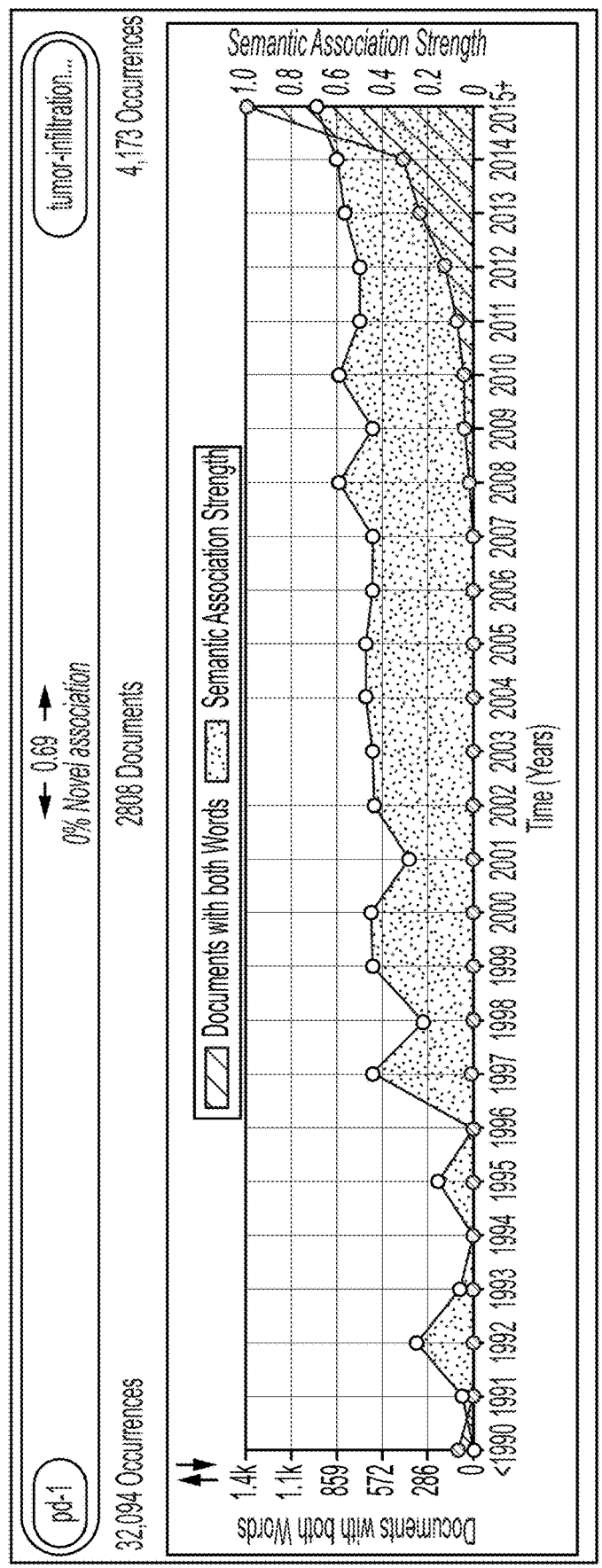

In some embodiments, temporal analysis can reveal seminal associations in the Life Sciences before the major publication describing them was released. FIGS. 22A-B illustrates temporal analysis of bona-fide Life Sciences entity pairs in accordance with some embodiments of the present disclosure. These figures illustrate how the semantic association strength (Cosine Distance) between a pair of Life Sciences entities is plotted over time (in years) for the PubMed corpus (denoted by "Semantic Association Strength" in the legend) along with the document co-citations count (denoted by "Documents with both Words" in the legend). As noted earlier, the document co-citations curve (denoted by "Documents with both Words" in the legend) does not provide any "predictive" edge and purely reflects the accumulating number of articles that discuss both words. However, bona-fide biological associations (pd-1: pd-l1∥pd-1: tumor-infiltrating lymphoyctes) have strong semantic associations even when the knowledge around these genes was nascent. Specifically, the Semantic Association Scores for these pairs were suddenly and significantly increased around the 1997-2001 time-frame, when papers co-citing the words (pd-1: pd-l1∥pd-1: tumor-infiltrating lymphocytes) had not appeared yet. This result showcases why the Semantic Association Strength (Cosine Distance) between a pair of Life Sciences entities captures the temporal evolution of concept associations in a highly sensitive fashion (when the knowledge was nascent and only reported by a handful of articles).

Figure 23:
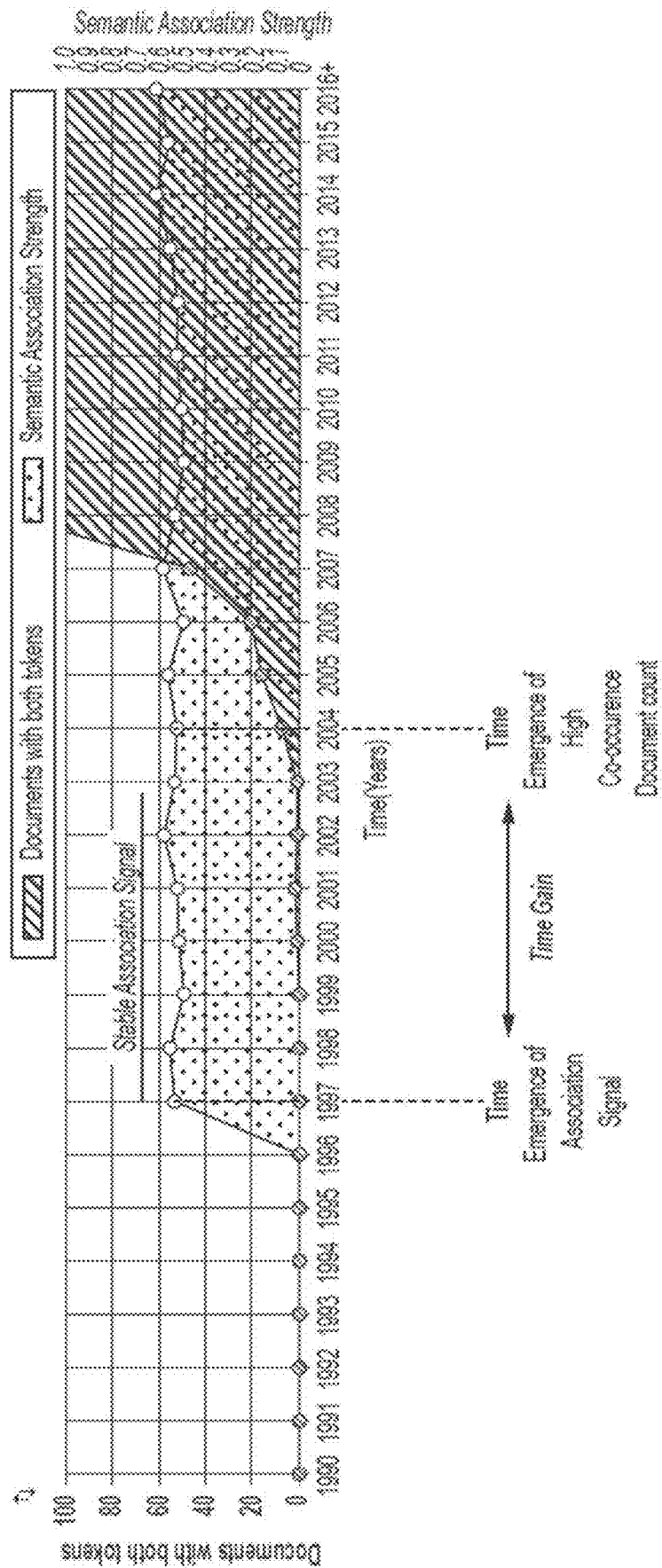
FIG. 23 illustrates PTEN-KRAS gene-gene temporal analysis in accordance with some embodiments of the present disclosure.

According to some embodiments, the Time Gain between when the method here described gives a strong Semantic Association Score for two Life Sciences entity pairs and when enough number of documents co-cite the pair of words or phrases is a salient application of the system. FIG. 23 provides an exemplary PTEN-KRAS temporal analysis in accordance with some embodiments of the present disclosure. FIG. 23 shows a graph that is similar to the graphs shown in FIGS. 20, 22A-22B, except the graph in FIG. 23 is for the entities PTEN and KRAS. The oncogenes PTEN and KRAS were not documented to be associated to each other until the year 2000 (Ikeda, T.; Yoshinaga, K.; Suzuki, A.; Sakurada, A.; Ohmori, H.; Horii, A. Anticorresponding Mutations of the KRAS and PTEN Genes in Human Endometrial Cancer. Oncol. Rep. 2000, 7, 567-570), a full 3 years after the semantic association score between PTEN and KRAS increased to significant level, providing an ample window of opportunity. Once a significant increase in the association score is detected, this can be marked as the year of interest (shown as "Time—Emergence of Association Signal" in FIG. 23). In cases where the signal oscillates, it can be advantageous to wait for stabilization of the association (i.e., Time—Stabilization of Association Score), which in this PTEN-KRAS example is simultaneous with its emergence. The Time Gain is defined as the time-period between the Emergence of Association Signal and the time when the co-occurrence documents count increases significantly (shown as "Time—Emergence of High co-occurrence Document Count" in FIG. 23), which is indicative of scientific community awareness of the association.

In some embodiments, if one could predict the association of a pair of currently-unrelated disease biomarkers, this could be used to shed insight into the molecular mechanism of the disease. Such insights can dramatically accelerate the pace of pharmaceutical and clinical R&D efforts. As a proof of concept, we have documented several additional retrospective case studies where the Semantic Association Score did predate a subsequent significant biological discovery and publication. These findings validate the system described herein that utilizes Semantic Association Score (Cosine Distance between word or phrase pairs) dynamics, and provides concrete examples where knowing said information at the time would have added tremendous value to ventures in that space. These additional illustrative exampled are outlined in FIGS. 24-27, which show graphs that are similar to the graphs shown in FIGS. 20, 22A-22B, and 23, except with different input values, such as entities.

Figure 24:
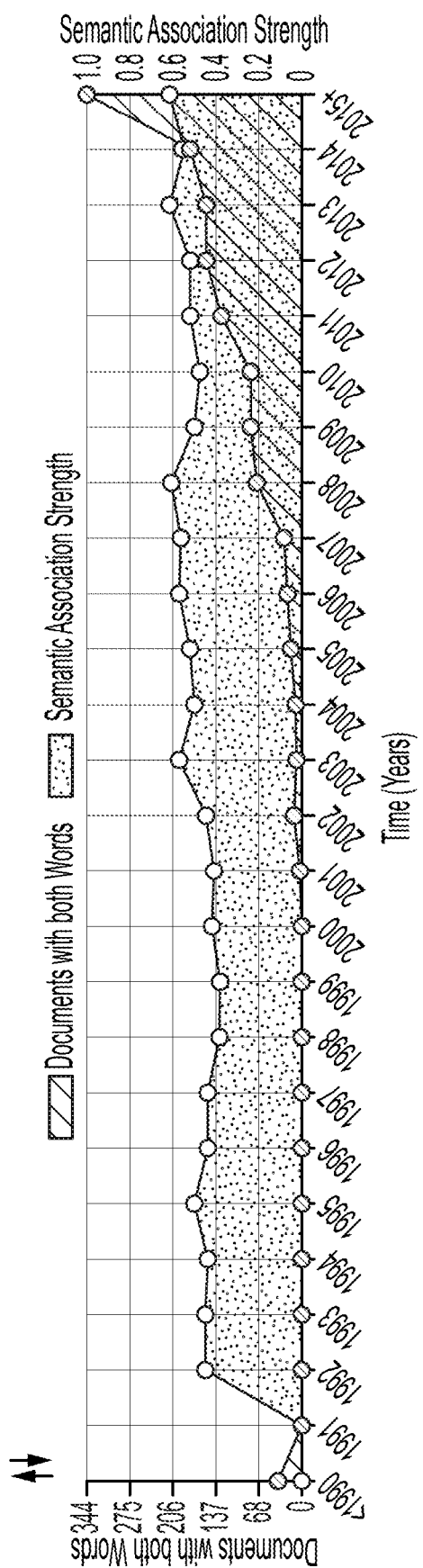
FIG. 24 illustrates AML1 (RUNX1)-FLT3 gene-gene association temporal analysis in accordance with some embodiments of the present disclosure.

FIG. 24 illustrates AML1 (RUNX1)—FLT3 gene-gene association temporal analysis in accordance with some embodiments of the present disclosure. AML1 (RUNX1) and FLT3 are two genes tightly associated with acute myeloid leukemia, and their clear connection was not fully explored until after 2002 (de Guzman, C. G.; Warren, A. J.; Zhang, Z.; Gartland, L.; Erickson, P.; Drabkin, H.; Hiebert, S. W.; Klug, C. A. Hematopoietic Stem Cell Expansion and Distinct Myeloid Developmental Abnormalities in a Murine Model of the AML1-ETO Translocation. Mol. Cell. Biol. 2002, 22, 5506-5517). This is almost 10 years after a disclosed system detected a strong semantic association score between these two genes.

Figure 25:
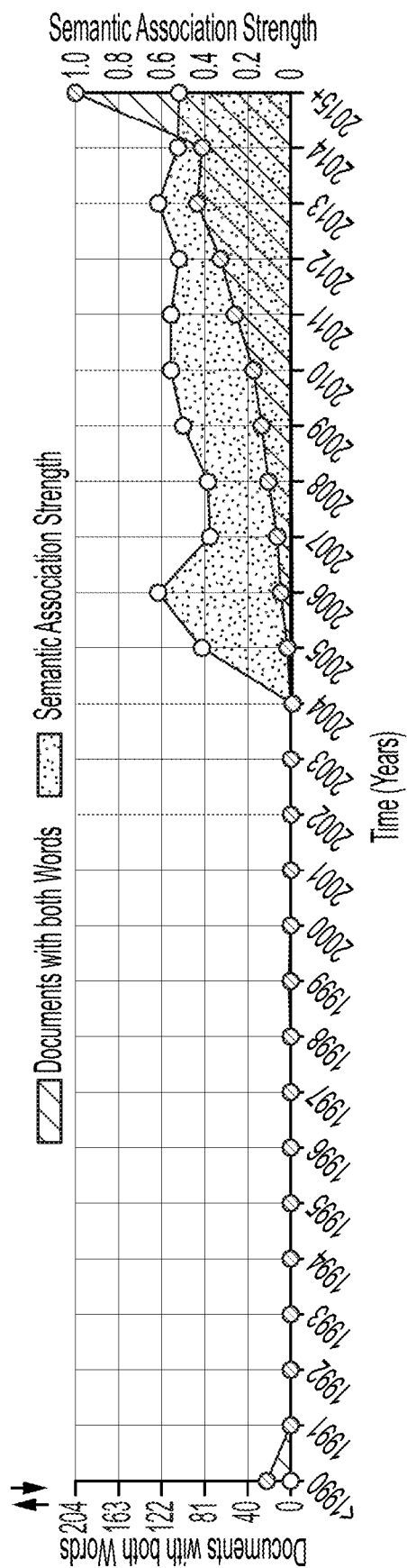
FIG. 25 illustrates Atypical Hemolytic Uremic Syndrome-CFH (disease-gene) Temporal Analysis in accordance with some embodiments of the present disclosure.

FIG. 25 illustrates Atypical Hemolytic Uremic Syndrome—CFH (disease-gene) temporal analysis in accordance with some embodiments of the present disclosure. In this case a single document published in 2005, describing a novel association between Complement Regulatory Gene Factor H (CFH) and atypical hemolytic uremic syndrome (Hageman, G. S.; Anderson, D. H.; Johnson, L. V.; Hancox, L. S.; Taiber, A. J.; Hardisty, L. I.; Hageman, J. L.; Stockman, H. A.; Borchardt, J. D.; Gehrs, K. M.; et al. A Common Haplotype in the Complement Regulatory Gene Factor H (HF1/CFH) Predisposes Individuals to Age-Related Macular Degeneration. PNAS 2005, 102, 7227-7232), managed to maximize the semantic association score between the two terms. Conventional assumptions would have warranted caution in exploring this association, whereas the score from a disclosed system suggests it would be prudent to pursue it.

Figure 26:
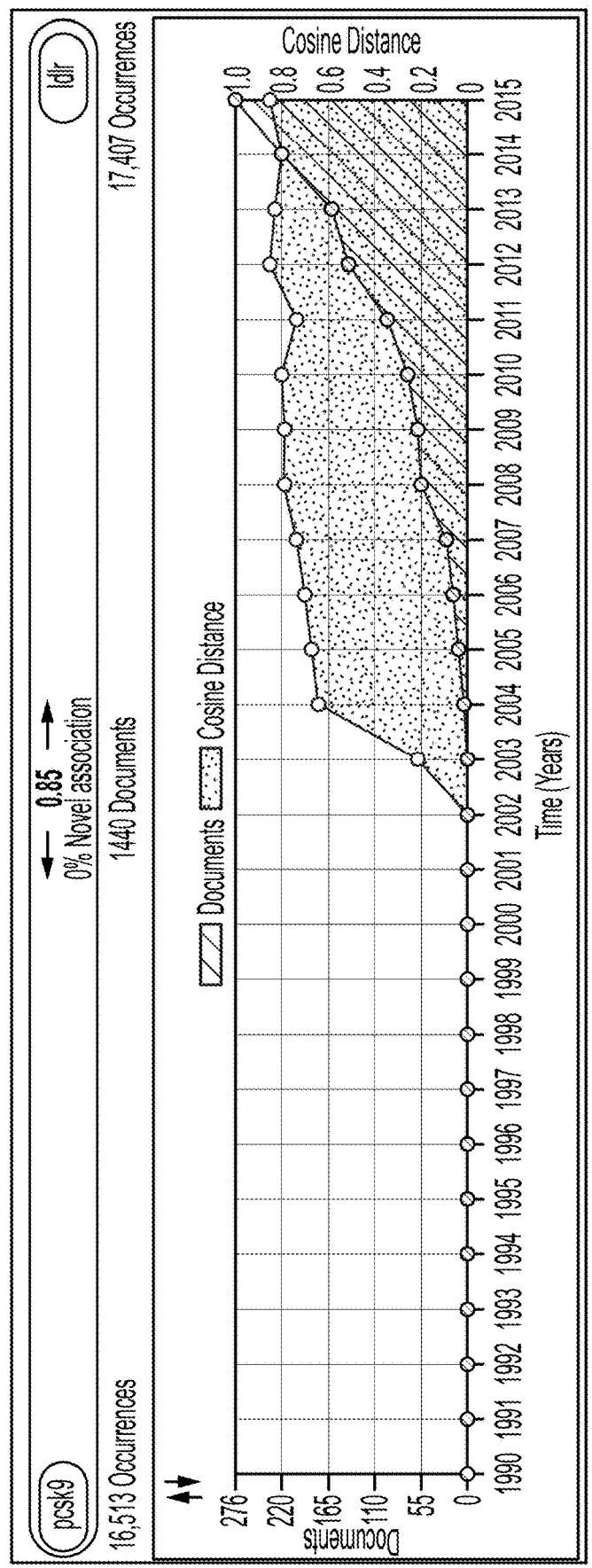
FIG. 26 illustrates PCSK9-LDLR (Gene-gene) temporal analysis in accordance with some embodiments of the present disclosure.

FIG. 26 illustrates PCSK9-LDLR (Gene-gene) temporal analysis in accordance with some embodiments of the present disclosure. In this case, a 2004 study that first observed a correlation in expression of PCSK9 to knockdown of LDLR (Maxwell, K. N.; Breslow, J. L. Adenoviral-Mediated Expression of Pcsk9 in Mice Results in a Low-Density Lipoprotein Receptor Knockout Phenotype. PNAS 2004, 101, 7100-7105) dramatically increased the semantic association score between the two genes, well before a number of subsequently published studies validated this relationship.

Figure 27:
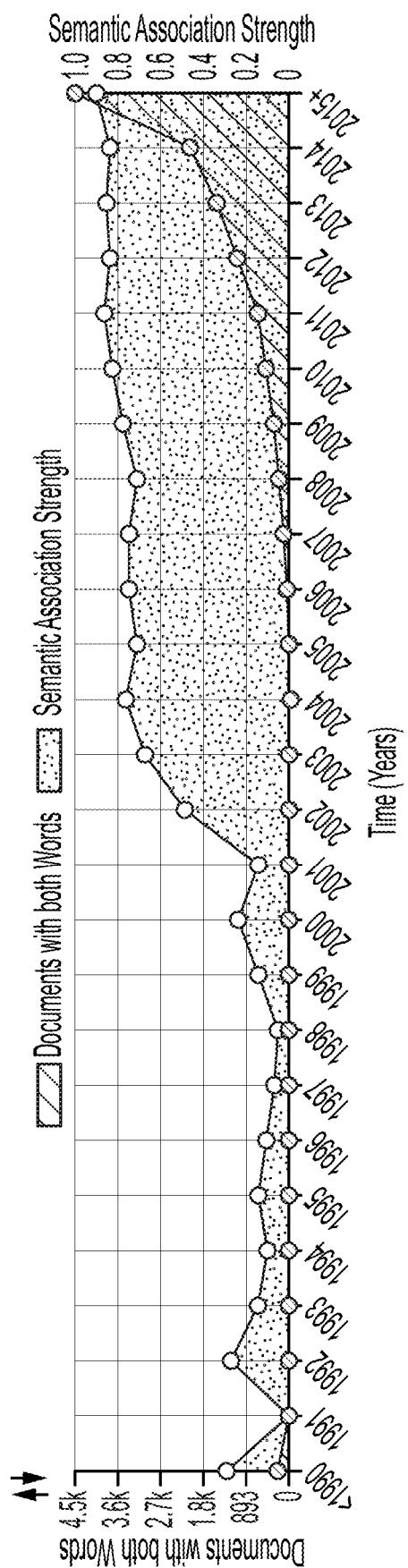
FIG. 27 illustrates PCSK9-LDLR (Gene-gene) temporal analysis in accordance with some embodiments of the present disclosure.

FIG. 27 illustrates PCSK9-LDLR (Gene-gene) temporal analysis in accordance with some embodiments of the present disclosure. Another example where semantic association score gives validity to published studies is the discovery of an association between oncogenes BRAF and KRAS in 2002. (Rajagopalan, H.; Bardelli, A.; Lengauer, C.; Kinzler, K. W.; Vogelstein, B.; Velculescu, V. E. Tumorigenesis: RAF/RAS Oncogenes and Mismatch-Repair Status. Nature 2002, 418, 934-934.) That single study increased the association score significantly, and predates increases in document counts as well.

Figure 49:
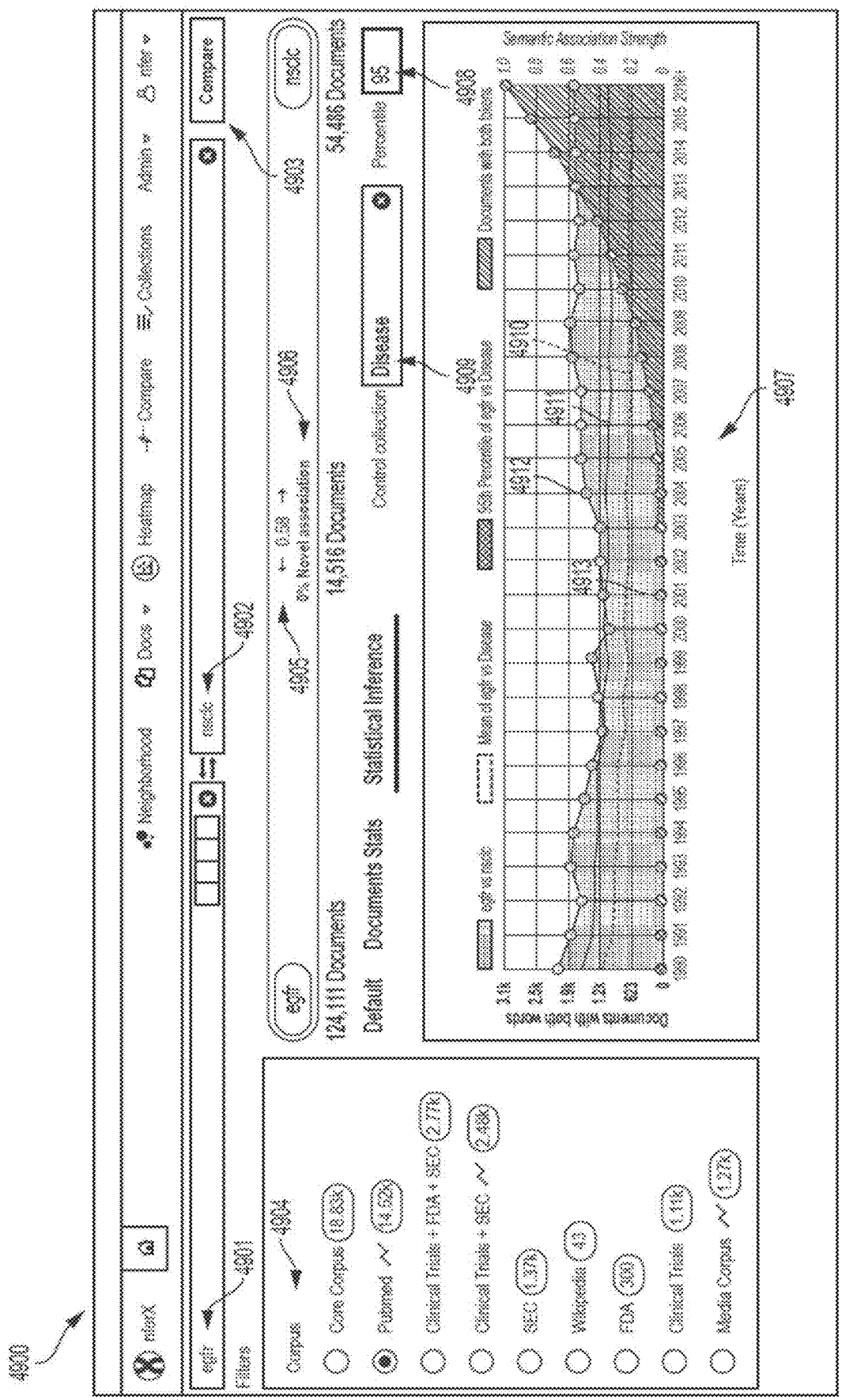
FIG. 49 illustrates an exemplary user interface for a temporal analysis graph in accordance with some embodiments of the present disclosure.

FIG. 49 illustrates an exemplary user interface 4900 for a temporal analysis graph in accordance with some embodiments of the present disclosure. The user interface 4900 can be used to perform a temporal analysis for two entities. In some embodiments, the two entities can be entered into a first entity box 4901 and a second entity box 4902. The user can click on the compare button 4903 to perform a temporal analysis between the two entities. For example, the user can enter "egfr" in the first entity box 4901 and "nscic" in the second entity box 4902. The user can then click on the "Compare" button 4903 to produce a temporal analysis graph 4907. In this example, the entity "egfr" and the entity "nscic" have been analyzed over a time period between 1990 and 2016, where there are 27 times slices (1 time slice per year).

In some embodiments, the temporal analysis graph 4907 can include one or more lines to provide information regarding the two entities. A semantic strength association line 4912 can represent the semantic association strength between the entity "egfr" and the entity "nscic" over the time period. A "Documents with both tokens" line 4913 can show the numbers of documents that contain both "egfr" and "nscic" over the time period. The mean line 4910 can show the mean of the semantic association strength for all queries of "egfr" vs. the entities in the Disease entity type over the time period. The 95th percentile line 4911 can show the 95th percentile of the semantic association strength for all queries of "egfr" vs. the entities in the Disease entity type over the time period. In this example, the lines 4910, 4911, 4912, and 4913 have been drawn based on 27 plotted points. The time period, the number of plotted points (which are based on the number of time slices), the percentile, and any other setting in this graph can be customized.

In some embodiments, the mean line 4910 and the 95th percentile line 4911 can be compared to the semantic strength association line 4912 to see whether the semantic strength between "egfr" and "nscic" is particularly strong. For example, the higher the semantic strength association line 4912 relative to the $95^{th}$ percentile line 4911, the more likely that the semantic strength between "egfr" and "nsclc" is particularly strong.

In some embodiments, the universe of corpus 4904 that is used for the analysis can be selected. In this example, the Pubmed database has been selected, causing the temporal analysis graph 4907 to be produced based on this database. In some embodiments, the control collection 4909 can be customized. In this example, the control collection is "Disease," which indicates that the temporal analysis graph 4907 is generated based on this entity collection. For example, the mean line 4910 is based on comparing "egfr" against the entities in the control collection "Disease" (i.e., the Disease entity type).

In some embodiments, the percentile 4908 can be customized for the temporal analysis graph 4907. For example, when the percentile 4908 is set to "95," the 95th percentile line 4911 is drawn to show the 95th percentile of the semantic association strength for all queries of a given entity vs. the entities in a given entity type. As another example, if the percentile 4908 is set to "30," a 30th percentile line can be drawn to represent the 30th percentile of the semantic association strength for all queries of a given entity vs. entities in a given entity type.

In some embodiments, the current semantic association strength 4905 and the current novel association 4906 can be displayed. In this example, the current semantic association strength between "egfr" and "nscic" is shown as "0.58." The novel association between them is "0%," which can indicate that the probability of the association between the two entities being novel is zero. In some embodiments, the novelty score can be inversely proportional to the total number of documents with both tokens.

Figure 50:
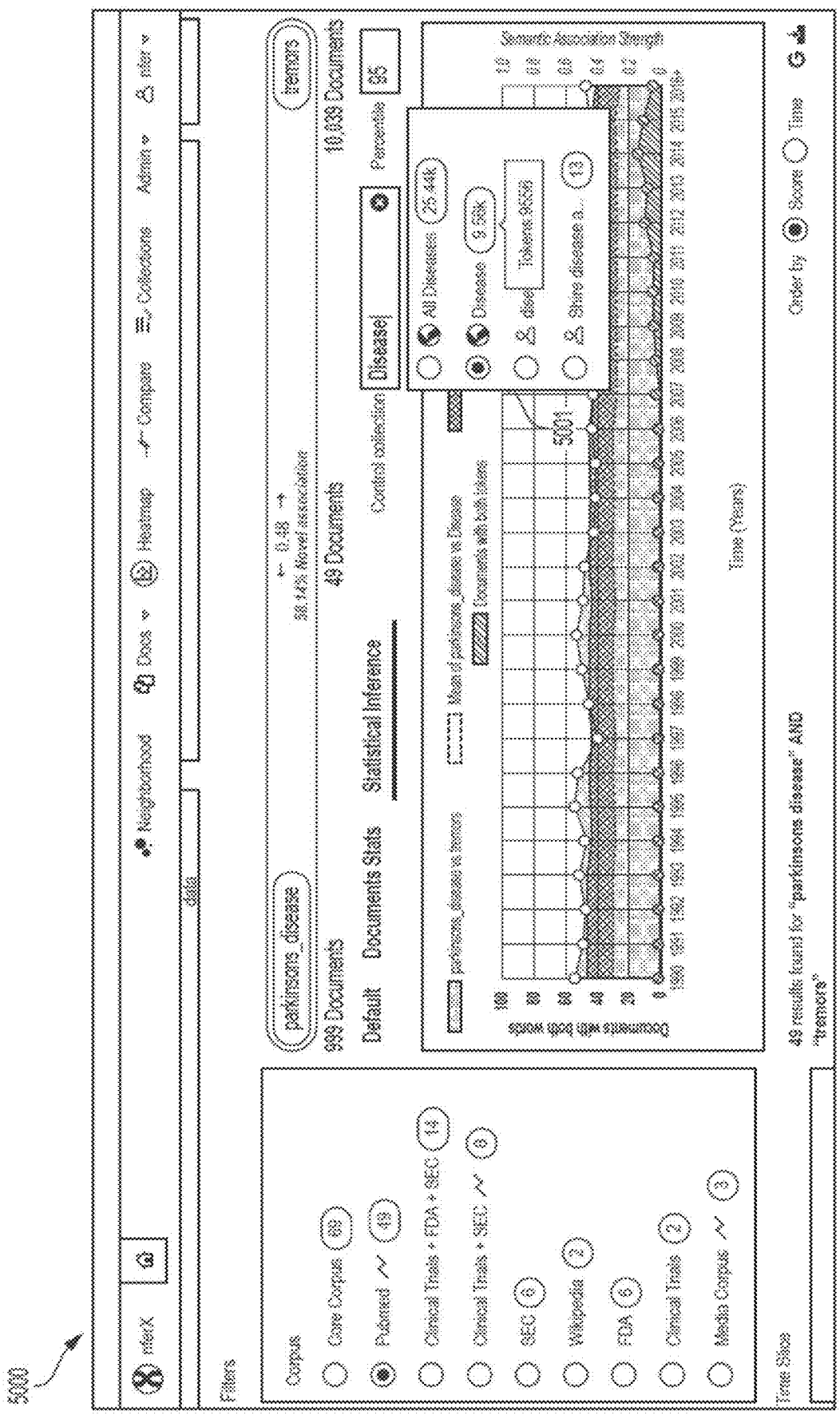
FIG. 50 illustrates an exemplary knowledge graph interface with a temporal analysis graph in accordance with some embodiments of the present disclosure.

FIG. 50 illustrates an exemplary knowledge graph interface 5000 with a temporal analysis graph in accordance with some embodiments of the present disclosure. The knowledge graph interface 5000 can show that all or a subset of an entity type (e.g., "All Diseases") can be selected (5001) as the control collection.

Figure 51:
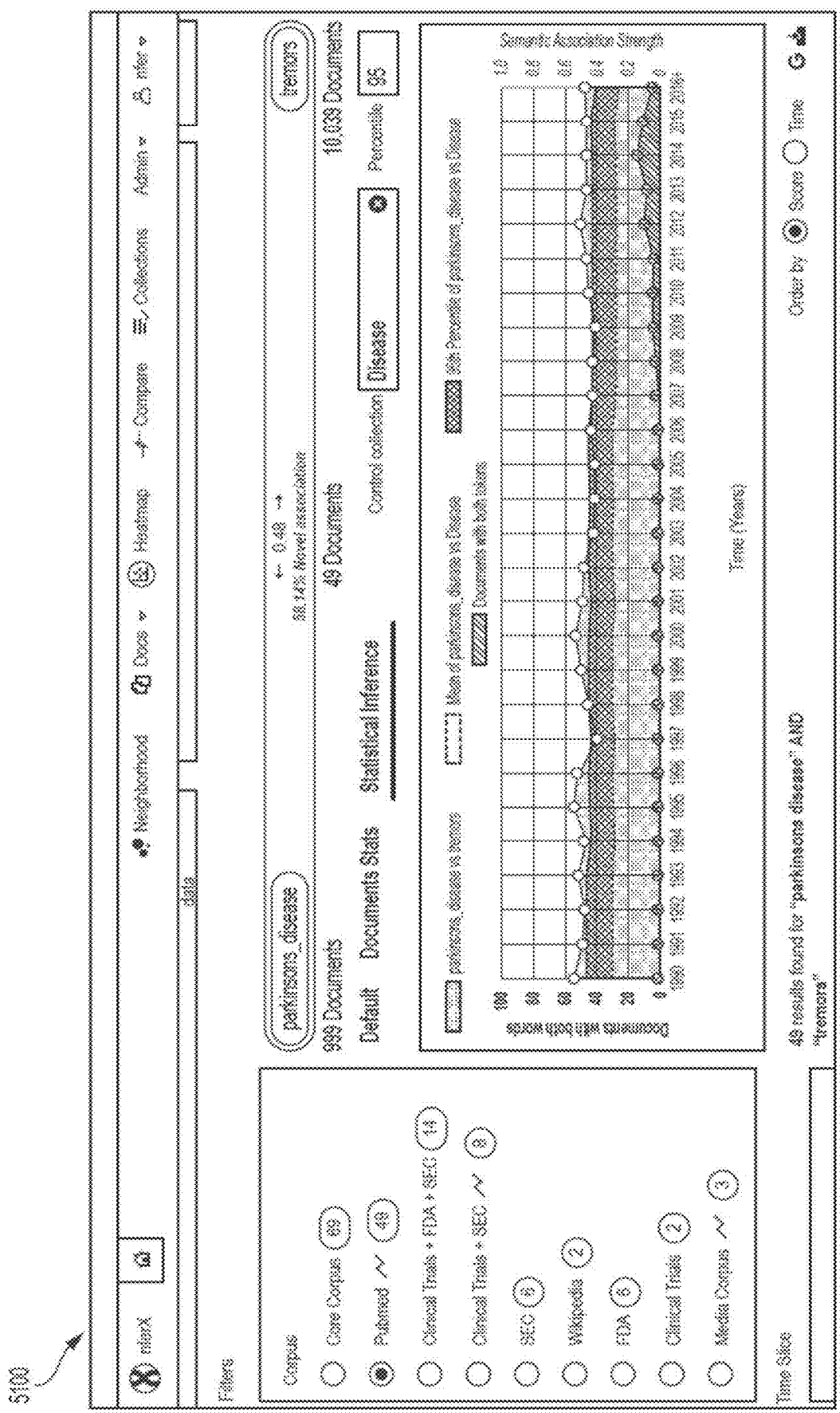
FIG. 51 illustrates an exemplary knowledge graph interface with a temporal analysis graph in accordance with some embodiments of the present disclosure.

FIG. 51 illustrates an exemplary knowledge graph interface 5100 with a temporal analysis graph in accordance with some embodiments of the present disclosure. The knowledge graph interface 5100 can show information relating to the entity "parkinsons_disease" as it relates to the entity "tremors."

We also compared all Life Sciences associations enclosed in the OpenTargets database and their relevant association score (referred to hereafter as "OT Score") to the given pairs semantic association strength. The OpenTargets Platform seeks to annotate gene-disease pairs with evidence of an association between them agglomerated from various sources, including an alternative NLP method for text-mining. Overall, we found a poor correlation between the association scores, as shown in FIG. 28.

Figure 28:
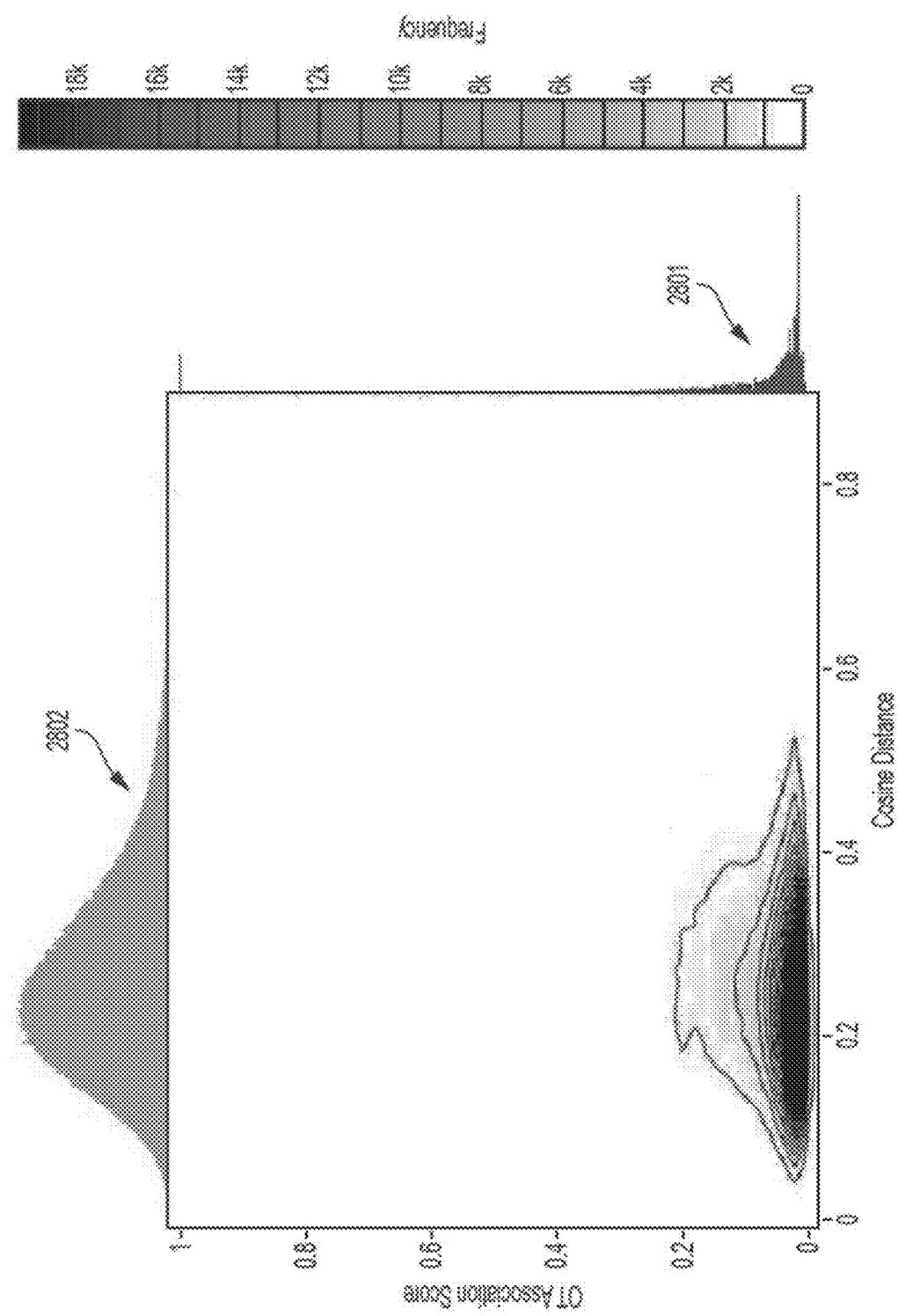
FIG. 28 illustrates a relationship between OT Score and cosine distance (semantic association score) in accordance with some embodiments of the present disclosure.

FIG. 28 illustrates a relationship between OT Score and cosine distance (semantic association score) in accordance with some embodiments of the present disclosure. This is a plot of OpenTargets association score (OT Score) with respect to their Cosine Distance (Semantic Association Score) for all Life Science entity pairs found in OpenTargets. The distribution graph 2801 (on the right side of the y-axis) is based on the OT Association Score (where closer to 1 represents higher association), and the distribution graph 2802 (on top of the x-axis) is based on the Cosine Distance (which in turn is based on analysis of thousands of gene/disease associations). The rectangle area (enclosed by the x-axis, y-axis, and the distributions graphs 2801, 2802) represents the mapping between the OT Association Score and the cosine distance. FIG. 28 shows that this mapping is not one-to-one. Disclosed systems and methods have, thus, discovered that there are differences between what the OT Association Score reveals and what the Cosine Distance reveals. These differences can be due to errors and/or deficiency in the OT Association Score.

Further inspection revealed that OT Scores are bimodal, with a small subset having a very high score and the rest having a low score. These high scores are attributed to well-known gene-disease associations (e.g., BRAF-neoplasms), which have a corresponding high Semantic Association Score. This exemplifies why current approaches to biological association discovery simply recapitulate what is already known in the literature and have little to no predictive capability.

Figure 29:
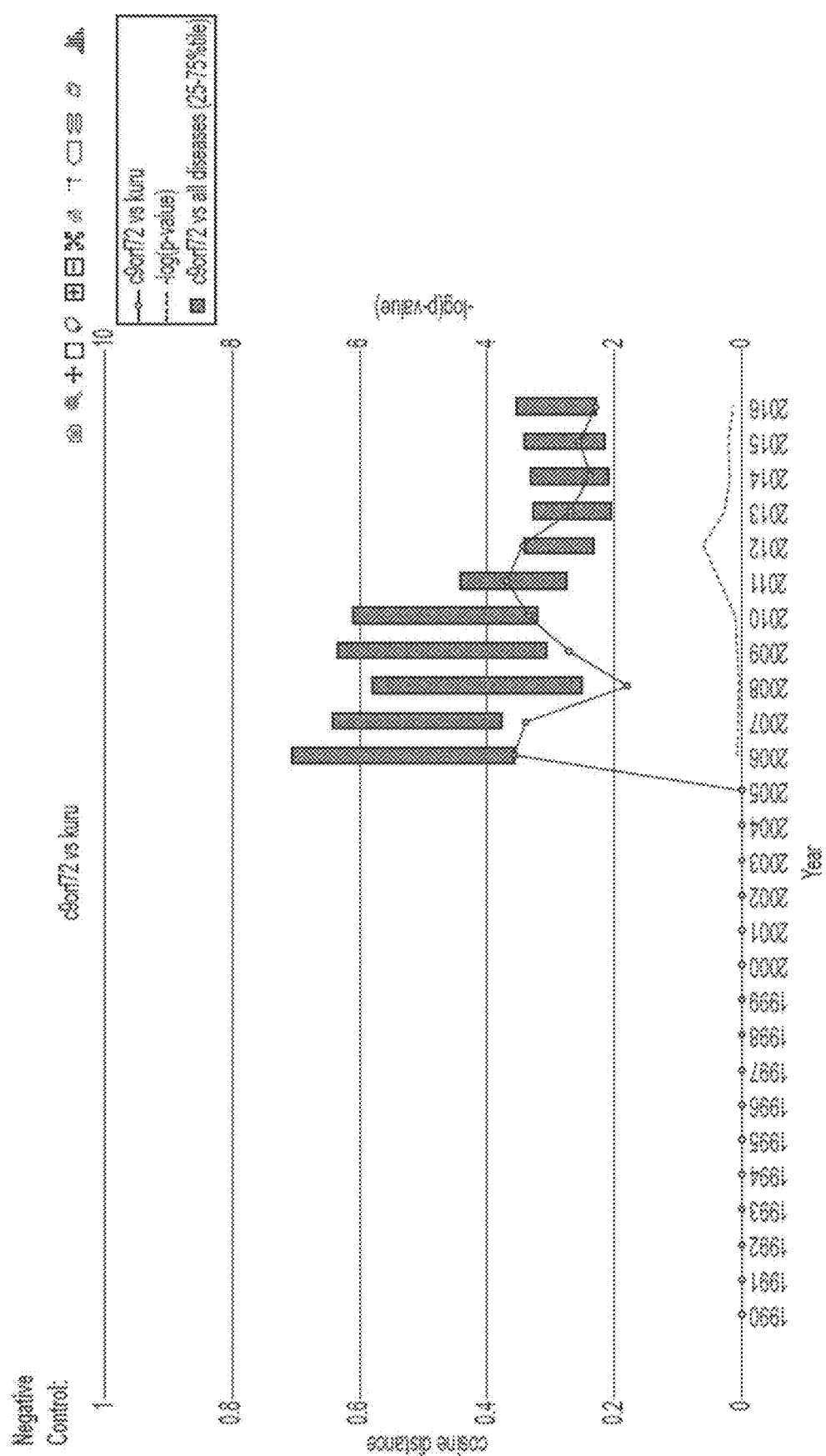
FIG. 29 illustrates a negative control graphical representation of temporal statistical inference for a non-significant gene-disease interaction in accordance with some embodiments of the present disclosure.

FIG. 29 illustrates a graphical representation of temporal statistical inference for a non-significant gene-disease interaction (i.e., the negative control). The "c9orf72 vs kuru" line represent the cosine distance between the gene and disease terms (c9orf72 and kuru, respectively). The "c9orf72 vs all diseases (25-75% tile) bars represent the 25-75th percentiles for the cosine distances between c9orf72 and all diseases. The "-log(p-value)" line represents the negative log of the p-value for the gene-disease relationship queried being different from the true disease-gene relationship mean. In this case, the gene c9orf72 is not associated with Kuru.

Figure 30:
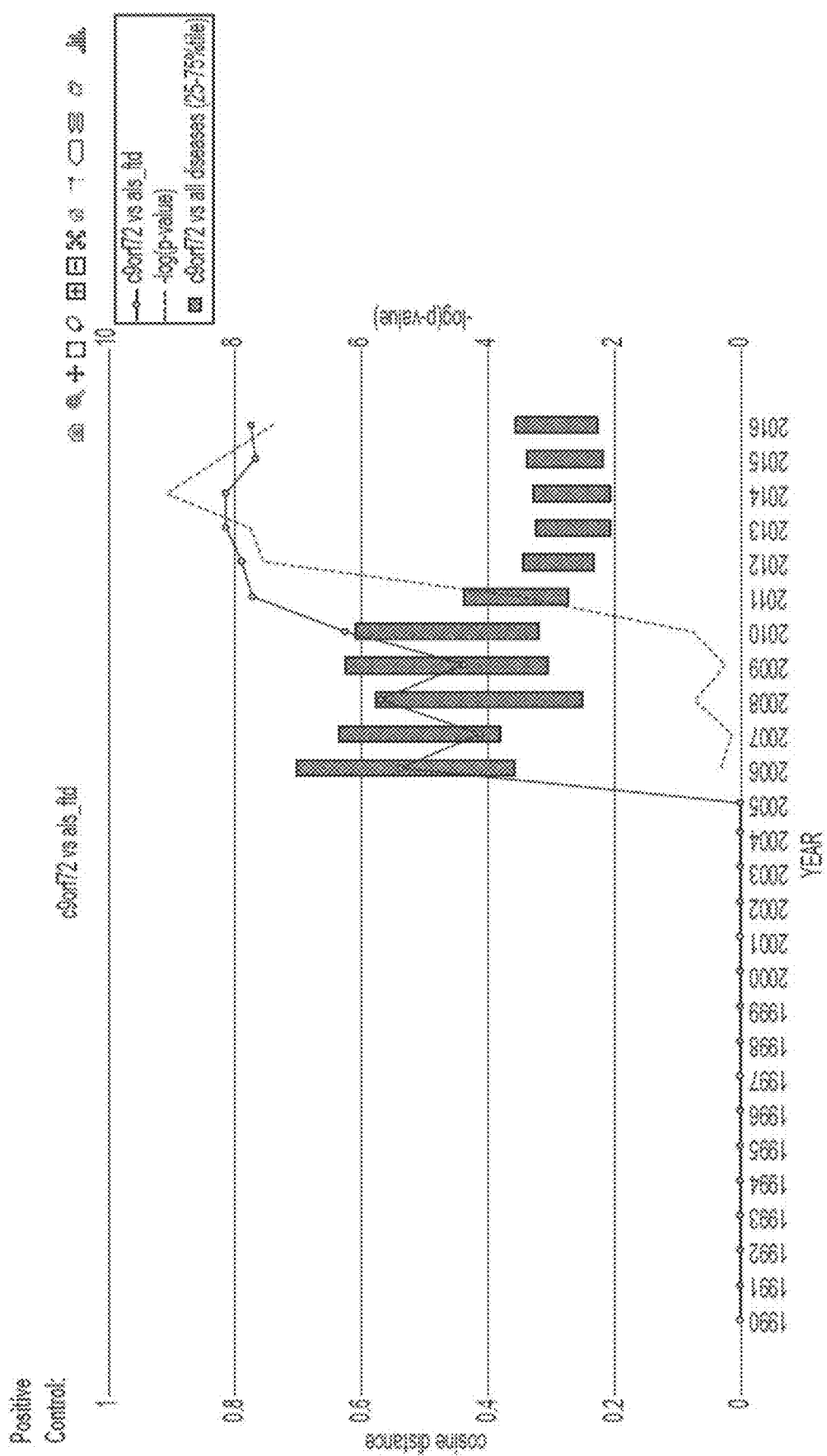
FIG. 30 illustrates a positive control graphical representation of temporal statistical inference for a significant gene-disease interaction in accordance with some embodiments of the present disclosure.

FIG. 30 illustrates a graphical representation of temporal statistical inference for a significant gene-disease interaction (i.e., the positive control). The "c9orf72 vs als_ftd" line represents the cosine distance between the gene and disease terms (c9orf72 and Amyotrophic Lateral Sclerosis/Frontotemporal Dementia (als_ftd), respectively). The "c9orf72 vs all diseases (25-75% tile)" bars represent the 25-75th percentiles for the cosine distances between c9orf72 and all diseases. The "-log(p-value)" line represents the negative log of the p-value for the gene-disease relationship queried being different from the true disease-gene relationship mean. In this case, repeats in the gene c9orf72 cause the disease Amyotrophic Lateral Sclerosis/Frontotemporal dementia. This is clearly shown when the negative log of the p-value significantly jumps up in the 2010-12 timeframe. This timeframe to the year when the number of co-occurring documents between c9orf72 and Amyotrophic Lateral Sclerosis increases substantially represents another instance of the "Time Gain."

Disclosed systems and methods can capture evolution of semantic associations between two entities over a period of time. In some cases, as semantic associations evolve over time for a pair of entities, the user or the system can detect an increase in semantic associations that may or may not be statistically significant. In some embodiments, disclosed systems and methods can detect a time at which a statistically significant increase occurs for a pair of entities by using various methods, including a method that uses the Sigmoid Curve. In some embodiments, semantic association scores can be generated between a first entity (which can be associated with a first entity collection) and a second entity (which can be associated with a second entity collection) for a time period. Semantic association scores can also be generated between the first entity and the entities in the second entity collection. In some embodiments, when determining these semantic association scores, the second entity itself can be excluded from the calculation. Details of systems and methods that calculate these first and second semantic association scores have been described in other parts of this disclosure. (See e.g., FIGS. 19, 20, 22-27, 49-51 and the descriptions for these figures.)

In some embodiments, the p-values can be generated by the p-value approach to hypothesis testing when evaluating whether the semantic association score of the first entity vs. the second entity is statistically significant when compared with the semantic association score of the first entity vs. all entities of the second entity collection. In other words, the p-value can be employed as a measure of statistical significance of the first entity vs. the second entity, as opposed to the first entity vs. all entities of the second entity collection. In some embodiments, a null hypothesis can state that the semantic association of the first entity vs. the second entity is not statistically significant when compared with the semantic association score of the first entity vs all entities of the second entity collection. A low p-value indicates that the null hypothesis should be rejected. Because a low p-value results in a high-log(p-value), a high-log(p-value) should cause us to reject the null hypothesis. Thus, if the semantic association of the first entity vs. the second entity is significant, a relatively high-log(p-value) will result, and we can reject the null hypothesis.

In some embodiments, a negative log p-value curve can be drawn with the time period on the x-axis and the negative log p-value on the y-axis (see FIGS. 29 and 30). In some embodiments, when there is an increase in the semantic association strength between the first entity and the second entity over time, the negative log p-value increases over the time period in such a fashion that the Sigmoid curve can fit over the negative log p-value curve. In some embodiments, before the Sigmoid curve is fitted, the negative log p-value can be smoothened using a filter, such as the Savitzky-Golay filter. In some embodiments, one or more fitting parameters associated with the Sigmoid curve can be optimized for speed and accuracy.

In some embodiments, after the negative log p-value curve has been fitted with the Sigmoid curve, the following formulas associated with the Sigmoid curve can be used to determine (1) the time of increase (which is $X_0$); (2) the saturation value (which is K+c, at $X=\infty$); and (3) the area under the curve (AUC):

The Sigmoid fit formula is:

$$y = \frac{K}{1+e^{-k(x-x_o)}} + c$$

The area under the curve (AUC) formula is:

$$AUC = \frac{K}{k}\log_e\left(\frac{1+e^{k(x_f-x_o)}}{1+e^{k(x_i-x_o)}}\right) + c(x_f - x_i)$$

In some embodiments, the saturation value can be used to approximate the final (e.g., maximum) negative log p-value.

In some embodiments, a set of negative log p-values can be calculated for multiple pairs of entities, where, for each pair, one entity in the pair is from a first entity collection and the other entity in the pair is from a second entity collection. In some embodiments, all the possible pairs of entities between two entity collections can be used to calculate a set of negative log p-values. In some embodiments, the negative log p-value curve, as described above, can be created to determine the time of increase, the saturation value, and/or the AUC. In some embodiments, these multiple pairs can be compared manually and/or automatically. In some embodiments, these multiple pairs can be displayed in a user interface.

Figure 59:
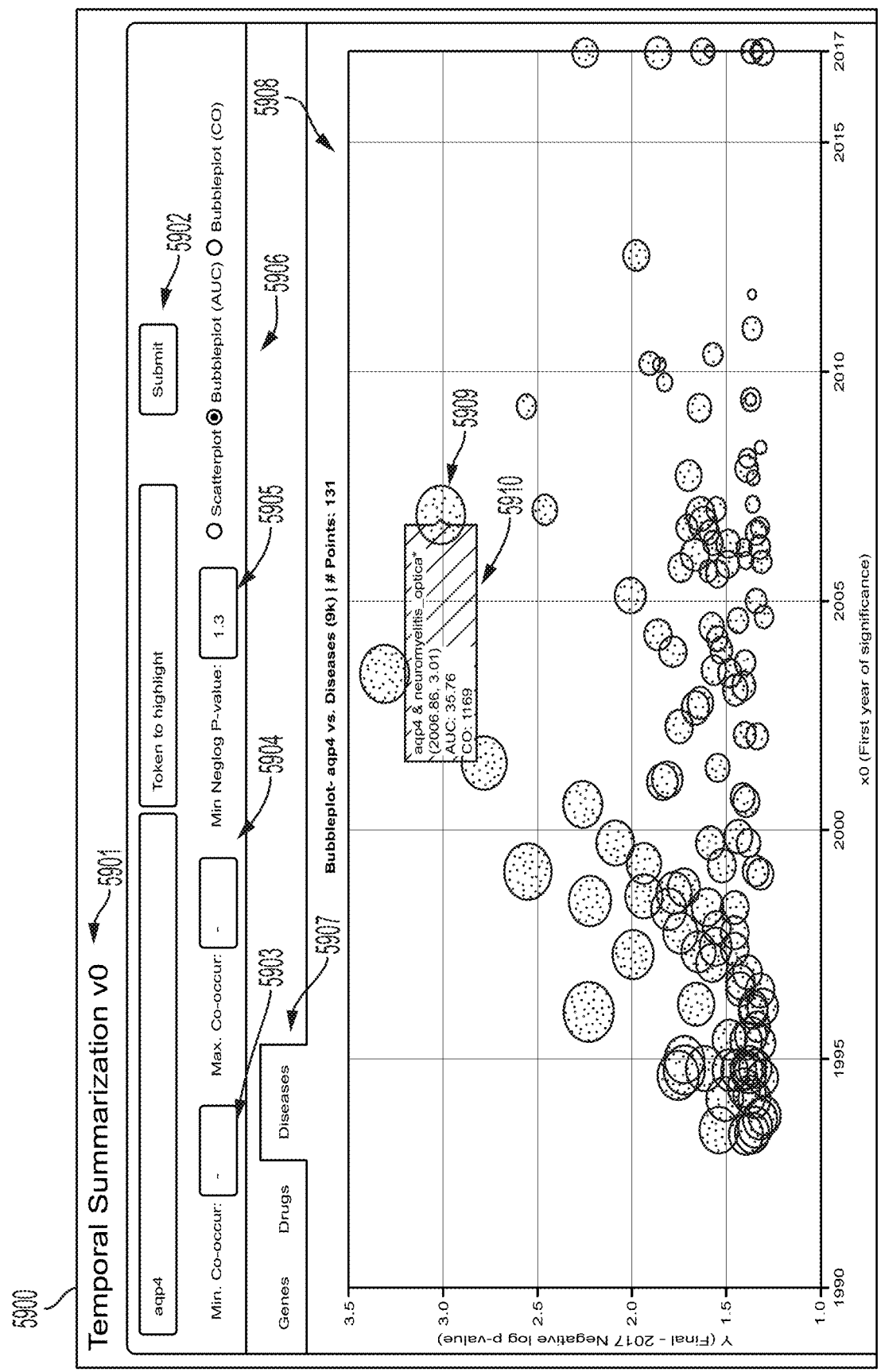
FIG. 59 illustrates an exemplary knowledge graph interface with a temporal analysis graph in accordance with some embodiments of the present disclosure.

FIG. 59 illustrates an exemplary knowledge graph interface 5900 with a temporal analysis graph in accordance with some embodiments of the present disclosure. The knowledge graph interface 5900 can provide semantic association strength information for multiple pairs of entities. The knowledge graph interface 5900 includes a query term box 5901, a submit button 5902, a minimum co-occur filter 5903, a max co-occur filter 5904, a minimum negative log P-value filter 5905, a graph type selection 5906, a comparison semantic entity collection tab 5907, a graph rendering section 5908, an entity pair representation 5909, and an entity pair description box 5910.

An example use case starts when a user enters the gene "aqp4" as a query term into the query term box 5901 and clicks the submit button 5902. Because the comparison semantic entity collection tab 5907 is selected as Diseases (this can be manually or automatically selected), the system calculates a series of negative log p-values over time between "aqp4" and one or more of the entities (e.g., 1, 2, 5, all entities) in the Diseases collection. Each "bubble" (e.g., bubble 5909) can represent an entity pair, for which the negative log p-values over time have been calculated. In some embodiments, one or more entity pairs can be filtered out before, during, and/or after the negative log p-value time series calculations have been performed based on one or more conditions. For example, the user can filter out (1) those entity pairs whose number of co-occurrences of the entities in the pair are less than the minimum co-occurrence value (as specified in the minimum co-occur filter 5903), (2) those entity pairs whose number of co-occurrences of the entities in the pair are greater than the maximum co-occurrence value (as specified in the maximum co-occur filter 5904), and/or (3) those entity pairs whose negative log p-values are less than the minimum negative log p-value (as specified in the minimum negative log P-value filter 5905). In some embodiments, the bubbles corresponding to the values associated with the entity pairs are plotted in the graph rendering section 5908. The bubble for a particular entity pair is placed along the x-axis and y-axis according to the time of increase value and final-log(p-value), respectively, as determined from the curve fits. In some embodiments, the size of a bubble can be directly proportional to the AUC value calculated for the entity pair represented by the bubble, again, as determined by the curve fits. Although not shown, the size of the bubble can be made proportional to the number of co-occurrences between the entity pair in the corpora being analyzed when the user makes the appropriate selection in the graph type selection 5906 control. In some embodiments, detailed information can be provided for each bubble. For example, by placing the mouse cursor on the bubble 5909 (or by using any other suitable triggering mechanism), the entity pair description box 5910 can be displayed. The entity pair description box 5910 can display information about the entity pair (e.g., aqp4 & neuromyelitis_optica), the date of the increase of the semantic association strength for the entity pair (e.g., $86^{th}$ day of 2006), the negative log p-value (e.g., 3.01), the AUC value (e.g., 35.76), and/or the number of co-occurrences (e.g., 1169). In some embodiments, by using the knowledge graph interface 5900, the use can generate and/or display only entity pairs that have statistical significant associations between entities. In some embodiments, the knowledge graph interface 5900 can uncover entities with statistically strong semantic association strengths even when those entities' co-occurrence is low or non-existent.

In some embodiments, the following formula can be used to describe a relationship between a negative log p-value and a percentile of the first entity vs. second entity, where the percentile of the first entity vs. second entity is the percentile of the semantic association strength between the first entity and the second entity, as compared to the semantic association strengths between the first entity and all entities of the second semantic entity collection:

Negative log P-value=$-\log_{10}$(1−Percentile/100).

For example, a 95th percentile gives a negative log p-value of about 1.3. In some embodiments, other formulas can be used to describe relationships between negative log p-values and percentiles.

In some embodiments, one or more semantic entities from the second semantic entity collection can be omitted when calculating the semantic association strengths between the first entity and entities of the second entity collection, although the above steps describe that "all entities of the second entity collection" to be used. For example, such semantic association strengths can be calculated between the first entity and all the entities of the second semantic entity collection except for the second semantic entity itself.

Disclosed systems and methods can be used in, and/or expanded to industries other than life science. Other industries may have their own applicable corpus. For example, for the entertainment industry, disclosed systems and methods can use movie reviews as its corpus.

Those of skill in the art would appreciate that the various illustrations in the specification and drawings described herein can be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware, software, or a combination depends upon the particular application and design constraints imposed on the overall system. Skilled artisans can implement the described functionality in varying ways for each particular application.

Various components and blocks can be arranged differently (for example, arranged in a different order, or partitioned in a different way) all without departing from the scope of the subject technology.

Furthermore, an implementation of the communication protocol can be realized in a centralized fashion in one computer system, or in a distributed fashion where different elements are spread across several interconnected computer systems. Any kind of computer system, or other apparatus adapted for carrying out the methods described herein, is suited to perform the functions described herein.

A typical combination of hardware and software could be a general purpose computer system with a computer program that, when being loaded and executed, controls the computer system such that it carries out the methods described herein. The methods for the communications protocol can also be embedded in a non-transitory computer-readable medium or computer program product, which comprises all the features enabling the implementation of the methods described herein, and which, when loaded in a computer system is able to carry out these methods. Input to any part of the disclosed systems and methods is not limited to a text input interface. For example, they can work with any form of user input including text and speech.

Computer program or application in the present context means any expression, in any language, code or notation, of a set of instructions intended to cause a system having an information processing capability to perform a particular function either directly or after either or both of the following a) conversion to another language, code or notation; b) reproduction in a different material form. Significantly, this communications protocol can be embodied in other specific forms without departing from the spirit or essential attributes thereof, and accordingly, reference should be had to the following claims, rather than to the foregoing specification, as indicating the scope of the invention.

The communications protocol has been described in detail with specific reference to these illustrated embodiments. It will be apparent, however, that various modifications and changes can be made within the spirit and scope of the disclosure as described in the foregoing specification, and such modifications and changes are to be considered equivalents and part of this disclosure.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods and media for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. A method of generating semantic information between entities, comprising:
    identifying a plurality of semantic entities in one or more corpora, wherein the semantic entities include one or more of single words or multi-word phrases;
    identifying a plurality of semantic entity types in the one or more corpora;
    associating one or more semantic entity types with the semantic entities of the plurality of semantic entities;
    generating word embeddings for the plurality of semantic entities;
    determining a first set of semantic association scores between semantic entities from the plurality of semantic entities based on the word embeddings;
    receiving a query term;
    determining a query term entity type associated with the query term, wherein determining the query term entity type comprises determining if the query term corresponds to at least one semantic entity that is associated with the word embeddings;
    generating a first list of resulting semantic entities associated with the query term based on the first set of semantic association scores and the query term entity type;
    generating a second list of semantic entity collections based on the semantic entity types associated with the semantic entities of the first list of resulting semantic entities, wherein each semantic entity collection from the second list is associated with a semantic entity type; and
    providing an output based on the second list of semantic entity collections.

2. The method of claim 1, wherein the plurality of semantic entity types is identified based on one or more of: a structured database, a custom list of entity types, an output from a neural network, an output from supervised machine learning, or an output from unsupervised machine learning.

3. The method of claim 2, wherein the neural network architecture is one or more of: a recurrent neural network (RNN) or a Long Short Term Memory (LSTM).

4. The method of claim 1, wherein the method further comprises identifying semantic entities using an automatic methods of identifying one or more single words or multi-word phrases as semantic entities belonging to semantic collections.

5. The method of claim 1, wherein generating the second list comprises generating the second list of semantic entity collections as a function of a minimum semantic association score.

6. The method of claim 1, wherein generating the second list comprises generating the second list of semantic entity collections as a function a minimum number of occurrences of the resulting semantic entity in the one or more corpora.

7. The method of claim 1, wherein the method further comprises generating a third list of semantic association scores.

8. The method of claim 7, wherein the third list comprises semantic association scores between each of the resulting semantic entities from the first list and the second list.

9. The method of claim 1, wherein the first list comprises the semantic entities associated with the same semantic entity type as the query term entity type.

10. The method of claim 1, wherein the method further comprises generating one or more knowledge graphs as a function of the word embeddings.

11. The method of claim 1, wherein the method further comprises generating a second set of semantic association scores as a function of the second list.

12. A system for generating semantic information between entities, comprising:
- a memory that stores a module; and
- a processor configured to run the module stored in the memory that is configured to cause the processor to:
  - identify a plurality of semantic entities in one or more corpora, wherein the semantic entities include one or more of single words or multi-word phrases;
  - identify a plurality of semantic entity types in the one or more corpora;
  - associate one or more semantic entity types with the semantic entities of the plurality of semantic entities;
  - generate word embeddings for the plurality of semantic entities;
  - determine a first set of semantic association scores between semantic entities from the plurality of semantic entities based on the word embeddings;
  - receive a query term;
  - determine a query term entity type associated with the query term, wherein determining the query term entity type comprises determining if the query term corresponds to at least one semantic entity that is associated with the word embeddings;
  - generate a first list of resulting semantic entities associated with the query term based on the a first set of semantic association scores and the query term entity type;
  - generate a second list of semantic entity collections based on the semantic entity types associated with the semantic entities of the first list of resulting semantic entities, wherein each semantic entity collection from the second list is associated with a semantic entity type; and
  - provide an output based on the second list of semantic entity collections.

13. The system of claim 12, wherein the plurality of semantic entity types is identified based on one or more of: a structured database, a custom list of entity types, an output from a neural network, an output from supervised machine learning, or an output from unsupervised machine learning.

14. The system of claim 13, wherein the neural network architecture is one or more of: a recurrent neural network (RNN) or a Long Short Term Memory (LSTM).

15. The system of claim 12, wherein the method further comprises identifying semantic entities comprises an automatic methods of identifying one or more single words or multi-word phrases as semantic entities belonging to semantic collections.

16. The system of claim 12, wherein generating the second list comprises generating the second list of semantic entity collections as a function of a minimum semantic association score.

17. The system of claim 12, wherein generating the second list comprises generating the second list of semantic entity collections as a function a minimum number of occurrences of the resulting semantic entity in the one or more corpora.

18. The system of claim 12, wherein the method further comprises generating a third list of semantic association scores.

19. The method of claim 18, wherein the third list comprises semantic association scores between each of the resulting semantic entities from the first list and the second list.

20. The system of claim 12, wherein the first list comprises the semantic entities associated with the same semantic entity type as the query term entity type.

21. The system of claim 12, wherein the method further comprises generating one or more knowledge graphs as a function of the word embeddings.

22. The system of claim 12, wherein the method further comprises generating a second set of semantic association scores as a function of the second list.

* * * * *